(12) United States Patent
Bellinger et al.

(10) Patent No.: US 12,109,305 B2
(45) Date of Patent: Oct. 8, 2024

(54) MATERIALS ARCHITECTURE FOR GASTRIC RESIDENCE SYSTEMS

(71) Applicant: Lyndra Therapeutics, Inc., Watertown, MA (US)

(72) Inventors: Andrew Bellinger, Wellesley, MA (US); Rosemary Kanasty, Somerville, MA (US); Tyler Grant, Arlington, MA (US); Nupura Bhise, Cambridge, MA (US); Robert Debenedictis, Cambridge, MA (US); Jung Yang, Brookline, MA (US); Stephen Zale, Hopkinton, MA (US); John Klier, Cambridge, MA (US)

(73) Assignee: LYNDRA THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 16/303,118

(22) PCT Filed: May 26, 2017

(86) PCT No.: PCT/US2017/034856
§ 371 (c)(1),
(2) Date: Nov. 19, 2018

(87) PCT Pub. No.: WO2017/205844
PCT Pub. Date: Nov. 30, 2017

(65) Prior Publication Data
US 2019/0254966 A1 Aug. 22, 2019

Related U.S. Application Data

(60) Provisional application No. 62/342,798, filed on May 27, 2016.

(51) Int. Cl.
| A61K 9/00 | (2006.01) |
| A61F 5/00 | (2006.01) |
| A61K 47/34 | (2017.01) |
| A61L 31/04 | (2006.01) |
| A61L 31/06 | (2006.01) |
| A61L 31/16 | (2006.01) |

(52) U.S. Cl.
CPC .......... *A61K 9/0065* (2013.01); *A61F 5/0036* (2013.01); *A61K 47/34* (2013.01); *A61L 31/06* (2013.01); *A61L 31/16* (2013.01); *A61L 31/048* (2013.01); *A61L 2300/602* (2013.01); *A61L 2300/604* (2013.01)

(58) Field of Classification Search
CPC .................................................. A61K 9/0065
See application file for complete search history.

(56) References Cited

U.S. PATENT DOCUMENTS

| 1,957,564 | A | 5/1934 | West |
| 3,154,461 | A | 10/1964 | Johnson |
| 3,531,368 | A | 9/1970 | Okamoto |
| 3,716,614 | A | 2/1973 | Watanabe |
| 3,844,285 | A | 10/1974 | Laby |
| 3,976,764 | A | 8/1976 | Watanabe |
| 4,304,767 | A | 12/1981 | Heller |
| 4,451,260 | A | 5/1984 | Mitra |
| 4,525,358 | A | 6/1985 | Baltes |
| 4,676,507 | A | 6/1987 | Patterson |
| 4,735,804 | A | 4/1988 | Caldwell |
| 4,758,436 | A | 7/1988 | Caldwell |
| 4,767,627 | A * | 8/1988 | Caldwell .............. A61K 9/0065 424/400 |
| 4,812,012 | A | 3/1989 | Terada |
| 4,996,058 | A | 2/1991 | Sinnreich |
| 5,002,772 | A | 3/1991 | Curatolo |
| 5,007,790 | A | 4/1991 | Shell |
| 5,047,464 | A | 9/1991 | Pogany |
| 5,121,329 | A | 6/1992 | Crump |
| 5,340,433 | A | 8/1994 | Crump |
| 5,369,142 | A | 11/1994 | Culbertson |
| 5,443,843 | A | 8/1995 | Curatolo |
| 5,491,586 | A | 2/1996 | Phillips |
| 5,762,637 | A | 6/1998 | Berg et al. |
| 5,840,332 | A | 11/1998 | Lerner |
| 5,939,467 | A | 8/1999 | Wnuk et al. |
| 6,120,802 | A * | 9/2000 | Breitenbach ......... A61K 9/2095 424/464 |
| 6,120,803 | A | 9/2000 | Wong |

(Continued)

FOREIGN PATENT DOCUMENTS

| AU | 643219 B2 | 1/1991 |
| AU | 6199090 A | 3/1991 |

(Continued)

OTHER PUBLICATIONS

Javed, J. Drug Del. Sci. Tech., 24, 6, 2014 (Year: 2014).*
Kanis, Journal of Biomaterials Applications, 29, 5, 2014 (Year: 2014).*
Nakamichi, J Drug Del Sci Tech, 3, 14, 2004 (Year: 2004).*
"Guidance for Industry: Size, Shape, and Other Physical Attributes of Generic Tables and Capsules," (2013). Retrieved from www:v.regulations.gov/#!documentDetail;D-FDA-2013-N-1434-0002, last visited Dec. 2013, 11 pages.
"Q3C—Tables and List Guidance for Industy," (2017). Retrieved from www.fda.gov/downloads/drugs/guidances/ucm073395.pdf, last visited Jun. 2017, 10 pages.

(Continued)

Primary Examiner — Susan T Tran
Assistant Examiner — William Craigo
(74) Attorney, Agent, or Firm — MORRISON & FOERSTER LLP

(57) ABSTRACT

The invention provides gastric residence systems with specifically tailored architectures and methods for making such systems. The components of the gastric residence systems can be manufactured by three-dimensional printing or by co-extrusion. The ability to construct precise architectures for the systems provides excellent control over drug release, in vivo stability, and residence time of the systems.

34 Claims, 32 Drawing Sheets

(56) References Cited

U.S. PATENT DOCUMENTS

| | | | |
|---|---|---|---|
| RE37,314 E | 8/2001 | Hirai | |
| 6,306,420 B1 * | 10/2001 | Cheikh | A61K 9/0019 424/422 |
| 6,306,439 B1 | 10/2001 | Penners | |
| 6,316,460 B1 | 11/2001 | Creekmore | |
| 6,375,649 B1 | 4/2002 | Jellie | |
| 6,436,069 B1 | 8/2002 | Jellie | |
| 6,488,962 B1 | 12/2002 | Berner | |
| 6,500,168 B1 | 12/2002 | Jellie | |
| 6,548,083 B1 | 4/2003 | Wong | |
| 6,685,962 B2 | 2/2004 | Friedman | |
| 6,776,999 B1 | 8/2004 | Krumme | |
| 6,780,168 B2 | 8/2004 | Jellie | |
| 6,825,308 B1 | 11/2004 | Kulkarni | |
| 6,962,579 B2 | 11/2005 | Jellie | |
| 7,276,252 B2 | 10/2007 | Payumo | |
| 7,691,151 B2 | 4/2010 | Kutsko | |
| 7,964,196 B2 | 6/2011 | De Los Rios | |
| 8,021,384 B2 | 9/2011 | Weiss | |
| 8,038,659 B2 | 10/2011 | Boyden | |
| 8,158,143 B2 | 4/2012 | Lendlein | |
| 8,267,888 B2 | 9/2012 | Marco et al. | |
| 8,277,843 B2 | 10/2012 | Singh | |
| 8,298,574 B2 | 10/2012 | Tsabari | |
| 8,377,453 B2 | 2/2013 | Han | |
| 8,414,559 B2 | 4/2013 | Gross | |
| 8,586,083 B2 | 11/2013 | Mohammad | |
| 8,609,136 B2 | 12/2013 | Tsabari | |
| 8,753,678 B2 | 6/2014 | Tsabari | |
| 8,771,730 B2 | 7/2014 | Navon | |
| 9,072,663 B2 | 7/2015 | Navon | |
| 9,107,816 B2 | 8/2015 | Lee | |
| 9,220,688 B2 | 12/2015 | Alon | |
| 9,259,387 B2 | 2/2016 | Navon | |
| 10,182,985 B2 | 1/2019 | Bellinger | |
| 10,195,143 B2 | 2/2019 | Zalit et al. | |
| 10,485,758 B2 | 11/2019 | Menachem et al. | |
| 10,517,819 B2 | 12/2019 | Bellinger et al. | |
| 10,517,820 B2 | 12/2019 | Bellinger | |
| 10,532,027 B2 | 1/2020 | Bellinger | |
| 10,596,110 B2 | 3/2020 | Bellinger | |
| 10,610,482 B2 | 4/2020 | Bellinger | |
| 10,716,751 B2 | 7/2020 | Bellinger et al. | |
| 10,716,752 B2 | 7/2020 | Bellinger et al. | |
| 11,077,056 B2 | 8/2021 | Bellinger et al. | |
| 11,246,829 B2 | 2/2022 | Bellinger et al. | |
| 11,357,723 B2 | 6/2022 | Bellinger et al. | |
| 11,389,399 B2 | 7/2022 | Bellinger et al. | |
| 2002/0022048 A1 | 2/2002 | Bromberg | |
| 2002/0132008 A1 | 9/2002 | Mumper | |
| 2003/0021822 A1 | 1/2003 | Lloyd | |
| 2003/0232895 A1 | 12/2003 | Omidian | |
| 2004/0180086 A1 | 9/2004 | Ramtoola | |
| 2004/0219186 A1 | 11/2004 | Ayres | |
| 2005/0033331 A1 | 2/2005 | Burnett | |
| 2005/0165136 A1 | 7/2005 | Mays | |
| 2005/0175702 A1 | 8/2005 | Muller-Schulte | |
| 2005/0249807 A1 | 11/2005 | Brown et al. | |
| 2006/0069214 A1 | 3/2006 | Deiss | |
| 2006/0142794 A1 | 6/2006 | Lendlein | |
| 2006/0182788 A1 | 8/2006 | Singh | |
| 2007/0048383 A1 | 3/2007 | Helmus | |
| 2007/0104754 A1 | 5/2007 | Sterling | |
| 2007/0123809 A1 | 5/2007 | Weiss | |
| 2007/0129784 A1 | 6/2007 | Lendlein | |
| 2007/0131144 A1 | 6/2007 | Winter et al. | |
| 2007/0264307 A1 | 11/2007 | Chen | |
| 2008/0075766 A1 | 3/2008 | Li | |
| 2008/0153779 A1 | 6/2008 | Liao | |
| 2008/0241238 A1 | 10/2008 | Dharmadhikari | |
| 2008/0249156 A1 | 10/2008 | Palepu | |
| 2008/0260824 A1 | 10/2008 | Nangia | |
| 2008/0292691 A1 | 11/2008 | Lloyd | |
| 2009/0092415 A1 | 4/2009 | Murakami | |
| 2009/0105531 A1 | 4/2009 | Boyden | |
| 2009/0155326 A1 * | 6/2009 | Mack | A61K 31/4164 514/230.2 |
| 2009/0182424 A1 | 7/2009 | Marco | |
| 2009/0246142 A1 | 10/2009 | Bhatia | |
| 2009/0324694 A1 | 12/2009 | Mohammad | |
| 2010/0152410 A1 | 6/2010 | East | |
| 2010/0168439 A1 | 7/2010 | Olson | |
| 2010/0256342 A1 | 10/2010 | Salemme | |
| 2010/0266655 A1 | 10/2010 | Dadey | |
| 2010/0297009 A1 | 11/2010 | Olson | |
| 2010/0316712 A1 | 12/2010 | Nangla | |
| 2011/0038912 A1 | 2/2011 | Darby et al. | |
| 2011/0040318 A1 | 2/2011 | Marco | |
| 2011/0052700 A1 | 3/2011 | Han | |
| 2011/0097395 A1 | 4/2011 | Babul et al. | |
| 2011/0125091 A1 | 5/2011 | Abbate | |
| 2011/0245909 A1 * | 10/2011 | Schmid | A61F 2/92 623/1.16 |
| 2011/0268666 A1 | 11/2011 | Friedman | |
| 2011/0305685 A1 | 12/2011 | Tseng | |
| 2012/0009261 A1 | 1/2012 | Sesha | |
| 2012/0116285 A1 | 5/2012 | Duggirala | |
| 2012/0165793 A1 | 6/2012 | Ortiz | |
| 2012/0165794 A1 | 6/2012 | Ortiz | |
| 2012/0301547 A1 | 11/2012 | Gan | |
| 2012/0321706 A1 | 12/2012 | Masri | |
| 2013/0045530 A1 | 2/2013 | Gracias | |
| 2013/0131637 A1 | 5/2013 | Dicesare et al. | |
| 2013/0226104 A1 | 8/2013 | Hyde | |
| 2013/0273135 A1 | 10/2013 | Brooks | |
| 2014/0050784 A1 | 2/2014 | Kagan | |
| 2014/0052171 A1 | 2/2014 | Tegels | |
| 2014/0249499 A1 | 9/2014 | Selaru | |
| 2015/0265536 A1 | 9/2015 | Muley | |
| 2015/0335592 A1 | 11/2015 | Barnscheid | |
| 2015/0342877 A1 * | 12/2015 | Menachem | A61K 9/2054 424/472 |
| 2016/0317796 A1 | 11/2016 | Zhang | |
| 2017/0051099 A1 | 2/2017 | Diciccio | |
| 2017/0106099 A1 | 4/2017 | Bellinger | |
| 2017/0128576 A1 | 5/2017 | Zhang | |
| 2017/0135954 A1 | 5/2017 | Bellinger | |
| 2017/0266112 A1 | 9/2017 | Bellinger | |
| 2018/0250226 A1 | 9/2018 | Betser et al. | |
| 2018/0311154 A1 | 11/2018 | Kanasty | |
| 2018/0369138 A1 | 12/2018 | Zalit et al. | |
| 2019/0070107 A1 | 3/2019 | Bellinger | |
| 2019/0070108 A1 | 3/2019 | Bellinger | |
| 2019/0125667 A1 | 5/2019 | Bellinger | |
| 2019/0133936 A1 | 5/2019 | Bellinger | |
| 2019/0175500 A1 | 6/2019 | Bellinger | |
| 2019/0231697 A1 | 8/2019 | Bellinger | |
| 2019/0262265 A1 | 8/2019 | Bellinger | |
| 2019/0290799 A1 * | 9/2019 | Arshi | A61L 15/42 |
| 2019/0298652 A1 | 10/2019 | Bellinger et al. | |
| 2019/0365645 A1 | 12/2019 | Traverso et al. | |
| 2019/0365646 A1 | 12/2019 | Menachem et al. | |
| 2019/0366064 A1 | 12/2019 | Traverso et al. | |
| 2020/0030589 A1 | 1/2020 | Ben Menachem et al. | |
| 2020/0085736 A1 | 3/2020 | Bellinger et al. | |
| 2020/0085737 A1 | 3/2020 | Bellinger et al. | |
| 2020/0146979 A1 | 5/2020 | Kanasty | |
| 2020/0230244 A1 | 7/2020 | Traverso et al. | |
| 2020/0376242 A1 | 12/2020 | Ben Menachem et al. | |
| 2020/0405635 A1 | 12/2020 | Menachem et al. | |
| 2021/0093564 A1 | 4/2021 | Bellinger et al. | |
| 2021/0113460 A1 | 4/2021 | Bellinger et al. | |
| 2021/0128460 A1 | 5/2021 | Bellinger et al. | |
| 2021/0177750 A1 | 6/2021 | Bellinger et al. | |
| 2023/0039421 A1 | 2/2023 | Bellinger et al. | |

FOREIGN PATENT DOCUMENTS

| | | |
|---|---|---|
| CA | 2951884 A1 | 12/2015 |
| CN | 1049787 A | 3/1991 |
| CN | 1754898 A | 4/2006 |
| CN | 102245127 A | 11/2011 |
| CN | 103654903 A | 3/2014 |
| EP | 0202159 A2 | 11/1986 |

(56) References Cited

FOREIGN PATENT DOCUMENTS

| | | |
|---|---|---|
| EP | 0253554 A2 | 1/1988 |
| EP | 0253554 A3 | 7/1988 |
| EP | 0344939 A2 | 12/1989 |
| EP | 0388234 A1 | 9/1990 |
| EP | 0406015 A1 | 1/1991 |
| EP | 0415671 A2 | 3/1991 |
| EP | 0202159 B1 | 7/1991 |
| EP | 0344939 B1 | 1/1993 |
| EP | 0820258 B1 | 10/2002 |
| EP | 1124534 B1 | 1/2004 |
| EP | 1687379 A1 | 8/2006 |
| EP | 1911518 A1 | 4/2008 |
| EP | 2324822 A2 | 5/2011 |
| EP | 2329810 A1 | 6/2011 |
| EP | 1528916 B1 | 12/2012 |
| JP | S58174312 A | 10/1983 |
| JP | 6226215 A | 2/1987 |
| JP | 6323815 A | 8/1987 |
| JP | 0229268 A | 11/1989 |
| JP | H03044318 A | 2/1991 |
| JP | 03128934 A | 5/1991 |
| JP | 03163011 A | 7/1991 |
| JP | 2006518392 A | 8/2006 |
| JP | 2013500293 A | 1/2013 |
| JP | 2013530193 A | 7/2013 |
| JP | 2004325508 A | 11/2018 |
| RU | 2070029 C1 | 12/1996 |
| RU | 2242219 C2 | 12/2004 |
| WO | 199738969 A1 | 10/1997 |
| WO | WO200025742 A1 | 5/2000 |
| WO | WO200137812 A2 | 5/2001 |
| WO | WO200137812 A3 | 2/2002 |
| WO | WO2003015745 A1 | 2/2003 |
| WO | WO2004010978 A1 | 2/2004 |
| WO | WO2004073690 A1 | 9/2004 |
| WO | WO2004112755 A1 | 12/2004 |
| WO | 2005042642 A1 | 5/2005 |
| WO | 2005065660 A2 | 7/2005 |
| WO | WO2006072948 A2 | 7/2006 |
| WO | WO2006084164 A2 | 8/2006 |
| WO | WO2006072948 A3 | 11/2006 |
| WO | WO2006084164 A3 | 11/2006 |
| WO | WO2007027812 A2 | 3/2007 |
| WO | WO2007048223 A2 | 5/2007 |
| WO | 2005065660 A3 | 6/2007 |
| WO | WO2007048223 A3 | 6/2007 |
| WO | WO2007083309 A2 | 7/2007 |
| WO | WO2007093999 A1 | 8/2007 |
| WO | WO2007083309 A3 | 9/2007 |
| WO | WO2008015162 A1 | 2/2008 |
| WO | 2008039698 A1 | 4/2008 |
| WO | WO2008140651 A2 | 11/2008 |
| WO | WO2008140651 A3 | 1/2009 |
| WO | WO2007027812 A3 | 4/2009 |
| WO | 2009132461 A1 | 11/2009 |
| WO | WO2009144558 A1 | 12/2009 |
| WO | 2010042879 A2 | 4/2010 |
| WO | WO2010035273 A2 | 4/2010 |
| WO | 2010042879 A3 | 6/2010 |
| WO | WO2010064100 A1 | 6/2010 |
| WO | WO2010064139 A2 | 6/2010 |
| WO | WO2010035273 A3 | 7/2010 |
| WO | 2010099466 A2 | 9/2010 |
| WO | WO2010064139 A3 | 9/2010 |
| WO | 2010099466 A3 | 1/2011 |
| WO | 2011012369 A2 | 2/2011 |
| WO | WO2011032087 A2 | 3/2011 |
| WO | WO2011032087 A3 | 6/2011 |
| WO | 2011012369 A3 | 9/2011 |
| WO | 2011139796 A2 | 11/2011 |
| WO | 2012003968 A1 | 1/2012 |
| WO | 2011139796 A3 | 3/2012 |
| WO | WO2012087658 A1 | 6/2012 |
| WO | 2013011438 A1 | 1/2013 |
| WO | 2013049188 A1 | 4/2013 |
| WO | WO2014014348 A1 | 1/2014 |
| WO | WO2015083171 A1 | 6/2015 |
| WO | 2015187746 A1 | 12/2015 |
| WO | 2015191922 A1 | 12/2015 |
| WO | WO-2015191920 A1 * | 12/2015 ......... A61K 47/6901 |
| WO | WO2015191925 A1 | 12/2015 |
| WO | WO2017070612 A1 | 4/2017 |
| WO | WO2017100367 A1 | 6/2017 |
| WO | WO2018064630 A1 | 4/2018 |
| WO | WO2018227147 A1 | 12/2018 |
| WO | WO2019060458 A1 | 3/2019 |
| WO | 2019111132 A1 | 6/2019 |
| WO | 2020102650 A2 | 5/2020 |
| WO | 2020102650 A3 | 8/2020 |

OTHER PUBLICATIONS

Agrawal, A. et al. (Jul. 2006). "Clinical Relevance of the Nutcracker Esophagus: Suggested Revision of Criteria for Diagnosis," J Clin Gastroenterol. 40(6):504-509.

Ajili, S.H. et al. (Jun. 2009, e-pub. Jan. 3, 2009). "Polyurethane/Polycaprolactane Blend With Shape Memory Effect as a Proposed Material for Cardiovascular Implants," Acta Biomaterialia 5(5):1519-1530.

Alhnan, M.A. et al. (Aug. 2016; e-published on May 18, 2016). "Emergence of 3D Printed Dosage Forms: Opportunities and Challenges," Pharm. Res. 33(8):1817-1832, 38 pages.

Belknap, R. et al. (Jan. 7, 2013). "Feasibility of an Ingestible Sensor-Based System for Monitoring Adherence to Tuberculosis Therapy," Plos One 8(1):e53373, pp. 1-5.

Bellinger, A.M et al. (Nov. 16, 2016). "Oral, Ultra-Long-Lasting Drug Delivery: Application Toward Malaria Elimination Goals," Sci. Transl. Med. 8(365ra157): 1-12., (with Supplementary Material), 21 pages.

Byrne, C. et al. (Mar. 2007; e-pub. Dec. 18, 2006). "The Ingestible Telemetric Body Core Temperature Sensor. A Review of Validity and Exercise Applications," Brit J Sport Med. 41(3):126-133.

Cargill, R. et al. (Aug. 1988). "Controlled Gastric Emptying. 1. Effects of Physical Properties on Gastric Residence Times of Nondisintegrating Geometric Shapes in Beagle Dogs," Pharm Res. 5(8):533-536.

Cargill, R. et al. (Jun. 1989). "Controlled Gastric Emptying. II. In Vitro Erosion and Gastric Residence Times of an Erodible Device in Beagle Dogs," Pharm. Res. 6(6):506-509.

Choudhry, N.K. et al. (Dec. 1, 2011; e-pub. Nov. 14, 2011). "Full Coverage for Preventive Medications After Myocardial Infarction," N Engl J Med. 365:2088-2097.

Cirillo, G. et al. (Jan. 21, 2014). "Carbon Nanotubes Hybrid Hydrogels in Drug Delivery: A Perspective Review," BioMed Res Intl. 2014(Article ID 825017), 17 pages.

Dash, S. et al. (May-Jun. 2010). "Kinetic Modeling on Drug Release From Controlled Drug Delivery Systems," Acta Poloniae Pharmaceutica 67(3):217-223.

Davies, G.C. et al. (Mar. 1993). "Release Characteristics, Ovarian Activity and Menstrual Bleeding Pattern with a Single Contraceptive Implant Releasing 3-Ketodesogestrel," Contraception 47(3):251-261.

Edwards, D.A.W. (Nov. 1961). "Physiological Concepts of the Pylorus," Proceedings of the Royal Society of Medicine 54:930-933.

Ereqat, S. et al. (Sep. 2011). "MDR Tuberculosis and Non-Compliance With Therapy," Lancet Infect Dis. 11(9):662.

European Extended Search Report mailed on Jul. 5, 2019, for Application No. EP 16873798.9, filed on Apr. 26, 2018, 9 pages.

European Search Report mailed on May 27, 2019 for Application No. EP 16858392.0, filed on Apr. 26, 2018, 10 pages.

Extended European Search Report mailed on Dec. 20, 2017 for Application No. EP 15806017.8, filed on Apr. 26, 2018, 10 pages.

Extended European Search Report mailed on Nov. 20, 2019 for Application No. EP 17803732.1, 9 pages.

Fallon, S.C. et al. (Apr. 2013). "The Surgical Management of Rapunzel Syndrome: A Case Series and Literature Review," J Pediatr Surg. 48(4):830-834.

(56) References Cited

OTHER PUBLICATIONS

Farra, R. et al. (Feb. 22, 2012; e-pub Feb. 16, 2012.). "First-In-Human Testing of a Wirelessly Controlled Drug Delivery Microchip," Sci Transl Med. 4(122):122ra21, 12 pages.
Fix, J.A. et al. (1993). "Controlled Gastric Emptying. III. Gastric Residence Time of a Nondisintegrating Geometric Shape in Human Volunteers," Pharm. Res. 10(7):1087-1089.
Fuhrmann, G. et al. (Jul. 2013). "Sustained Gastrointestinal Activity of Dendronized Polymer-Enzyme Conjugates," Nat Chem. 5:582-589.
Genco, A. et al. (2005). "Bioenterics Intragastric Balloon: The Italian Experience With 2,515 Patients," Obes Surg. 15:1161-1164.
Gordi, T. et al. (May 2008). "Pharmacokinetics of Gabapentin After a Single Day and at Steady State Following the Administration of Gastric-Retentive-Extended-Release and Immediate-Release Tablets: A Randomized, Open-Label, Multiple-Dose, Three-Way Crossover, Exploratory Study in Healthy Subjects," Clin Ther. 30(5):909-916.
Haslauer, C.M. et al. (Jul. 2015; e-published on Sep. 17, 2014). "Translating Textiles to Tissue Engineering: Creation and Evaluation of Microporous, Biocompatible, Degradable Scaffolds Using Industry Relevant Manufacturing Approaches and Human Adipose Derived Stem Cells," J. Biomed. Mater. Res. B Appl. Biomater. 103(5):1050-1058, 22 pages.
Hiemke, C. et al. (Sep. 2011; e-published on Sep. 27, 2011). "AGNP Consensus Guidelines for Therapeutic Drug Monitoring in Psychiatry: Update 2011," Pharmacopsychiatry 44(6):195-235.
Huang, W.M. et al. (Jul.-Aug. 2010). "Shape Memory Materials," Materials Today 13(7-8):54-61.
Hwang, S.-J et al. (1998). "Gastric Retentive Drug-Delivery Systems," Crit Rev Ther Drug Carrier Syst. 15(3):243-284.
International Preliminary Report on Patentability issued on Dec. 10, 2019 for PCT Application No. PCT/US2018/036743 filed on Jun. 8, 2018, 16 pages.
International Preliminary Report on Patentability mailed on Apr. 11, 2019 for PCT Application No. PCT/US2017/054608 filed on Sep. 29, 2017, 16 pages.
International Preliminary Report on Patentability mailed on Dec. 6, 2018 for PCT Application No. PCT/US2017/034856, filed on May 26, 2017, 11 pages.
International Preliminary Report on Patentability mailed on Dec. 22, 2016 for PCT Application No. PCT/US2015/035423 filed on Jun. 11, 2015, 11 pages.
International Preliminary Report on Patentability mailed on Jun. 21, 2018 for PCT Application No. PCT/US2016/065453 filed on Dec. 7, 2016, 11 pages.
International Preliminary Report on Patentability mailed on May 3, 2018 for PCT Application No. PCT/US2016/058309 filed on Oct. 21, 2016, 6 pages.
International Preliminary Report on Patentability mailed on Nov. 16, 2017 for PCT Application No. PCT/US2016/030020 filed on Apr. 29, 2016, 8 pages.
International Search Report and Written Opinion mailed on Dec. 14, 2017 for PCT Application No. PCT/US2017/054608 filed on Sep. 29, 2017, 18 pages.
International Search Report and Written Opinion mailed on Dec. 29, 2016 for PCT Application No. PCT/US2016/058309 filed on Oct. 21, 2016, 8 pages.
International Search Report and Written Opinion mailed on Feb. 28, 2017 for PCT Application No. PCT/US2016/065453 filed on Dec. 7, 2016, 14 pages.
International Search Report and Written Opinion mailed on Jul. 21, 2016 for PCT Application No. PCT/US2016/030020 filed on Apr. 29, 2016, 10 pages.
International Search Report and Written Opinion mailed on Nov. 13, 2017 for PCT Application No. PCT/US2017/034856, filed on May 26, 2017, 15 pages.
International Search Report and Written Opinion mailed on Sep. 10, 2018 for PCT Application No. PCT/US2018/036743 filed on Jun. 8, 2018, 26 pages.
International Search Report and Written Opinion mailed on Sep. 15, 2015 for PCT Application No. PCT/US2015/035423 filed on Jun. 11, 2015, 13 pages.
Invitation to Pay Additional Fees and, Where Applicable, Protest Fee, mailed on Sep. 5, 2017, for PCT Application No. PCT/US2017/034856, filed on May 26, 2017, 3 pages.
Jantratid, E. et al. (Jul. 2008; e-pub. Apr. 11, 2008). "Dissolution Media Simulating Conditions in the Proximal Human Gastrointestinal Tract: An Update," Pharm. Res. 25(7):1663-1676.
Karim, Q.A. et al. (Sep. 3, 2010, e-pub. Jul. 19, 2010). "Effectiveness and Safety Of Tenofovir Gel, an Antiretroviral Microbicide, for the Prevention of HIV Infection in Women," Science 329(5996):1168-1174, 19 pages.
Kethu, S.R. et al. (2012). "Endoluminal Bariatric Techniques," Gastrointestinal Endoscopy 76(1):1-7.
Khaled, S.A. et al. (Jan. 30, 2014). "Desktop 3D Printing of Controlled Release Pharmaceutical Bilayer Tablets," International Journal of Pharmaceutics 461(1-2):105-111, 17 pages.
Kim, B.K. et al. (1996). "Polyurethanes Having Shape Memory Effects," Polymer 37(26):5781-5793.
Kim, Y.J. et al. (Dec. 24, 2013). "Biologically Derived Melanin Electrodes in Aqueous Sodium-Ion Energy Storage Devices," P Natl Acad Sci USA. 110(52): 20912-20917.
Lam, P.L. et al. (2014). "Advanced Progress of Microencapsulation Technologies: In Vivo and In Vitro Models for Studying Oral and Transdermal Drug Deliveries," J. Control Release 178:25-45.
Laulicht, B. et al. (Feb. 8, 2011). "Localization of Magnetic Pills," Proc Natl Acad Sci. 108(6):2252-2257.
Li, L.C. et al. (Oct. 16, 2002). "Polyanhydride Implant for Antibiotic Delivery—From the Bench to the Clinic," Adv Drug Deliv Rev. 54(7):963-986.
Lipton, S.A. (Jan. 2004). "Failures and Successes of NMDA Receptor Antagonists: Molecular Basis For the Use of Open-Channel Blockers Like Memantine in the Treatment of Acute and Chronic Neurologic Insults," NeuroRx: The Journal of the American Society for experimental Neuro Therapeutics 1(1): 101-110.
Liu, Y. et al. (2009; e-pub. Aug. 29, 2008). "Review of Electro-Active Shape-Memory Polymer Composite," Compos Sci and Technol. 69(13):2064-2068.
López-Pousa, S. et al. (Sep. 2012). "Consumption of Pharmaceuticals in Primary Non-Alzheimer's Degenerative Dementias: A Cross-Sectional Study By the Registry of Dementias of Girona (ReDeGi)," Drugs Aging 29 (9):733-740, 22 pages.
Marrazzo, J.M. et al. (Feb. 5, 2015). "Tenofovir-Based Preexposure Prophylaxis for HIV Infection Among African Women," N Engl J Med. 372(6):509-518.
Meng, Q. et al. (2009). "A Review of Shape Memory Polymer Composites and Blends," Composites Part A: Applied Science and Manufacturing 40(11):1661-1672.
Mintchev, M.P. et al. (Feb. 2010; e-pub Dec. 11, 2009). "Pilot Study of Temporary Controllable Gastric Pseudobezoars for Dynamic Non-Invasive Gastric Volume Reduction," Physiol Meas. 31(2):131-144.
Moes, A.J. (Jan. 1993). "Gastroretentive Dosage Forms," Crit Rev Ther Drug Carrier Syst. 10(2):143-195.
Mohr, R. et al. (Mar. 7, 2006; e-pub Feb. 28, 2006.). "Initiation of Shape-Memory Effect by Inductive Heating of Magnetic Nanoparticles in Thermoplastic Polymers," Proc Natl Acad Sci USA. 103(10):3540-3545.
Olson, A.J. et al. (Dec. 26, 2007; e-pub Dec. 18, 2007). "Chemical Mimicry of Viral Capsid Self-Assembly," Proc Natl Acad Sci USA 104(52):20731-20736.
Osterberg, L. et al. (Aug. 4, 2005). "Adherence to Medication," N Engl J Med. 353(5):487-497.
Phadke, A. et al. (Mar. 20, 2012; e-pub Mar. 5, 2012). "Rapid Self-Healing Hydrogels," Proc Natl Acad Sci USA 109(12):4383-4388.
Phillips, M.R. et al. (Jul. 1998). "Gastric Trichobezoar: Case Report and Literature Review," Mayo Clin Proc. 73(7):653-656.
Pittenger, C. (Jun. 2015; e-published on Jun. 11, 2015). "Glutamate Modulators in the Treatment of Obsessive-Compulsive Disorder," Psychiatr. Ann. 45(6):308-315, 13 pages.

(56) References Cited

OTHER PUBLICATIONS

Puso, M. A. et al. (Jan. 1, 2006). "A Stabilized Nodally Integrated Tetrahedral," International Journal for Numerical Methods in Engineering 67(6):841-867.
Rammes, G. et al. (Mar. 2008). "Pharmacodynamics of Memantine: An Update," Curr. Neuropharmacol. 6(1):55-78.
Richter, J.E. et al. (Jun. 1987). "Esophageal Manometry in 95 Healthy Adult Volunteers. Variability of Pressures With Age and Frequency of "Abnormal" Contractions," Dig Dis Sci. 32(6):583-592.
Salessiotis, N. (Sep. 1972). "Measurement of the Diameter of the Pylorus in Man: Part I. Experimental Project for Clinical Application," The Amer J of Surgery. 124:331-333.
Salunke, D.M. et al. (Sep. 12, 1986). "Self-Assembly of Purified Polyomavirus Capsid Protein VP1," Cell 46 (6):895-904, 10 pages.
Singer, S.J. et al. (Feb. 18, 1972). "The Fluid Mosaic Model of the Structure of Cell Membranes," Science 175 (4023):720-731.
Singh, B.N. et al. (Feb. 3, 2000). "Floating Drug Delivery Systems: An Approach to Oral Controlled Drug Delivery Via Gastric Retention," J Control Release 63(3):235-259.
Szakács, R. et al. (2012). "The "Blue" Side of Glutamatergic Neurotransmission: NMDA Receptor Antagonists as Possible Novel Therapeutics for Major Depression," Neuropsychopharmacol. Hung. 14(1):29-40.
Tao, H. et al. (Feb. 21, 2012). "Silk-Based Conformal, Adhesive, Edible Food Sensors," Adv Mater. 24 (8):1067-1072.
Timmer, C.J. et al. (Sep. 2000). "Pharmacokinetics of Etonogestrel and Ethinylestradiol Released From a Combined Contraceptive Vaginal Ring," Clin Pharmacokinet. 39(3):233-242.
Traverso, G. et al. (Mar. 26, 2015). "Special Delivery for the Gut," Nature. 519:S19.
Uhrich, K.E. et al. (1999, e-pub. Oct. 26, 1999). "Polyermic Systems for Controlled Drug Relase," Chem. Rev. 99:3181-3198.
Ursan, I.D. et al. (Mar.-Apr. 2013). "Three-Dimensional Drug Printing: A Structured Review," J. Am. Pharm. Assoc. 53(2):136-144.
Whitesides, G.M. et al. (Mar. 29, 2002). "Self-Assembly at all Scales," Science 295(5564):2418-2421.
Wilber, A.W. et al. (Nov. 7, 2009). "Self-Assembly of Monodisperse Clusters: Dependence on Target Geometry," J Chem Phys. 131(17):175101, 14 pages.
Wilber, A.W et al. (Nov. 7, 2009; e-pub. Nov. 2, 2009). "Monodisperse Self-Assembly in a Model With Protein-Like Interactions," J Chem Phys. 131(17):175102, 11 pages.
Won, Y.W. et al. (Dec. 2014). "Oligopeptide Complex for Targeted Non-Viral Gene Delivery to Adipocytes," Nat Mater. 13:1157-1164.
Yu, D.G. et al. (Sep. 2008). "Three-Dimensional Printing in Pharmaceutics: Promises and Problems," J. Pharm. Sci. 97(9):3666-3690.
Zhang, S. et al. (Oct. 2015; e-pub. Jul. 27, 2015). "A Ph-Responsive Supramolecular Polymer Gel as an Enteric Elastomer for Use in Gastric Devices," Nature Materials 14(10):1065-1071, 19 pages.
Zhang, X. et al. (2013; e-pub Oct. 15, 2012). "Biodegradable Shape Memory Nanocomposites With Thermal and Magnetic Field Responsiveness," J Biomater Sci Polym Ed. 24(9):1057-1070.
Barbucci, R. et al. (1989). "Vinyl Polymers Containing Amido and Carboxyl Groups as Side Substituents, 2 a). Thermodynamic and Fourier-Transform Infrared Spectroscopic Studies for the Protonation of poly(N-Acryloylglycine) and the poly(N-N-acryoyl-6-aminocaproic acid)," Makromol. Chem. 190:2627-2638.
Cong, H.-P et al. (2013, e-pub. Jul. 23, 2013). "Stretchable and Self-Healing Graphene Oxide-Polymer Composite Hydrogels: A Dual-Network Design," Chem Mater. 25:3357-3362.
Dumortier, G. et al. (Dec. 2006, e-pub. Nov. 11, 2006). "A Review of Poloxamer 407 Pharmaceutical and Pharmacological Characteristics," Pharmaceutical Research 23(12):2709-2728.
Dunn, D.L. et al. (2005). Wound Closure Manual Ethicon, Inc. A Johnson and Johnson company, 127 pages.
Evonik Industries AG, (Dec. 2012). Eudragit Technical Information Sheet, Eudragit L 100 and Eudragit S 100, Specification and Test Methods, 7 pages.
Extended European Search Report mailed Feb. 23, 2018 for Application No. EP 15806483.2, filed Jun. 11, 2015, 8 pages.
Harrison, S.K. et al. (2006). "Comparison of Shear Modulus Test Methods," Virginia Tech. 8 pages.
International Preliminary Report on Patentability for PCT/US2015/035425 issued Dec. 15, 2016, filed Jun. 11, 2015, 6 pages.
International Preliminary Report on Patentability for PCT/US2015/035429 issued Dec. 15, 2016, filed Jun. 11, 2015, 8 pages.
International Search Report and Written Opinion for PCT/US2015/035425 mailed Sep. 15, 2015, filed Jun. 11, 2015, 8 pages.
International Search Report and Written Opinion for PCT/US2015/035429 mailed Sep. 15, 2015, filed Jun. 11, 2015, 9 pages.
Kao, E.C. et al. (Jan. 1996). "Preparation of Glass Ionomer Cement Using N-acryloyl Substituted Amino Acid Monomers-Evaluationof Physical Properties," Dent Mater. 12:44-51.
Khanna, S.C. et al. (Sep. 1969). "Epoxy Resin Beads as a Pharmaceutical Dosage Form. I.: Method of Preparation," Journal of Pharmaceutical Sciences 58(9):1114-1117.
Miao, L. et al. (2015). "Exploring the Tumor Microenvironment With Nanoparticles," Cancer Treat Res. 166:193-226, 36 pages.
Muthu, M.S. et al. (2008). "Studies on Biodegradable Polymeric Nanoparticles of Risperidone: in vitro and in vivo Evaluation," Nanomedicine 3(3):305-319.
Neto-Ferreira, R. et al. (2013). "Pleiotropic Effects of Rosuvastatin on the Glucose Metabolism and the Subcutaneous and Visceral Adipose Tissue Behavior in C57Bl/6 Mice," Diabetology Metabol Synd. 5:32, 10 pages.
Ren, S. et al. (2009). "Noncovalently Connected Micelles Based on a β-cyclodextrin-Contaling Polymer and Adamantane End-Capped Poly(e-ecaprolactone) via Host—Guest Interactions," J Polym Sci. 47:4267-4278.
Singh, P. et al. (2015, e-pub, Dec. 18, 2014). "Synthesis and Characterization of Nano Micelles of poly(N-acrylamidohexanoic acid)-b-poly(N-vinylcaprolactam) Via RAFT Process: Solubilizing and Releasing of Hydrophobic Molecules," Polymer. 57:51-61.
Six-Pentagons (Dec. 23, 2017). "Six-Pentagons Polylink," retreived from http://makingmathvisible.com/polylinks/polylinks-3.html, lasted visited Dec. 23, 2017, 4 pages.
Yerragunta, B. et al. (Jan.-Mar. 2015). "Development of a Novel 3-Month Drug Releasing Risperidone Microspheres," J. Pharm Bioall Sci. 7(1):37-44.
Zu, Y. et al. (2008, e-pub. Sep. 26, 2008). "Effect of Neutralization of poly(methacrylic acid-co-ethyl acrylate) on Drug Release from Enteric-Coated Pellets Upon Accelerated Storage," Drug Dev. Ind. Pharm. 33(4):457-473.
Murphy, C.S. et al. (Oct. 2009). "Gastro-Retentive Drug Delivery Systems: Current Developments in Novel System Design and Evaluation," Curr. Drug Deliv. 6(5):451-460.
Welding Techniques for Thermoplastics (2021). retrieved from the Internet: URL:https://www.twi-global.com/technical-knowledge/job-knowledge/welding-techniques-forthermoplastics-055 (http://web.archive.org/web/20150416235739/ http://www.twiglobal.com/technical-knowledge/job-knowledge/welding-techniques-for-thermoplastics-055/, last visited Mar. 17, 2021, 8 pages.
Yang X, et al. (May 14, 2014), e-pub. May 5, 2014). "Triple Shape Memory Effect of Star-Shaped Polyurethane," ACS Appl Mater Interfaces 6(9):6545-6554.
Abraham, N. (May 15, 2015). "Dow Corning QP1-2 Liquid Silicone Rubber Supports Cost-Effective Medical Device Designs," Medical Design & Outsourcing, retrieved from the Internet https://www.medicaldesignandoutscourcing.com/dow-coming-qp1-2-liquid-silicone-rubber-supports-cost-effective-medical-device-designs/, last visited Nov. 16, 2021, 8 pages.
Chourasia, M.K. et al. (2003). "Pharmaceutical Approaches to Colon Targeted Drug Delivery Systems," J. Pharm. Pharmaceut Sci. 6(1):33-66.
Extended European Search Report mailed on Jun. 4, 2021 for Application No. EP 18813515.6, 8 pages.

(56) References Cited

OTHER PUBLICATIONS

Woodruff, M.A. et al. (Apr. 2010, e-pub. Apr. 7, 2010). "The Return of a Forgotten Polymer—Polycaprolactone in the 21st Century," Progress in Polymer Science 35:1217-1256.
Non-Final Office Action, dated Aug. 24, 2023, for U.S. Appl. No. 17/836,972, filed Jun. 9, 2022, 26 pages.
U.S. Appl. No. 18/272,786, filed Jan. 19, 2022 by Kanasty, et al. (Copy not submitted herewith pursuant to the waiver of 37 C.F.R. § 1.98(a)(2)(iii) issued by the Office on Sep. 21, 2004).

* cited by examiner

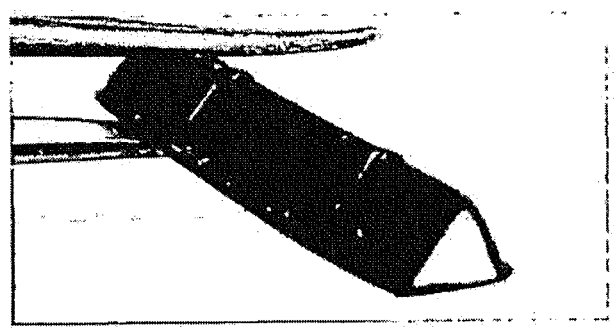

FIG. 11C

| Pre-incubation: Spine reinforced architecture |||
|---|---|---|
| Formulation | % Drug Load | 4-pt Bending Max Force |
| Non-reinforced | 38 | 77.9±7 |
| Reinforced | 38 | 130.4±12 |

| Pre-Incubation: Exoskeleton reinforced architecture |||
|---|---|---|
| Formulation | % Drug Load | 4-pt Bending Max Force |
| Non-reinforced | 38 | 90.5±2 |
| Reinforced | 38 | 152.7±7.6 |

| Post-incubation: Spine reinforced architecture |||
|---|---|---|
| Formulation | % Drug Load | 4-pt Bending Max Force |
| Non-reinforced | 38 | 26.2±2.1 |
| Reinforced | 38 | 80.2±4.2 |

| Post-incubation: Exoskeleton reinforced architecture |||
|---|---|---|
| Formulation | % Drug Load | 4-pt Bending Max Force |
| Non-reinforced | 38 | 33±0.4 |
| Reinforced | 38 | 155.5±14.6 |

FIG. 11D

| #Day incubation in FaSSGF | %Co-extruded sample torn | | %Welded sample torn | |
| --- | --- | --- | --- | --- |
| | in linker | at weld | in linker | at weld |
| 1 | 100 | 0 | 0 | 80 |
| 4 | 80 | 0 | 0 | 100 |
| 7 | 100 | 0 | 0 | 100 |

FIG. 13

MATERIALS ARCHITECTURE FOR GASTRIC RESIDENCE SYSTEMS

CROSS REFERENCE TO RELATED APPLICATIONS

This application is a national stage application under 35 U.S.C. § 371 of International Application No. PCT/US2017/034856 having an International Filing Date of May 26, 2017 which claims priority benefit of U.S. Provisional Patent Application No. 62/342,798 filed May 27, 2016. The entire contents of these applications are hereby incorporated herein by reference.

FIELD OF THE INVENTION

The invention relates to systems which remain in the stomach for extended periods for sustained release of pharmaceuticals, and methods of use thereof.

BACKGROUND OF THE INVENTION

Gastric residence systems are delivery systems for therapeutic agents which remain in the stomach for days to weeks, or even over longer periods, during which time drugs or other agents can elute from the systems for absorption in the gastrointestinal tract. Examples of such systems are described in International Patent Application Nos. WO 2015/191920 and WO 2015/191925.

Gastric residence systems are designed to be administered to the stomach of a patient, typically in a capsule which is swallowed or introduced into the stomach by an alternate method of administration (for example, feeding tube or gastric tube). Upon dissolution of the capsule in the stomach, the systems expand or unfold to a size which remains in the stomach and resists passage through the pyloric sphincter over the desired residence period (such as three days, seven days, two weeks, etc.). This requires mechanical stability over the desired residence period. Over the period of residence, the system releases an agent or agents, such as one or more drugs, preferably with minimal burst release, which requires careful selection of the carrier material for the agent in order to provide the desired release profile. While resident in the stomach, the system should not interfere with the normal passage of food or other gastric contents. The system should pass out of the stomach at the end of the desired residence time, and be readily eliminated from the patient. If the system prematurely passes from the stomach into the small intestine, it should not cause intestinal obstruction, and again should be readily eliminated from the patient. These characteristics require careful selection of the materials from which the system is constructed, and the dimensions and arrangement of the system.

The current invention describes advancements in design and manufacture of gastric residence systems, which permit sophisticated tailoring of the materials used in the systems, and the system architecture.

SUMMARY OF THE INVENTION

The invention provides gastric residence systems with precisely tailored materials architecture. The gastric residence systems can be administered to the stomach of a patient, for sustained release of an agent or drug. The customized architecture of the materials used in the systems allows excellent control over system performance, including drug or agent release in the stomach, system stability, system safety, and residence time in the gastrointestinal tract. Methods of making and using such gastric residence systems are also provided.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein the segments are attached together via linker regions having an outer surface; wherein at least one of the linker regions comprises a first linker material and a second linker material, where i) the second linker material extends from the outer surface of the at least one linker region into the bulk of the at least one linker region; or ii) the second linker material extends from the outer surface of the at least one linker region through the bulk of the at least one linker region and re-emerges on the outer surface; or iii) portions of the second linker material extend from the outer surface of the at least one linker region into the bulk of the at least one linker region, and portions of the second linker material extend from the outer surface of the at least one linker region through the bulk of the at least one linker region and re-emerge on the outer surface.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein the segments are attached together via a linker region; and wherein at least one segment further comprises a segment island material, where i) the segment island material extends from the outer surface of the at least one carrier polymer-agent segment into the bulk of the at least one carrier polymer-agent segment; or ii) the segment island material extends from the outer surface of the at least one carrier polymer-agent segment through the bulk of the at least one carrier polymer-agent segment and re-emerges on the outer surface; or iii) portions of the segment island material extend from the outer surface of the at least one carrier polymer-agent segment into the bulk of the at least one carrier polymer-agent segment, and portions of the segment island material extend from the outer surface of the at least one carrier polymer-agent segment through the bulk of the at least one carrier polymer-agent segment and re-emerges on the outer surface.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein at least one segment further comprises a reinforcing material, where the reinforcing material extends axially along the interior of the at least one segment; and wherein the segments are attached together via a linker region. In some embodiments, the reinforcing material extends axially along the interior of the at least one segment for at least about 90% of the length of the segment. In some embodiments, the reinforcing material has a cylindrical, triangular prism, rectangular prism, or square prism configuration. In some embodiments, the reinforcing material has a pie-shaped configuration (a configuration of a triangle with one side replaced by an arc of a circle). In some embodiments, the reinforcing material has an I-beam configuration or an H-beam configuration. In some embodiments, the reinforcing material has a truss configuration.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein one or more of the elongate members further comprise a fenestrated coating on the outer surface; and wherein the segments are attached together via a linker region.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein the segments are attached together via a linker region having an outer surface; wherein the segments of the elongate members have a lamellar configuration comprising at least two layers.

In some embodiments, the invention embraces a gastric residence system for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein each elongate member is comprised of at least two segments, each segment comprising a proximal end, a distal end, and an outer surface therebetween; wherein the segments are attached together via linker regions having an outer surface; wherein a portion of the linker regions extends into the segments, or wherein a portion of the segments extends into the linker regions, or both a portion of the linker regions extends into the segments and a portion of the segments extends into the linker regions.

In some embodiments, the invention embraces a method of manufacturing an elongate member for use in a gastric residence system, comprising co-extruding the elongate member. Co-extruding the elongate member can comprise co-extruding at least two regions comprising a carrier polymer-agent blend, wherein each region of carrier polymer-agent blend is separated from an adjacent region of carrier polymer-agent blend by a linker region. The linker region can comprise a material selected from the group consisting of an enteric linker and a time-dependent linker. In some embodiments, at least one junction between a carrier polymer-agent region and a linker region is co-extruded in an interlocking configuration. In some embodiments, at least one carrier polymer-agent region is co-extruded in an islands-in-the-sea configuration. In some embodiments, at least one linker region is co-extruded in an islands-in-the-sea configuration. In some embodiments, the island components of the islands-in-the-sea configuration can comprise at least one material selected from the group consisting of an enteric polymer and a time-dependent polymer.

In some embodiments, the invention embraces a method of manufacturing an elongate member for use in a gastric residence system, comprising printing the elongate member by additive manufacturing (for example, three-dimensional printing). The printing of the elongate member by three-dimensional printing can comprises printing at least two regions comprising a carrier polymer-agent blend, wherein each region of carrier polymer-agent blend is separated from an adjacent region of carrier polymer-agent blend by a linker region. The linker region can comprise a material selected from the group consisting of an enteric linker and a time-dependent linker. In some embodiments, at least one junction between a carrier polymer-agent region and a linker region can be printed in an interlocking configuration. In some embodiments, at least one carrier polymer-agent region can be printed in an islands-in-the-sea configuration. In some embodiments, at least one linker region can be printed in an islands-in-the-sea configuration. The island components of the islands-in-the-sea configuration can comprise at least one material selected from the group consisting of an enteric polymer and a time-dependent polymer.

In any of the methods for co-extrusion or three-dimensional printing disclosed herein, the carrier polymer of the carrier polymer-agent blend can be selected from the group consisting of polycaprolactone and polydioxanone.

In any of the methods for co-extrusion or three-dimensional printing disclosed herein, the agent of the carrier polymer-agent blend can be selected from the group consisting of analgesics; anti-analgesics; anti-inflammatory drugs; antipyretics; antidepressants; antiepileptics; antipsychotic agents; neuroprotective agents; anti-proliferatives; anti-cancer agents; antihistamines; antimigraine drugs; hormones; prostaglandins; antimicrobials; antibiotics; antifungals; antivirals; antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; antimalarial drug; quinine; lumefantrine; chloroquine; amodiaquine; pyrimethamine; proguanil; chlorproguanil-dapsone; sulfonamides; sulfadoxine; sulfamethoxypyridazine; mefloquine; atovaquone; primaquine; halofantrine; doxycycline; clindamycin; artemisinin; artemisinin derivatives; artemether; dihydroartemisinin; arteether; and artesunate.

BRIEF DESCRIPTION OF THE DRAWINGS

FIG. 11C shows a photograph of the architecture illustrated in FIG. 11B.

FIG. 11D shows the results of external reinforcement on the mechanical strength of drug arms.

FIG. 13 shows the results of tensile tests on co-extruded arms.

DETAILED DESCRIPTION OF THE INVENTION

Definitions

Figure 1A:
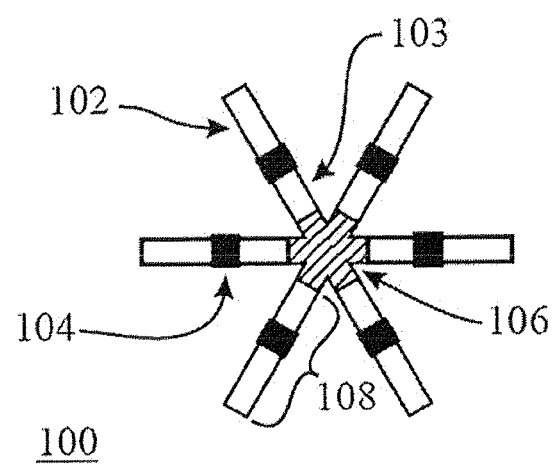
FIG. 1A shows a stellate design of a gastric residence system in its uncompacted state.

A "carrier polymer" is a polymer suitable for blending with an agent, such as a drug, for use in the invention.

An "agent" is any substance intended for therapeutic, diagnostic, or nutritional use in a patient, individual, or subject. Agents include, but are not limited to, drugs, nutrients, vitamins, and minerals.

A "dispersant" is defined as a substance which aids in the minimization of particle size of agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of an agent that is not the agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" (also referred to as a "tensile polymer") is a polymer that is capable of being deformed by an applied force from its original shape for a period of time, and which then substantially returns to its original shape once the applied force is removed.

A "coupling polymer" is a polymer suitable for coupling any other polymers together, such as coupling a first carrier polymer-agent component to a second carrier polymer-agent component. Coupling polymers typically form the linker regions between other components.

A "time-dependent polymer" or "time-dependent coupling polymer" is a polymer that degrades in a time-dependent manner when a gastric residence system is deployed in the stomach. A time-dependent polymer is typically not affected by the normal pH variations in the stomach.

"Substantially constant plasma level" refers to a plasma level that remains within plus-or-minus 25% of the average plasma level measured over the period that the gastric residence system is resident in the stomach.

A "hydrophilic therapeutic agent," "hydrophilic agent," or "hydrophilic drug" is an agent which readily dissolves in water. A hydrophilic agent is defined as an agent which has a solubility in water of 1 mg/ml or greater. Alternatively, a hydrophilic agent can be defined as an agent which has a log $P_{oct}$ (log partition coefficient $P_{oct}$, where $P_{oct}$=(concentration in 1-octanol)/(concentration in $H_2O$)) in a 1-octanol/water system of less than 0.5. The pH at which solubility or log $P_{oct}$ is measured is 1.6, approximating the gastric environment.

A "hydrophobic therapeutic agent," "hydrophobic agent," or "hydrophobic drug" is an agent which does not readily dissolve in water. A hydrophobic agent is defined as an agent which has a solubility in water of less than 1 mg/ml. Alternatively, a hydrophobic agent can be defined as an agent which has a log $P_{oct}$ (log partition coefficient) in a 1-octanol/water system of greater than 1. Alternatively, a hydrophobic therapeutic agent can be defined as an agent which has a higher solubility in ethanol than in water. Alternatively, a hydrophobic therapeutic agent can be defined as an agent which has a higher solubility in 40% ethanol/60% simulated gastric fluid than in 100% simulated gastric fluid.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

A "patient," "individual," or "subject" refers to a mammal, preferably a human or a domestic animal such as a dog or cat. In a preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods of the invention can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of a therapeutic agent is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present invention.

In addition to the embodiments and methods disclosed here, additional embodiments of gastric residence systems, and methods of making and using such systems, are disclosed in International Patent Application Nos. WO 2015/191920, WO 2015/191925, WO 2017/070612, and PCT/US2016/065453, which are incorporated by reference herein in their entirety.

Overall System Configuration

The current invention provides, inter alia, components of gastric residence systems which are designed to provide specific mechanical properties and customized drug release rates while resident in the stomach. The components described herein are suitable for use in a variety of gastric residence systems, including, but not limited to, stellate-shaped gastric residence systems and ring-shaped gastric residence systems.

Figure 1B:
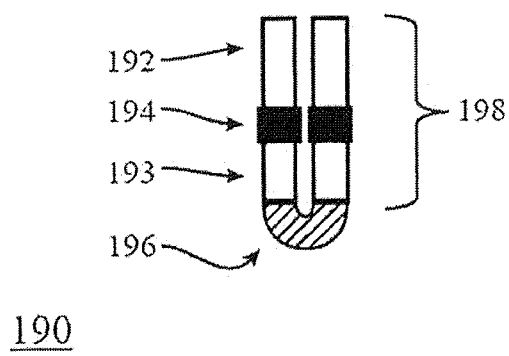
FIG. 1B shows a stellate design of a gastric residence system in a compacted or folded state.

The "stellate" configuration of a gastric residence system is also known as a "star" (or "asterisk") configuration. An example of a stellate system 100 is shown schematically in FIG. 1A. Multiple elongate members, or "arms" (only one such arm, 108, is labeled for clarity), are affixed to disk-shaped central elastomer 106. The elongate members or arms depicted in FIG. 1A are comprised of segments 102 and 103, joined by a coupling polymer or linker region 104 (again, the components are only labeled in one arm for clarity) which serves as a linker region. This configuration permits the system to be folded or compacted at the central elastomer. FIG. 1B shows a folded configuration 190 of the gastric residence system of FIG. 1A (for clarity, only two arms are illustrated in FIG. 1B). Segments 192 and 193, linker region 194, elastomer 196, and arm 198 of FIG. 1B correspond to segments 102 and 103, linker region 104, elastomer 106, and arm 108 of FIG. 1A, respectively. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

In some embodiments, the stellate system may have an elongate member or arm composed of only one segment, which is attached to the central elastomer by a linker region. This corresponds to FIG. 1A with the segments 103 omitted.

Figure 1C:
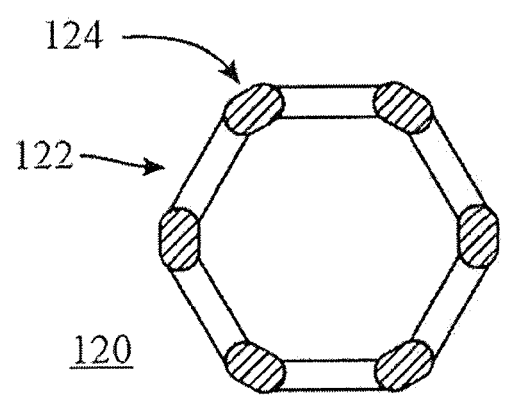
FIG. 1C shows a ring design of a gastric residence system in an uncompacted state.

FIG. 1C shows another possible overall configuration 120 for a gastric residence system, which is a ring configuration. Segments 122 are joined by coupling polymer or linker region 124 (only one segment and one coupling linkage are labeled for clarity). The coupling polymer/linker region in this design must also function as an elastomer, to enable the ring to be twisted into a compacted state for placement in a container, such as a capsule.

In one embodiment of the stellate configuration, the segments 102 and 103 comprise a carrier polymer blended with an agent or drug. In one embodiment of the ring configuration, the segments 122 comprise a carrier polymer blended with an agent or drug.

The coupling polymers of the gastric residence system, which serve as linker regions, are designed to break down gradually in a controlled manner during the residence period of the system in the stomach. If the gastric residence system passes prematurely into the small intestine in an intact form, the system is designed to break down much more rapidly to avoid intestinal obstruction. This is readily accomplished by using enteric polymers as coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient. In the system shown in FIG. 1A, at least the coupling polymer used for the couplings 104 are made from such enteric polymers.

In additional embodiments, a time-dependent coupling polymer or linker can be used. Such a time-dependent coupling polymer or linker degrades in a predictable, time-dependent manner. In some embodiments, the degradation of the time-dependent coupling polymer or linker may not be affected by the varying pH of the gastrointestinal system.

Figure 2A:
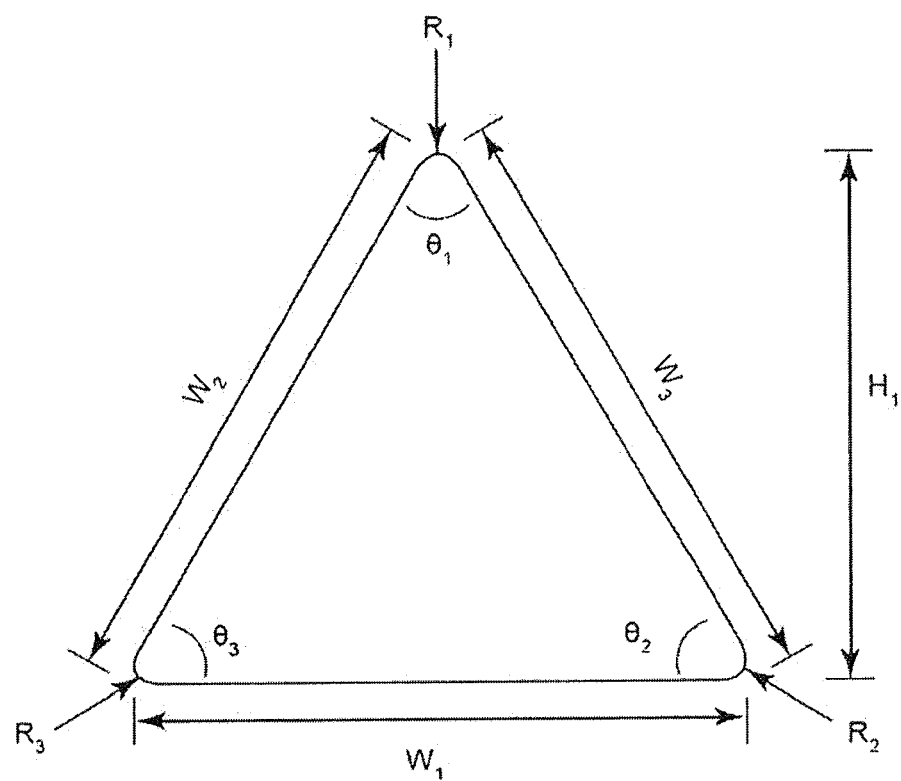
FIG. 2A shows dimensions of a triangular cross-section of an arm or arm segment in the shape of a triangular prism.
Figure 2B:
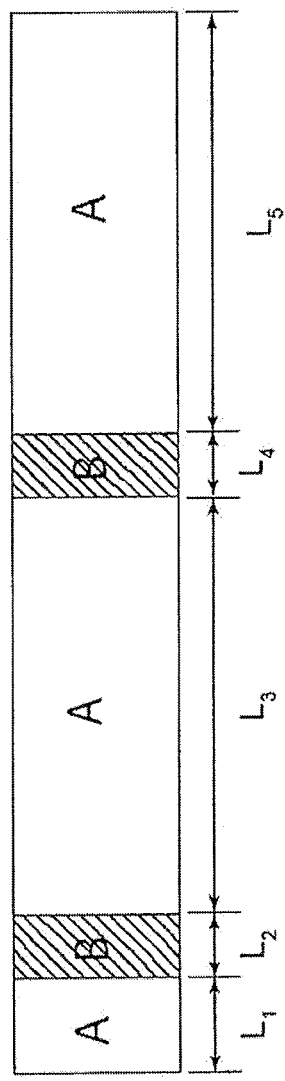
FIG. 2B shows a configuration of an arm (elongate member) with carrier polymer-agent regions A and linker (coupling polymer) regions B.
Figure 2C:
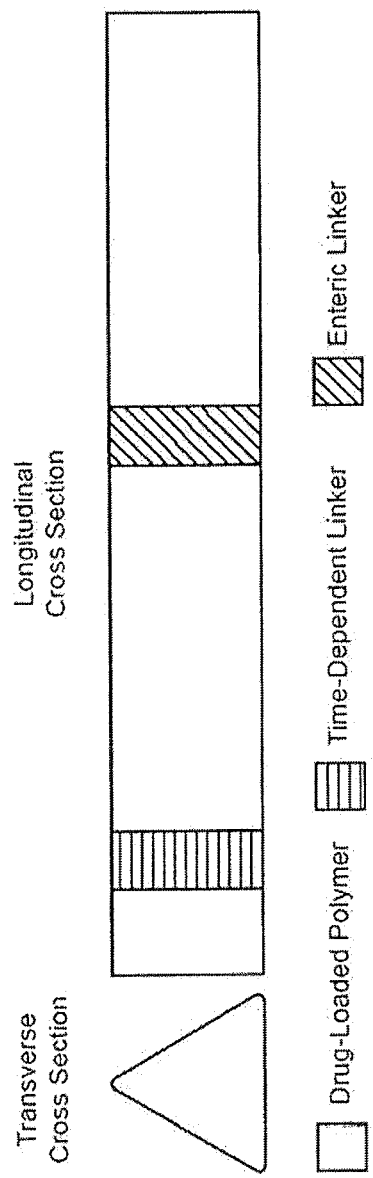
FIG. 2C shows a configuration of an arm (elongate member) having a triangular cross-section in the shape of a triangular prism (pictured at left). A longitudinal cross-section, along the axial length of the arm, is pictured at right. Carrier polymer-agent regions (i.e., drug-loaded polymer regions) are depicted as unmarked rectangles, a time-dependent linker region is depicted as a horizontally-striped rectangle, and an enteric linker region is depicted as a cross-hatched rectangle.
Figure 2D:
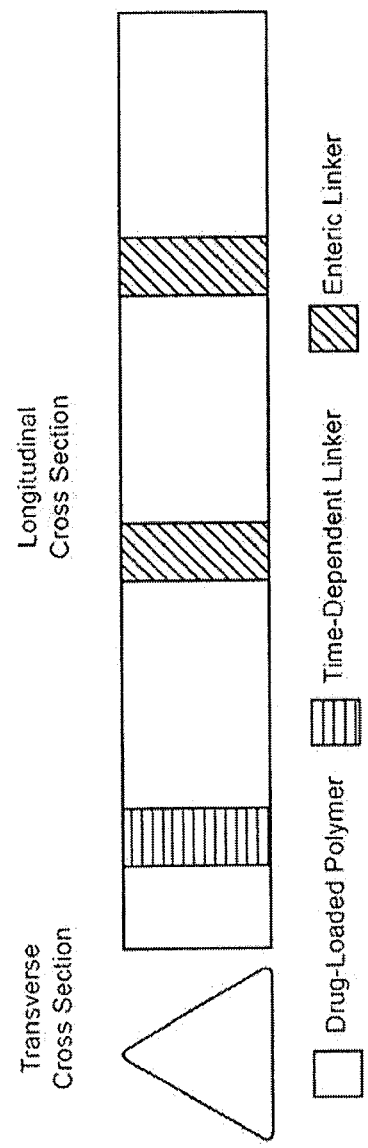
FIG. 2D shows another configuration of an arm (elongate member) having a triangular cross-section in the shape of a triangular prism (pictured at left). A longitudinal cross-section, along the axial length of the arm, is pictured at right. Carrier polymer-agent regions (i.e., drug-loaded polymer regions) are depicted as unmarked rectangles, a time-dependent linker region is depicted as a horizontally striped rectangle, and two separate enteric linker regions are depicted as cross-hatched rectangles
Figure 2E:
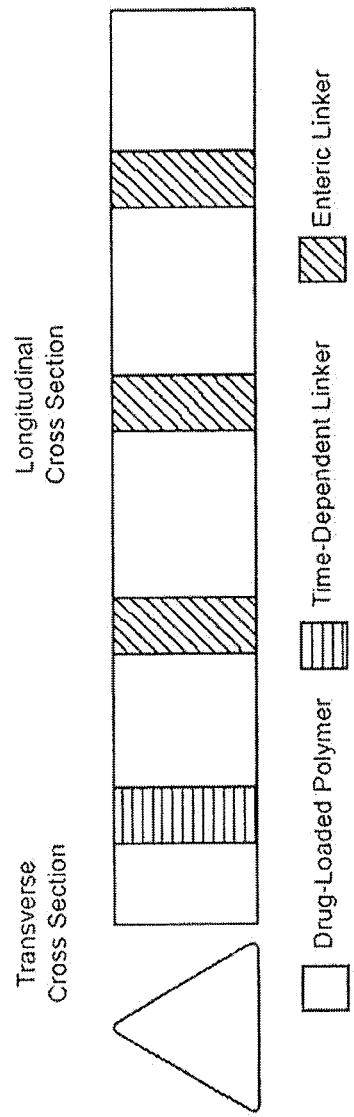
FIG. 2E shows another configuration of an arm (elongate member) having a triangular cross-section in the shape of a triangular prism (pictured at left). A longitudinal cross-section, along the axial length of the arm, is pictured at right. Carrier polymer-agent regions (i.e., drug-loaded polymer regions) are depicted as unmarked rectangles, a time-dependent linker region is depicted as a horizontally-striped rectangle, and three separate enteric linker regions are depicted as cross-hatched rectangles.

In additional embodiments, different types of linkers can be used in the gastric residence systems. That is, both enteric linkers (or enteric coupling polymers) and time-dependent linkers (or time-dependent coupling polymers) can be used. In some embodiments, a single elongate member (arm) of a stellate system can use both an enteric linker at some linker regions between segments, and a time-dependent linker at other linker regions between segments. An example of such an elongate member is shown in FIG. 2C, where a time-dependent linker region is used between a first segment and a second segment, and an enteric linker is used between a second segment and a third segment. Another example of such an elongate member is shown in FIG. 2D, where a time-dependent linker region is used between a first segment and a second segment, an enteric linker is used between a second segment and a third segment, and another enteric linker is used between a third segment and a fourth segment. Yet another example of such an elongate member is shown in FIG. 2E, where a time-dependent linker region is used between a first segment and a second segment, an enteric linker is used between a second segment and a third segment, another enteric linker is used between a third segment and a fourth segment, and another enteric linker is used between a fourth segment and a fifth segment. In some embodiments, a single elongate member (arm) of a stellate system can use both one or more enteric linkers and one or more time-dependent linkers at the same junction between segments; that is, two segments are linked by two or more linker regions, where at least one linker region is an enteric coupling polymer or linker and at least one linker region is a time-dependent coupling polymer or linker. In some embodiments, a single elongate member (arm) of a stellate system can use only one type of linker—that is, only enteric linkers or only time-dependent linkers—at different linking regions between segments, but the stellate system can at least one arm with only enteric linkers and at least one arm with only time-dependent linkers.

Use of multiple linker regions permits the gastric residence system to break into relatively small pieces after the desired residence time, for easier passage through the gastrointestinal tract. The methods of manufacture described herein, including co-extrusion and three-dimensional printing, provide a relatively straightforward way of adding additional linker regions without complicating the manufacture of the gastric residence systems. Earlier methods, in contrast, required production of each carrier polymer-agent segment and each linker region separately, followed by end-to-end assembly of the regions; in such methods, adding each additional linker region requires two additional steps to attach the linker region to the ends of the segments joined together by the linker region.

Linker regions are typically about 100 microns to about 2 millimeters in width, such as about 200 um to about 2000 um, about 300 um to about 2000 um, about 400 um to about 2000 um, about 500 um to about 2000 um, about 600 um to about 2000 um, about 700 um to about 2000 um, about 800 um to about 2000 um, about 900 um to about 2000 um, about 1000 um to about 2000 um, about 1100 um to about 2000 um, about 1200 um to about 2000 um, about 1300 um to about 2000 um, about 1400 um to about 2000 um, about 1500 um to about 2000 um, about 1600 um to about 2000 um, about 1700 um to about 2000 um, about 1800 um to about 2000 um, about 1900 um to about 2000 um, about 200 um to about 1000 um, about 300 um to about 1000 um, about 400 um to about 1000 um, about 500 um to about 1000 um, about 600 um to about 1000 um, about 700 um to about 1000 um, about 800 um to about 1000 um, or about 900 um to about 1000 um; or about 100 um to about 900 um about 100 um to about 800 um, about 100 um to about 700 um, about 100 um to about 600 um, about 100 um to about 500 um, about 100 um to about 400 um, about 100 um to about 300 um, or about 100 um to about 200 um. Linker regions can be about 100 um, about 200 um, about 300 um, about 400 um, about 500 um, about 600 um, about 700 um, about 800 um, about 900 um, about 1000 um in width, about 1100 um in width, about 1200 um in width, about 1300 um in width, about 1400 um in width, about 1500 um in width, about 1600 um in width, about 1700 um in width, about 1800 um in width, about 1900 um in width, or about 2000 um in width, where each value can be plus or minus 50 um (±50 um).

The central elastomeric polymer of a stellate system, such as polymer 106 of FIG. 1A, is typically not an enteric polymer; however, the central elastomeric polymer can also be made from such an enteric polymer where desirable and practical. In a ring system, such as that shown in FIG. 1C, at least one, and preferably all, of the couplings 124 are made from such enteric polymers.

The central elastomer should have a specific durometer and compression set. The durometer is important because it determines the folding force of the dosage form and whether it will remain in the stomach; a preferred range is from about 60 to about 90 A. The compression set should be as low as possible to avoid having permanent deformation of the gastric residence system when stored in the capsule in its compacted configuration. A preferred range is about 10% to about 20% range. Materials that fit these requirements are the QP1 range of liquid silicone rubbers from Dow Corning. In one embodiment, the QP1-270 (70 A durometer) can be used.

System Arm and Segment Design
Segment Shape

Figure 10A:
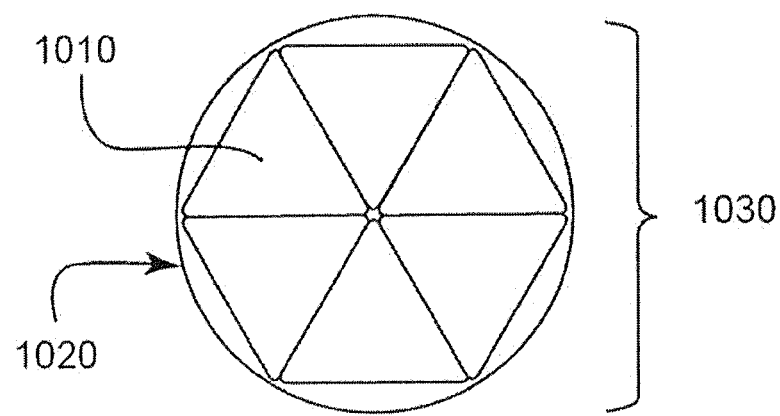
FIG. 10A shows the arrangement of elongate arms of an embodiment of a gastric residence system with six elongate arms, where the arm cross-section is triangular.

The elongate members, or arms, used in a stellate gastric delivery system can have a variety of shapes. The elongate members suitable for stellate configurations are typically also usable for ring configurations. In some embodiments, the segments forming the arms of the gastric residence system are cylindrical (that is, they have a circular cross-section). In some embodiments, the segments forming the arms of the gastric residence system are rectangular prisms (that is, they have a rectangular cross-section), such as square prisms (with a square cross-section). In some embodiments, the segments forming the arms of the gastric residence system are triangular prisms (that is, they have a triangular cross-section). FIG. 6A, FIG. 6B, FIG. 7A, FIG. 7B, FIG. 8A, FIG. 8B, FIG. 9A, FIG. 9B, and FIG. 9C show examples of segments that are triangular prisms. Differently shaped arms can be combined in the same gastric residence system where desirable and practical. Differently shaped segments can be combined in the same arm of a gastric residence system where desirable and practical. In one embodiment, all of the arms and all of the arm segments in a single gastric residence system have the same shape (e.g., all are cylindrical; all are triangular prisms; all are rectangular prisms). A triangular cross-section is shown at left in FIG. 10A. The arrangement of triangular cross-sections of the elongate members of a gastric residence system 1030 having six elongate members is shown at right in FIG. 10A; only one elongate member is labeled (1010). The gastric residence system is enclosed in container or capsule 1020. The vertices of the hexagon thus formed will exert stress on the retaining capsule when the system is in its compacted form.

Arms which have cross-sections in the shape of a polygon (such as arms with a triangular cross-section, rectangular cross-section, or square cross-section), or which have a sharp edge (such as arms with a pie-shaped cross-section) can have rounded corners and edges, for enhanced safety in vivo. That is, instead of having a sharp transition between intersecting edges or planes, an arc is used to transition from one edge or plane to another edge or plane. Thus, "triangular cross-section" includes cross-sections with an approximately triangular shape, such as a triangle with rounded corners. An arm with a triangular cross-section includes an arm where the edges are rounded, and the corners at the end of the arm are rounded. An example of an arm cross-section with rounded corners is shown in FIG. 2A; the rounded corners are labeled by the arrows labeled $R_1$, $R_2$, and $R_3$. Rounded corners and edges are also referred to as fillet corners, filleted corners, fillet edges, or filleted edges. An arm with a rectangular cross-section includes an arm where the edges are rounded, and the corners at the end of the arm are rounded; the shape of a rectangle with rounded corners is sometimes referred to as a rectellipse. An arm with a square cross-section includes an arm where the edges are rounded, and the corners at the end of the arm are rounded; the shape of a square with rounded corners is sometimes referred to as a squircle. Thus, in a preferred embodiment of any of the systems described herein, all sharp edges or corners of an arm, arm segment, or elongate member are rounded or filleted.

Figure 10B:
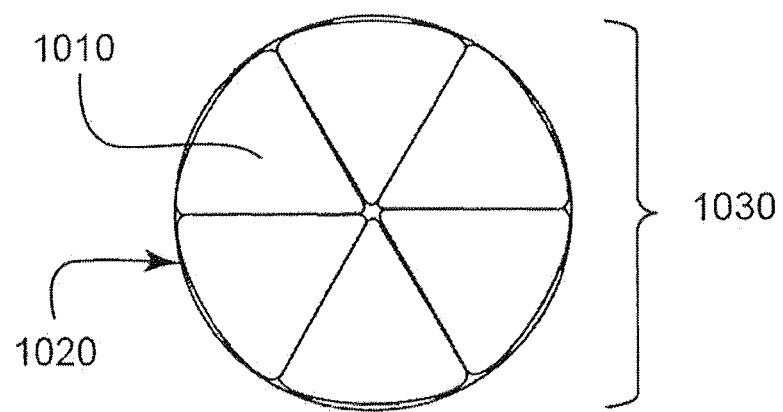
FIG. 10B shows the arrangement of elongate arms of an embodiment of a gastric residence system with six elongate arms, where the arm cross-section is wedge-shaped.

In a preferred embodiment, the cross-section of the elongate members, or arms, used in a stellate gastric delivery system is that of a circular section, where the circular section is formed by two radii of the cylinder lying in the same plane and the arc that the radii intersect. The angle between the two radii (the central angle of the arc) is preferably about 360 degrees divided by 4, 6, or 8, but can be about 360 degrees divided by any integer between 2 and 12 inclusive. That is, a cross-section described as a circular section resembles a slice of pie, such as the cross-section depicted at the left of FIG. 10B, and can be referred to as pie-shaped. Such a cross-section for the elongate member in a stellate system permits the gastric residence system to have an approximately cylindrical shape when compacted, as depicted at the right of FIG. 10B for a gastric residence system 1030 having six elongate members with wedge-shaped cross-sections (one elongate member, 1010, is labeled). The arrangement in FIG. 10B alleviates the stress on the containing capsule 1020 when the system is in its compacted form, as compared to the arrangement in FIG. 10A, and also permits more mass to be used in the elongate members, as less space in the capsule is wasted. Elongate members with such a cross-section can be produced via extrusion through a die having such a cross-section. For co-extrusion of multiple regions in a bulk configuration, such as an extruded slab or ribbon, compression molding or thermoforming can be used to form elongate members with such a cross-section from portions of the extruded bulk configuration.

Figure 10C:
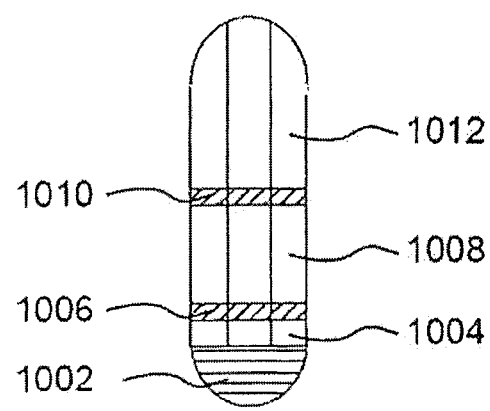
FIG. 10C shows a gastric residence system in a compacted state, having elongate arms with rounded tips.

In another preferred embodiment, the tips of the ends of the elongate members are curved, as shown in FIG. 10C, instead of having planar surfaces at the tips. Such a configuration allows the system to fit more snugly into a capsule, which aids in manufacturing and storage, and also uses all of the space within the capsule efficiently, to allow for additional carrier polymer-agent composition at the tips of the elongate members. FIG. 10C shows elastomer 1002, first segment 1004, first linker region 1006, second (or middle) segment 1008, second linker region 1010, and third (or final) segment 1012. The ends or tips of final segment 1012 are curved in the manner described to fit snugly into a capsule.

Segment Composition: Alternating Carrier Polymer-Agent Regions and Linker Regions FIG. 2A shows a cross-section of one embodiment of an arm, which is in the shape of a solid triangular prism. The triangular cross-section is characterized by sides of width $W_1$, $W_2$, and $W_3$, corresponding angles $\theta_1$, $\theta_2$, and $\theta_3$ opposite the side with the corresponding number, and fillet radii of $R_1$, $R_2$ and $R_3$. The arm has height $H_1$. FIG. 2B shows a side view of this embodiment of an arm. The regions labeled A are comprised of carrier polymer-agent, while the regions labeled B are comprised of linker material. The length of each region is independent of the length of each other region, as indicated by the labels $L_1$, $L_2$, $L_3$, $L_4$, and $L_5$; the overall length of the arm is $(L_1+L_2+L_3+L_4+L_5)$.

This arm embodiment can be produced by extruding material axially from the extruder device; that is, looking at the end of the extruder device from which the extruded arm material is emerging, one would see the cross-section of FIG. 2A. The extrusion would require extrusion of regions of carrier polymer-agent (A regions) of the appropriate lengths (e.g., length $L_1$, $L_3$, and $L_5$), followed by extrusion of regions of linker (B regions) of the appropriate lengths (e.g., length $L_2$, $L_4$). The final arm embodiment can be assembled by adhering or coupling the segments in the order $L_1$, $L_2$, $L_3$, $L_4$, $L_5$.

Alternatively, the arm embodiment of FIG. 2A and FIG. 2B can be produced by extruding material from the extruder device in a direction perpendicular to the longitudinal dimension (longest dimension) of the arm or elongate member. That is, looking at the face of the extruder device from which the extruded arm material is emerging, one would see the cross-section of FIG. 2B. The material would be extruded as a rectangular block or rectangular parallelepiped—that is, a slab—having dimensions of $H_1$, $(L_1+L_2+L_3+L_4+L_5)$, and a third dimension of unspecified length; extrusion of the block is in the direction of this third dimension, and thus the third dimension can be as long as desired, provided that sufficient raw materials are fed into the extrusion device to produce the desired dimension. The rectangular block or slab can then be cut at an oblique angle to produce a solid triangular prism. (That is, the rectangular block is cut at an angle which is oblique to the plane formed by the $(L_1+L_2+L_3+L_4+L_5)$ side and the third dimension along which the block is extruded.) If a solid rectangular prism shape for the arms is desired (not shown), the rectangular block can be cut at a 90° angle instead of an oblique angle. If a pie-shaped cross-section is desired, the material can be cut at an oblique angle, followed by a second cut on the piece to form the curved arc. Alternatively, if a pie-shaped cross-section is desired, the material can be cut into a triangular prism, rectangular prism, or other shape of appropriate size, and then compression molded, or stamped, into the desired shape. This co-extrusion method is described further below with reference to Example 2, FIG. 12A, FIG. 12B, FIG. 12C, FIG. 12D, and FIG. 13.

Segment Composition: "Islands-in-the-Sea" Linker Regions

Figure 3A:
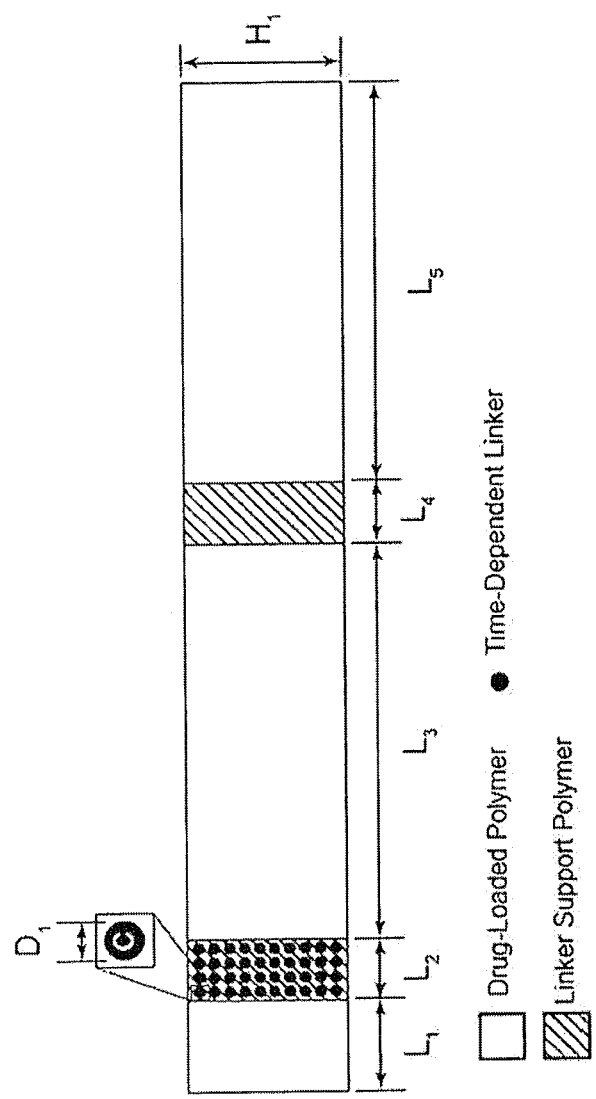
FIG. 3A shows a configuration of an elongate member with an "islands-in-the-sea" arrangement of material in the linker region.
Figure 3B:
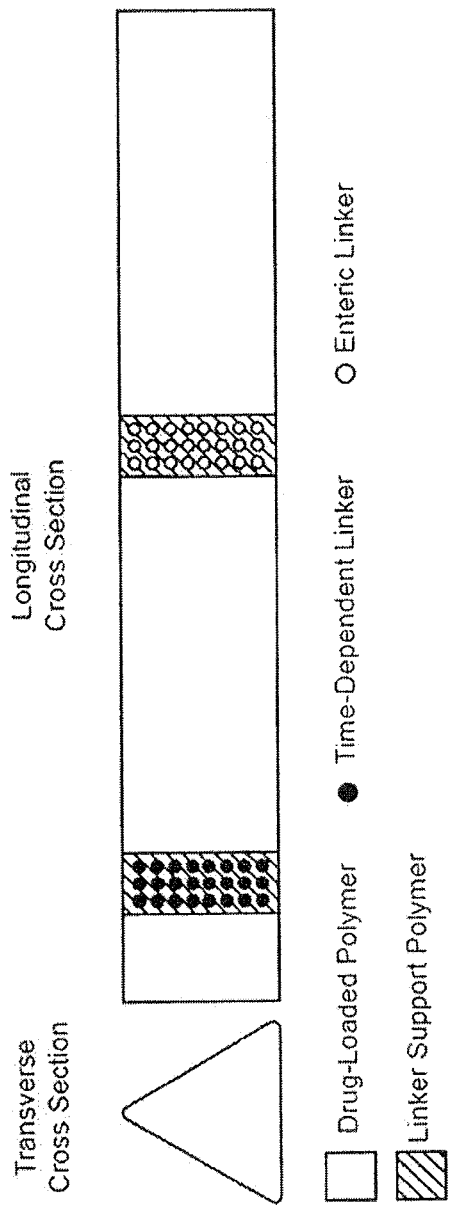
FIG. 3B shows a configuration of an elongate member with an "islands-in-the-sea" arrangement of material in the linker region.
Figure 3C:
FIG. 3C shows an expanded view of the "islands-in-the-sea" arrangement of material in the linker region of FIG. 3A.
Figure 3C:

Some arm embodiments can be prepared as carrier polymer-agent segments linked by "islands-in-the-sea" linker regions. FIG. 3A, FIG. 3B, and FIG. 3C show examples of such linker regions. In FIG. 3A, segments 304 and 308 are connected by an "islands-in-the-sea" linker region 306, while segments 302 and 304 are connected by another "islands-in-the-sea" linker region (appearing above the line segment $L_2$, but not otherwise labeled). In the islands-in-the-sea configuration for the linker region, a first linker material comprises the "sea," indicated by 324 in FIG. 3C. Numerous portions of a second linker material comprise "islands" (one such island 322 is labeled in FIG. 3C), which are placed in the "sea" of the first linker material. The linker region generally conforms to the overall configuration of the arm; that is, if the arm is in the shape of a triangular prism, the linker region will be in the shape of a triangular prism as well.

The second linker material, or linker island material, which forms the islands-in-the-sea of the first linker material, can be placed in the sea in a variety of configurations. In FIG. 3A and FIG. 3B, the islands are in the form of cylinders which penetrate the sea in a direction transverse to the overall longitudinal (axial) direction of the arm. The inset in FIG. 3A shows an island (labeled "C") with diameter $D_1$. The island regions can enter the linker region from one location on the surface of the linker region, and penetrate through the "linker sea" to emerge from another location on the surface of the linker region. This configuration can be manufactured by co-extrusion or by three-dimensional printing. The islands can enter the linker region from one location on the surface of the linker region, and terminate in an interior portion of the linker region; this configuration can be manufactured by three-dimensional printing.

Figure 3D:
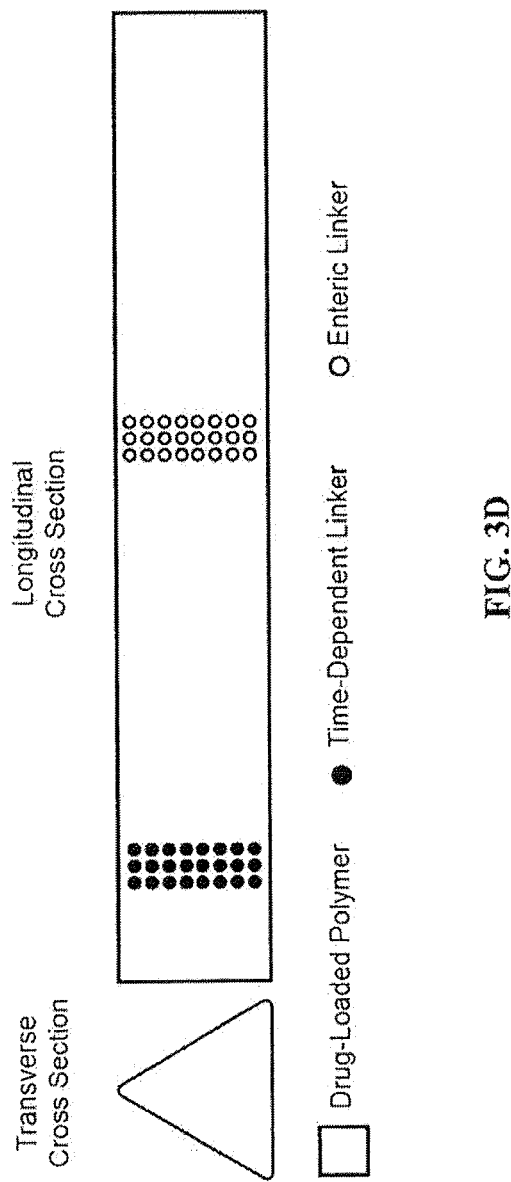
FIG. 3D shows a configuration of an elongate member with an "islands-in-the-sea" arrangement of material in the linker region, where the "sea" of the linker region comprises carrier polymer-agent blend.
Figure 3E:
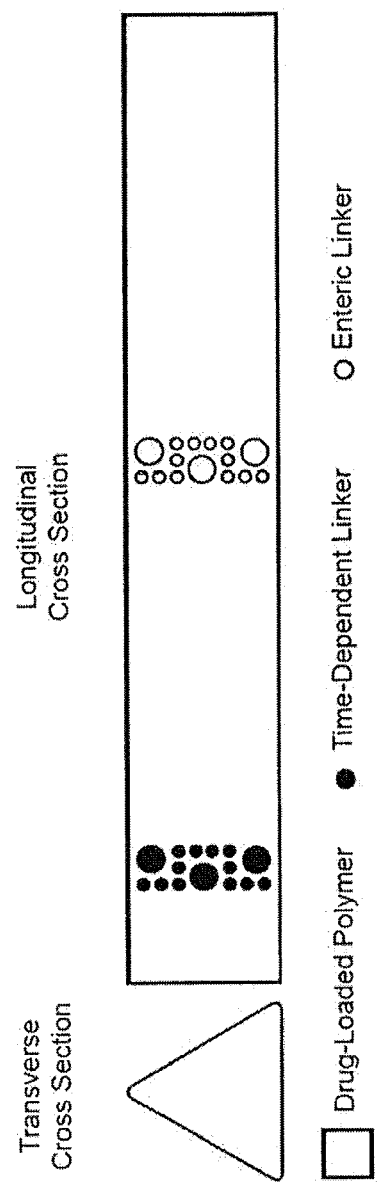
FIG. 3E shows a configuration of an elongate member with an "islands-in-the-sea" arrangement of material in the linker region, where the "sea" of the linker region comprises carrier polymer-agent blend, and where the "islands" have varying diameters.

The diameter of the "islands" can be uniform for all islands, or can vary between islands, such as the arrangement shown in FIG. 3E. The diameter of the islands in a linker region should not exceed the width of the linker region. In one embodiment, the islands independently have a diameter of about 1 um to about 100 um, such as about 1 um to about 90 um about 1 um to about 80 um, about 1 um to about 70 um, about 1 um to about 60 um, about 1 um to about 50 um, about 1 um to about 40 um, about 1 um to about 30 um, about 1 um to about 20 um, or about 1 um to about 10 um; or about 10 um to about 100 um about 20 um to about 100 um, about 30 um to about 100 um, about 40 um to about 100 um, about 50 um to about 100 um, about 60 um to about 100 um, about 70 um to about 100 um, about 80 um to about 100 um, or about 90 um to about 100 um. The islands can independently have diameters of about 10 um, about 20 um, about 30 um, about 40 um, about 50 um, about 60 um, about 70 um, about 80 um, about 90 um, or about 100 um, where each value can be plus or minus about 5 um (+5 um). The islands can independently have diameters of about 1 um, about 2 um, about 3 um, about 4 um, about 5 um, about 6 um, about 7 um, about 8 um, about 9 um, or about 10 um.

While the islands are depicted as circular in cross-section in the figures, they can be of any shape capable of fabrication by co-extrusion or by three-dimensional printing. For non-circular cross-sections, the size ranges for diameters given above are size ranges for the longest cross-sectional dimension of the non-circular region (e.g., the major axis when an island is elliptically shaped).

A variety of materials can be used for the first linker material (the "sea"). In one embodiment, the same carrier polymer-agent blend that forms the segments connected by the linker regions can also be used as the first linker material. Such an arrangement is shown in FIG. 3D. This embodiment has the advantage of simplifying co-extrusion manufacture, as only the islands need be added during co-extrusion of the segment. If this embodiment is manufactured using three-dimensional printing, using carrier polymer-agent blend material as the first linker material will minimize the number of different polymer inputs needed for the three-dimensional printer. This can also provide relatively strong linker regions during the residence period in the stomach.

In one embodiment, the carrier polymer, without the agent, can be used as the first linker material, which can help promote bonding between the carrier polymer-blend segments and the linker regions.

Polycaprolactone (PCL) is a preferred material for use as the "sea" material. In another embodiment, polydioxanone is used as the "sea" material. In additional embodiments, the "sea" material can comprise hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof.

In the event that use of the carrier polymer (with or without agent) results in a linker region that does not allow the system to break apart after the desired residence time, a separate polymer can be used as the first linker material. In one embodiment, enteric polymers can be used as the first linker material. In one embodiment, time-dependent polymers can be used as the first linker material. In one embodiment, low molecular weight polycaprolactone is used. In one embodiment, a weakening agent is mixed with carrier polymer to form the first linker material; for example, carnauba wax, paraffin wax, or RH40 can be mixed in with the carrier polymer (such as polycaprolactone) to produce a weaker polymer for use in the linker region.

A variety of materials are also available for use as the second linker material (the "islands"). In one embodiment, enteric polymers can be used as the second linker material. In one embodiment, time-dependent polymers can be used as the second linker material. "Island" material can comprise one or more of hydroxypropyl methylcellulose acetate succinate (HPMC-AS), hydroxypropyl methylcellulose phthalate, cellulose acetate phthalate, cellulose acetate succinate, methylcellulose phthalate, ethylhydroxycellulose phthalate, polyvinylacetate phthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylic acid-ethyl acrylate copolymer, methacrylate-methacrylic acid-octyl acrylate copolymer, shellac, poly (methyl vinyl ether/maleic acid) monoethyl ester, poly (methyl vinyl ether/maleic acid) n-butyl ester, and copolymers, mixtures, blends and combinations thereof.

For enteric or time-dependent polymers arranged as islands or channels in a sea of hydrophobic structural polymer, the time required for degradation or dissolution of the time dependent or enteric linker material depends on the rate of water penetration into the polymer matrix. Diffusion time of water into polymer islands can be approximated as $t$-$L^2/2D$, where L is the distance of water penetration and D is the diffusivity of water in the polymer. For a given geometry, diffusion time of water can be tuned by altering the diffusivity of the material. Diffusivity of polymers can be tuned by blending with fillers or other polymers. For example, water penetration to the center of the formulation via a polymethylmethacrylate capillary (a distance of L=1.5 mm and D~3.35e-8 $cm^2/s$ for water in PMMA) would require ~3.9 days. To achieve water penetration of 1.5 mm into the matrix over 8 days, the diffusivity of water in the polymer would be targeted at 1.6e-8 $cm^2/s$.

Segment Composition: Interlocking Connections ("Lock-and-Key" Junctions) Between Carrier Polymer-Agent and Linker Regions The linker regions used in the arms may be of uniform dimensions along its length, such as in the embodiment shown in regions B of the arm pictures in FIG. 2B. Alternatively, the linker region may be of variable dimensions along its length, as depicted in FIG. 4A, FIG. 4B, FIG. 4C, and FIG. 4D. The linker regions in FIG. 4A, FIG. 4B, FIG. 4C, and FIG. 4D have portions which extend from the main body of the linker region into the segments comprised of carrier polymer-agent material, in an interlocking, or "lock-and-key," configuration. In some embodiments, a portion of one or more segments comprised of carrier polymer-agent material extends from the main body of the carrier polymer-agent segment into the linker region, again in an interlocking or "lock-and-key" configuration. In some embodiments, a portion of one or more linker regions extends from the main body of the linker region into the carrier polymer-agent segment, and a portion of one or more segments comprised of carrier polymer-agent material extends from the main body of the carrier polymer-agent segment into the linker region.

The carrier polymer-agent material and the linker region form an interlocking connection, by fitting together projections in the linker region with recesses in the carrier polymer-agent material (such as shown in FIG. 4A, FIG. 4B, FIG. 4C, and FIG. 4D), or by fitting together projections in the carrier polymer-agent material with recesses in the linker region, or both by fitting together projections in the linker region with recesses in the carrier polymer-agent material and by fitting together projections in the carrier polymer-agent material with recesses in the linker region. These interlocking connections provide for enhanced bonding between the linker regions and the segments comprising carrier polymer-agent material.

Figure 4A:
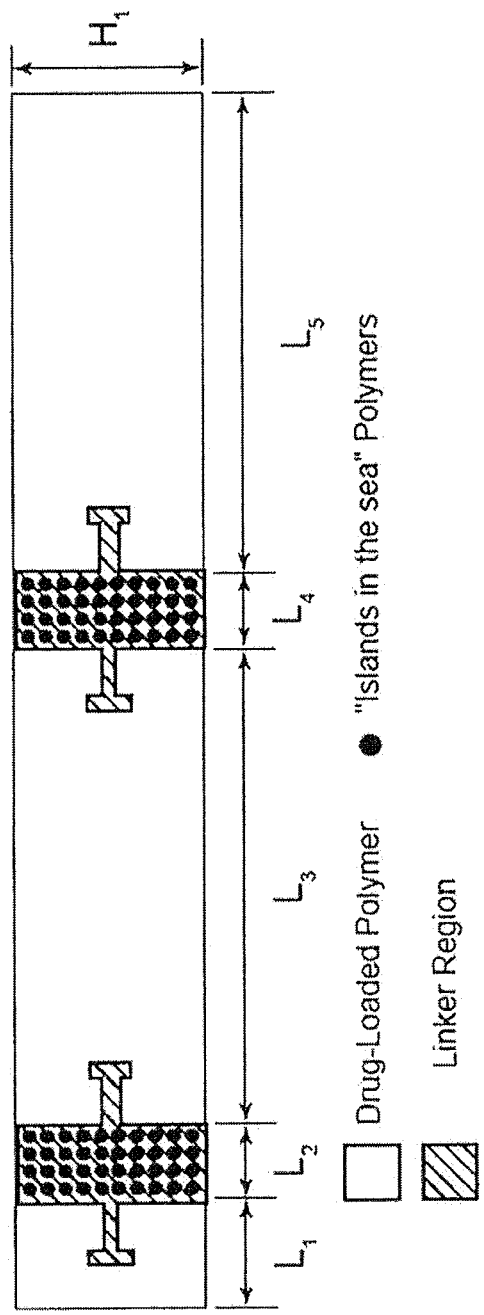
FIG. 4A shows a configuration of arm segments with an "islands-in-the-sea" arrangement of material in the linker region, and a "lock-and-key" design between the linker region and the carrier polymer-agent region.
Figure 4B:
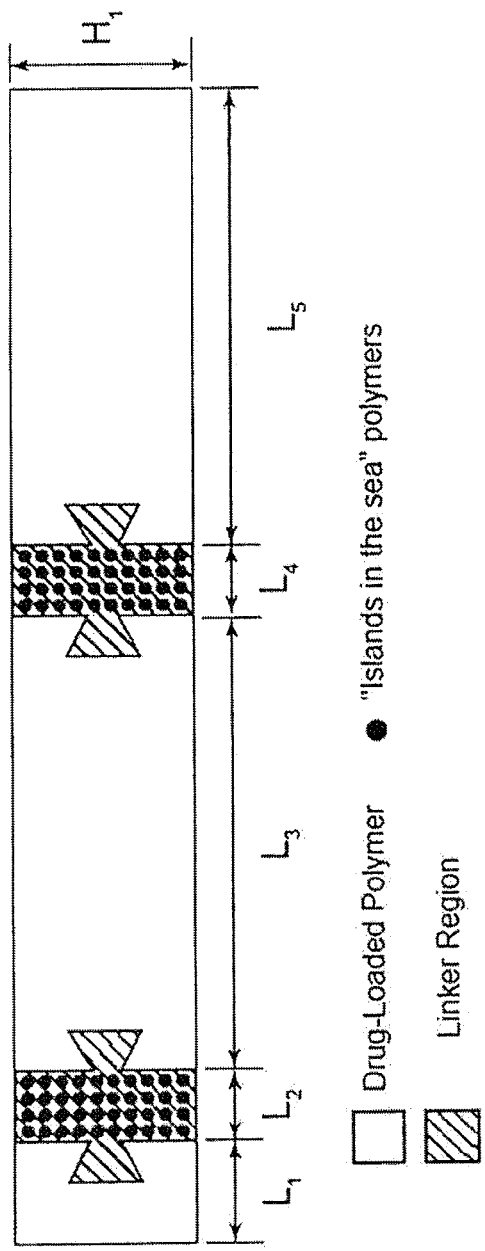
FIG. 4B shows another configuration of arm segments with an "islands-in-the-sea" arrangement of material in the linker region, and a "lock-and-key" design between the linker region and the carrier polymer-agent region.
Figure 4C:
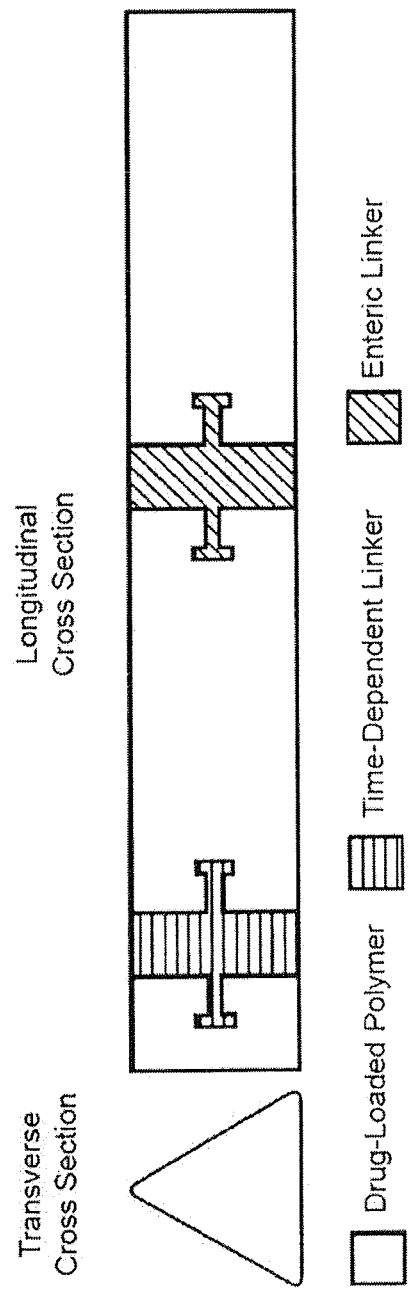
FIG. 4C shows another configuration of arm segments with "lock-and-key" designs between the linker regions and the carrier polymer-agent (drug-loaded polymer) regions. One of the lock-and-key linkers is a time-dependent linker, while the other lock-and-key linker is an enteric linker.
Figure 4D:
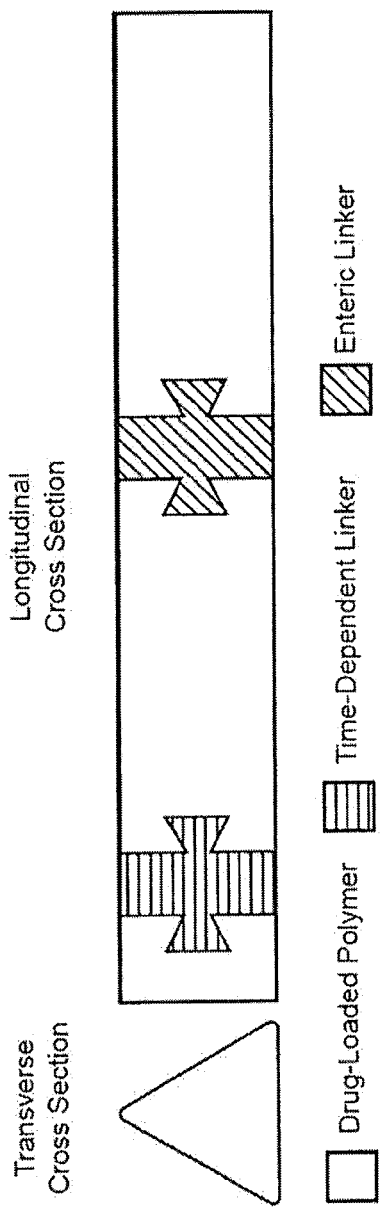
FIG. 4D shows another configuration of arm segments with "lock-and-key" designs between the linker regions and the carrier polymer-agent (drug-loaded polymer) regions. One of the lock-and-key linkers is a time-dependent linker, while the other lock-and-key linker is an enteric linker.

The linker regions in the interlocking connection configuration can additionally comprise islands-in-the-sea polymers, as in FIG. 4A or FIG. 4B. FIG. 4C and FIG. 4D show interlocking linkers without the islands-in-the-sea polymers. In FIG. 4C and FIG. 4D, one interlocking linker region is a time-dependent linker, while the other interlocking linker region is an enteric linker.

In one embodiment, the interlocking segments as described above are produced by three-dimensional printing. In one embodiment, the interlocking segments as described above are produced by co-extrusion.

Segment Composition: "Islands-in-the-Sea" Carrier Polymer-Agent Regions

Figure 5A:
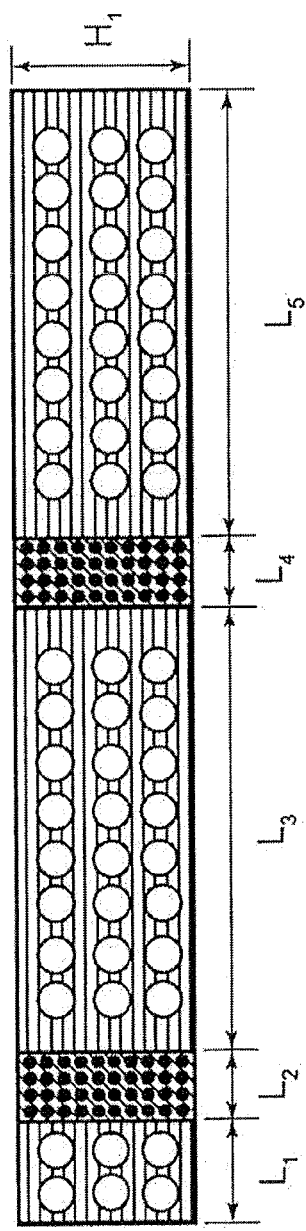
FIG. 5A shows a configuration of a segment with an "islands-in-the-sea" arrangement of material in the linker region, and an "islands-in-the-sea" arrangement of material in the carrier polymer-agent region.

Some arm embodiments can be prepared comprising carrier polymer-agent segments which are in an "islands-in-the-sea" configuration. In this embodiment, one or more segment island materials can be used to create the "islands-in-the-sea" configuration, where the carrier polymer-agent blend comprises the segment sea material. FIG. 5A shows such a configuration, where both the carrier polymer-agent segments and the linker regions have the islands-in-the-sea configuration. However, the islands-in-the-sea configuration can be used for the carrier polymer-agent segments without using a linker region also having the islands-in-the-sea configuration. That is, the islands-in-the-sea configuration can be used for the carrier polymer-agent segments, while using uniform linker regions, or linker regions having only a single linker material. This permits further modulation of the properties of the gastric residence system. For example, channels of relatively permeable materials can be used as the segment island material, allowing liquid, particularly water or gastric fluid, to contact a greater amount of surface area of the carrier polymer-agent segment sea material than only the external surface of the segment. Alternatively, an additional agent or agents can be used as the segment island material, for a combined administration. The segment island material with the additional agent or agents can be relatively quick-eluting or quick-dissolving, in the event that a bolus dosage of additional agent is desired upon entry of the gastric residence system into the stomach, or the agent or agents can elute slowly from the segment island material, for gradual co-delivery of the additional agent with the agent contained in the carrier polymer-agent blend in the segment sea material.

Figure 5B:
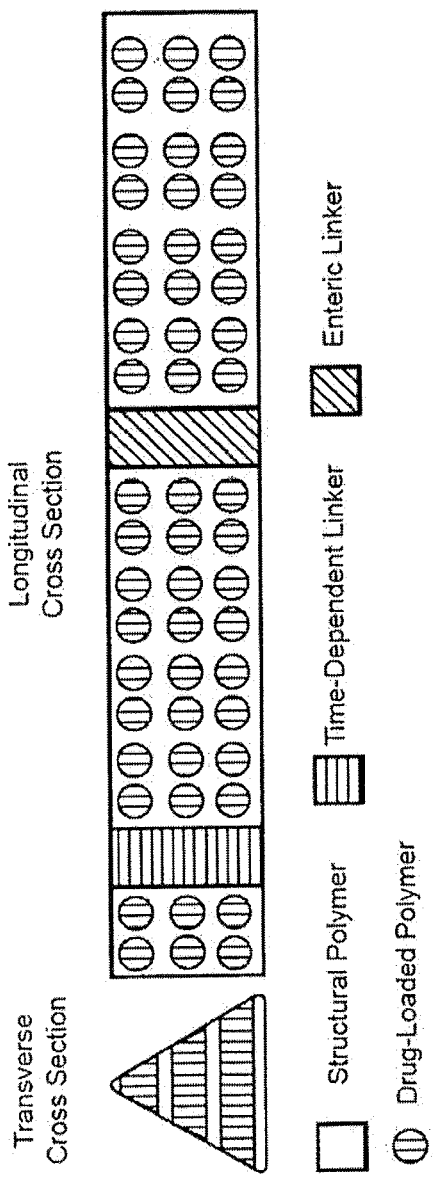
FIG. 5B shows a configuration of an elongate member with an "islands-in-the-sea" arrangement of "islands" of carrier polymer-agent material in a "sea" of structural polymer, joined together by a time-dependent linker and an enteric linker.

FIG. 5B shows another embodiment of an elongate member, with islands-in-the-sea configurations in the segments between linker regions. In this embodiment, carrier polymer-agent blends are used as islands in a sea of structural polymer, which significantly relaxes the requirements for mechanical integrity and stability of the carrier polymer-agent blend. Soft polymers and waxes can be used as carrier material, such as Kolliphor RH40, carnauba wax, P407. Degradable polymers, such as polyanhydrides, polyphosphazenes, and polycyanoacrylates can also be used as carrier polymers. The structural polymer used in this configuration should have high Young's modulus, tensile strength, and compression strength, and also needs to interface well with the carrier polymer-agent blend (that is, the structural polymer and carrier polymer should be chemical compatible and have similar melting temperatures). Examples of structural polymers which can be used in this configuration are poly lactic acid, polycarbonate, polyether ether ketone, polyethylene, and polypropylene.

Segment Composition: Multi-Lamellar Segments

Figure 6A:
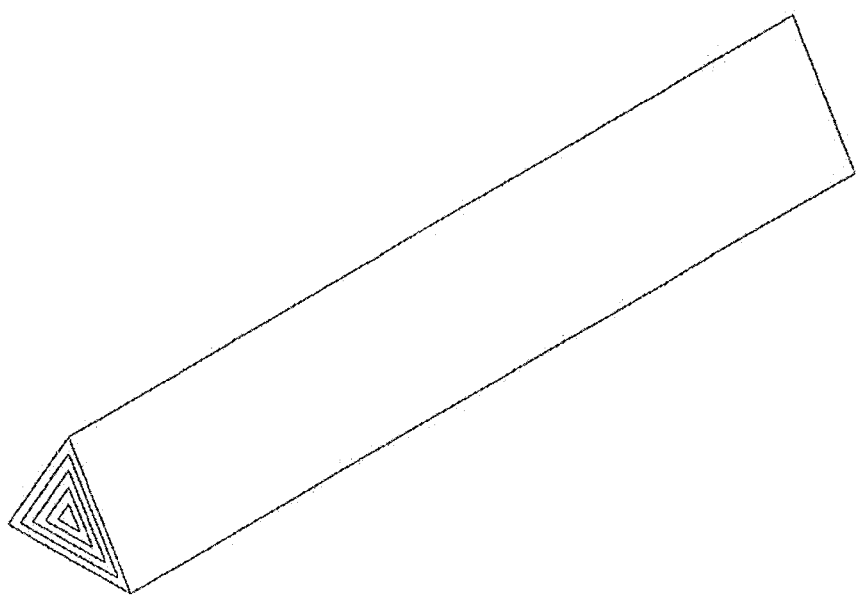
FIG. 6A shows a multi-lamellar embodiment of a segment of a branch for use in a gastric residence system.

In one embodiment, the gastric residence systems utilize multi-lamellar segments. An example of one implementation of a multi-lamellar segment is shown in FIG. 6A. The segment comprises two or more layers of carrier polymer-agent blend. This layering allows for different concentrations of agents or drugs. A concentration gradient of agent or drug can be generated across the layers to provide any desired release rate of agent or drug from the segment and/or from the overall system.

In one embodiment, a multi-lamellar segment comprises two or more layers comprising a carrier polymer-agent blend, where the concentration of agent or drug in each layer differs from the concentration of one or more adjacent layers of the segment. In one embodiment, a multi-lamellar segment comprises two or more layers comprising a carrier polymer-agent blend, where the concentration of agent or drug in each layer decreases with increasing diameter (or distance) from the center of the segment. In one embodiment, a multi-lamellar segment comprises two or more layers comprising a carrier polymer-agent blend, where the concentration of agent or drug in each layer increases with increasing diameter (or distance) from the center of the segment.

For example, a cylindrical segment of carrier polymer-agent blend is prepared which has three layers, where the first layer comprises a core cylinder 1 mm in diameter. The second layer, which is essentially a cylindrical tube with an annular cross-section, has an inner diameter of 1 mm and an outer diameter of 2 mm, and thus has a layer thickness of 1 mm. The third (outer) layer, which is also a cylindrical tube with an annular cross-section, has an inner diameter of 2 mm and an outer diameter of 3 mm, and also has a layer thickness of 1 mm. For a segment that is 10 mm in length, the total volume of the first (core) layer will be about 31.42 cubic millimeters, the volume of the second layer will be about 94.3 mm$^3$, and the volume of the second layer will be about 157 mm$^3$. The volumes of the second and third layers are obtained by calculating the volume of a cylinder having its outer diameter, and subtracting the volume of a cylinder having its inner diameter, e.g., for the third layer, $V=[\pi \times (3 \text{ mm})^2 \times 10 \text{ mm}] - [\pi \times (2 \text{ mm})^2 \times 10 \text{ mm}]$. Thus, the second layer has three times the volume of the first layer, and the third layer has five times the volume of the first layer. The concentration of agent or drug in the segment layers can be adjusted so that each layer contains roughly equal amounts of agent or drug. If the concentration in the third, most voluminous layer is C, then the concentration of agent or drug used in the second layer can be 1.67 times C, and the concentration of agent or drug used in the first layer can be 5 times C. The lamellar concentrations of agent or drug used can be adjusted to provide for any desired rate of elution of the agent or drug; in the previous example, it may be desired to use a concentration of 1 C in the third (outer) layer, 3 C in the second layer, and 15 C in the first layer, to provide for an increase in elution over time. Alternatively, elution of the agent or drug can be tapered down over time, for example by using a concentration of IC in the third layer, one-half C in the second layer, and one-quarter C in the first layer.

In further embodiments, more than one agent or drug can be used in the different carrier polymer-agent blend layers of a multi-lamellar segment. In one embodiment, a first agent or drug is present in at least one layer of the two or more layers in the segment, and a second agent or drug is also present in at least one layer of the two or more layers in the segment. In one embodiment, a first agent or drug is present in at least one layer of the two or more layers in the segment, and one or more additional agent or drugs (that is, a second agent or drug, a third agent or drug, etc.) are also present in at least one layer of the two or more layers. In one embodiment, only one agent is present in each layer (that is, each layer contains only one agent). In one embodiment, two or more agents are present in at least one layer (that is, one or more layers can contain two or more agents).

Figure 6B:
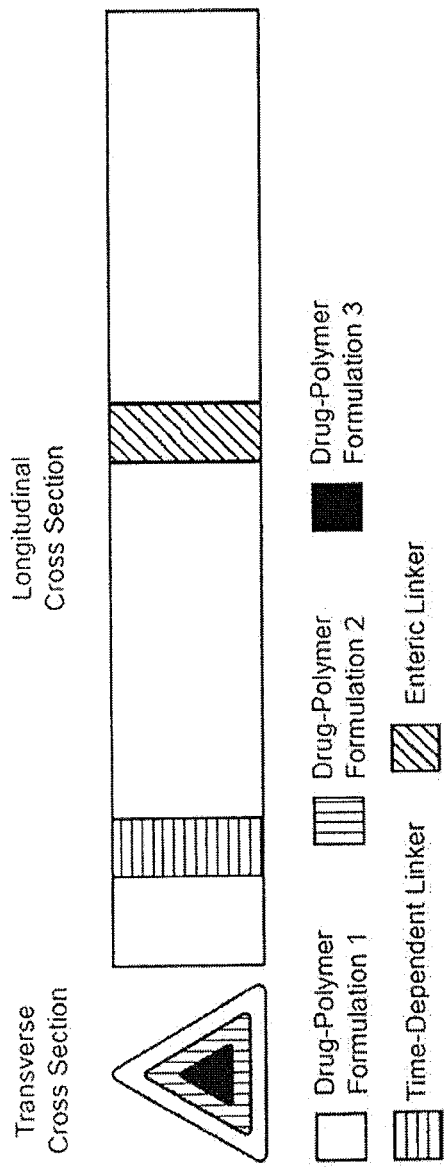
FIG. 6B shows a multi-lamellar embodiment of an elongate member with multi-lamellar carrier polymer-agent segments, joined by a time-dependent linker and an enteric linker.

FIG. 6B shows an embodiment of an elongate member having multiple carrier polymer-agent layers (labeled as drug-polymer formulations in the figure). To compensate for the reduction in mass transfer area as drug is released from the surface of the dosage form, formulations with different release rates can be layered, forming the lamellar structure depicted in FIG. 6B. Carrier polymer-agent (drug-polymer) Formulation 1 would be a relatively slowly releasing formulation, while formulation 4 would be a quickly-releasing formulation; the order of rate of release of the Formulations is Formulation 1<Formulation 2<Formulation 3<Formulation 4. Release rate from each layer and layer thicknesses can be tuned to achieve a linear overall release rate from the dosage form. Formulations 1-4 may vary in agent or drug concentration (for example, agent or drug load in Formulation 4>Formulation 3>Formulation 2>Formulation 1) or in excipient concentration.

Segment Composition: Internally Reinforced Segments

Figure 7A:
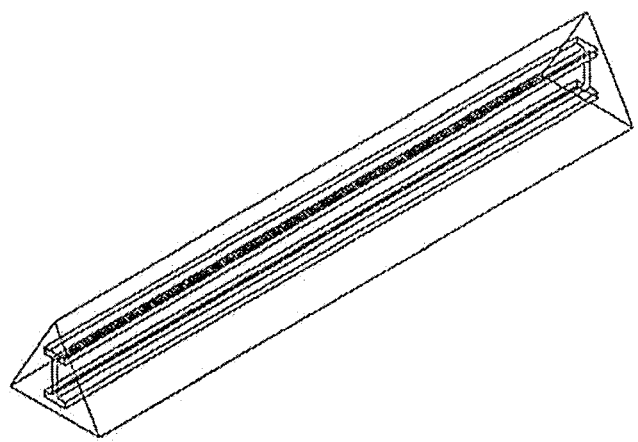
FIG. 7A shows an embodiment of a segment with an I-beam-type internal reinforcement.
Figure 7B:
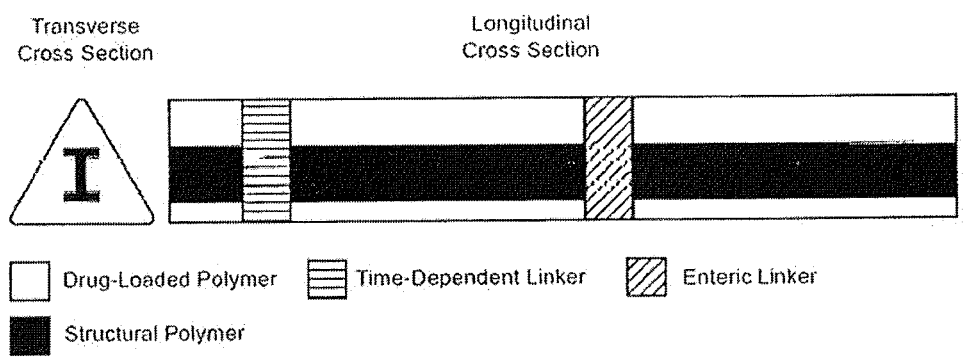
FIG. 7B shows an embodiment of an elongate member with an I-beam-type internal reinforcement.
Figure 8A:
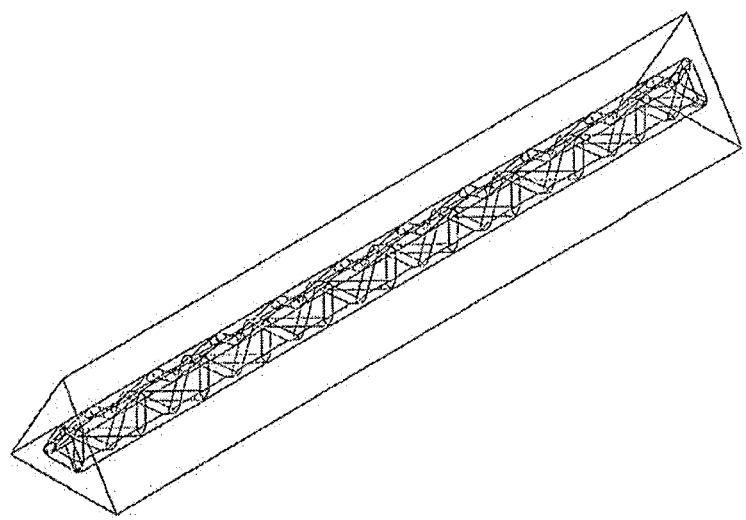
FIG. 8A shows an embodiment of a segment with a truss-type internal reinforcement.
Figure 8B:
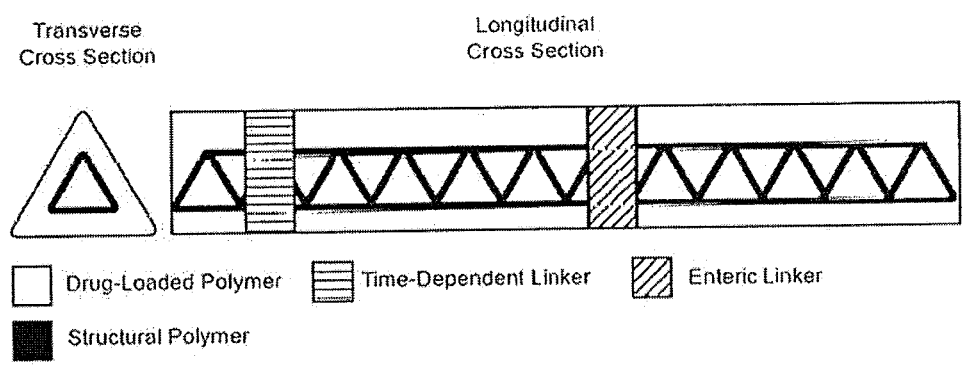
FIG. 8B shows an embodiment of an elongate member with a truss-type internal reinforcement.
Figure 9A:
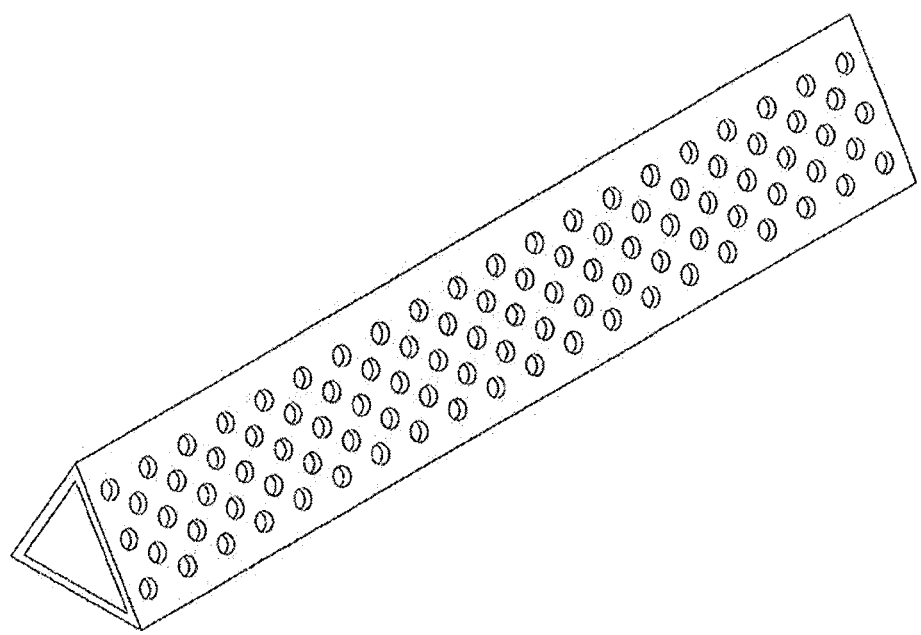
FIG. 9A shows an embodiment of a segment with a fenestrated (perforated) external support.
Figure 9B:
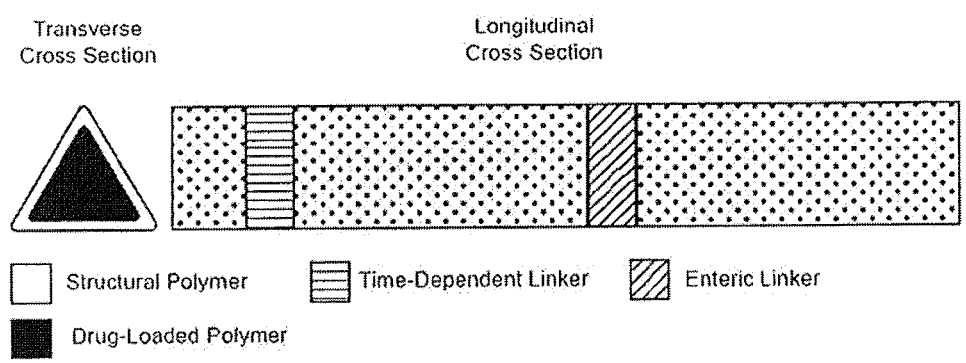
FIG. 9B shows an embodiment of an elongate member with a fenestrated (perforated) external support.
Figure 9C:
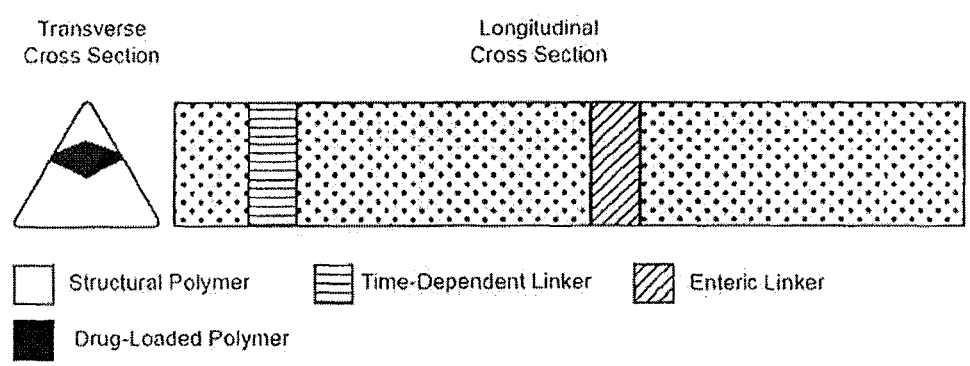
FIG. 9C shows an embodiment of an elongate member with a fenestrated (perforated) external support.

The strength of a segment can be improved by depositing reinforcing material into the internal portion of the segment, typically in the central region of the segment. The reinforcing material significantly relaxes the mechanical requirements of the carrier polymer-agent material, as it provides the principal mechanical support for the segment. The reinforcing material extends axially along the segment. A variety of shapes and configurations can be used for the reinforcing material. An I-beam design, such as that shown in FIG. 7A and FIG. 7B, provides excellent torsional and bending strength, and improves the interface between the carrier polymer-agent blend and reinforcing material. A truss configuration of the reinforcing material, such as that shown in FIG. 8A and FIG. 8B, minimizes the amount of reinforcing material needed, while still providing excellent strength. The reinforcing material can have an I-beam configuration. The reinforcing material can have an H-beam configuration (where an H-beam is similar to an I-beam, but with wider flanges). The reinforcing can have a truss configuration. The reinforcing material can have a cylindrical configuration. The reinforcing material can have a triangular prism configuration (that is, the configuration of a rod with a triangular cross-section). The reinforcing material can have a "pie-shaped" configuration (that is, the configuration of a rod with a "pie-shaped" cross-section, where the "pie shape" is represented by a triangle where one side of the triangle has been replaced with an arc of a circle; the cross-sections of the arms shown in FIG. 10B are examples of pie-shaped cross-section). The reinforcing material can have a rectangular prism configuration or a square prism configuration (that is, the configuration of a rod with a rectangular or square cross-section). If the internal reinforcing material is in the shape of a polygon (such as a triangle or square), any or all sharp corners and edges can be rounded or filleted. The reinforcing material can comprise the pure carrier polymer, such as polycaprolactone or polydioxanone. The reinforcing material can consist essentially of, or consist of, the pure carrier polymer, such as polycaprolactone or polydioxanone. The reinforcing material can comprise the carrier polymer with other components added. The reinforcing material can comprise the carrier polymer with a low agent or drug concentration (that is, the internal carrier polymer reinforcing material is carrier polymer-agent blend with an agent concentration lower than the surrounding carrier polymer-agent material). The reinforcing material can comprise the carrier polymer with no agent or drug. The reinforcing material can comprise another polymer (that is, a polymer different than the carrier polymer), such as poly lactic acid, polycarbonate, polyether ether ketone, polyethylene, or polypropylene. The reinforcing material can be a non-polymeric material.

The reinforcing material can extend axially along substantially the entire length of the segment. Alternatively, the reinforcing material can extend axially along about 50%, along at least about 50%, along about 60%, along at least about 60%, along about 70%, along at least about 70%, along about 80%, along at least about 80%, along about 90%, along at least about 90%, along about 95%, or along at least about 95%, of the entire length of the segment.

The reinforcing material is typically one continuous piece along the interior of the segment. However, reinforcing materials in two, three, or more pieces can be used, each piece extending axially along a portion of the interior of the segment.

Figure 14:
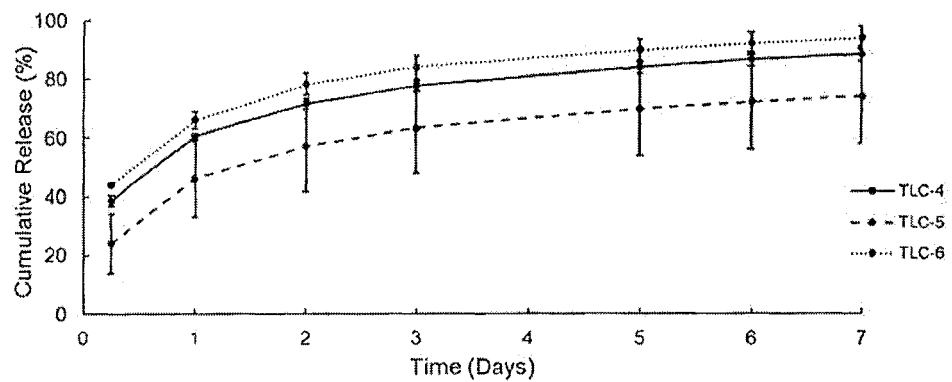
FIG. 14 shows tacrolimus release profile over time for various formulations.

Internally reinforced segments are useful for gastric residence systems which deliver hydrophobic therapeutic agents or salts thereof. Because of the low solubility of the hydrophobic agent or salt, a high proportion of agent or salt must be blended with the carrier polymer and any other excipients used. This high proportion of agent or salt can significantly lower the mechanical strength of the segment, however. Using internal reinforcement can increase the mechanical strength of the segment. In addition, since the innermost region of the segment is the most difficult region for water or gastric fluid to penetrate, replacing an interior portion of carrier polymer-therapeutic agent with reinforcing material will have a relatively small effect on drug delivery characteristics. Example 4 and the results in FIG. 14 show the use of an internally reinforced segment with the hydrophobic drug tacrolimus, where polycaprolactone arms were dipped in a solution containing tacrolimus and polyethylene vinyl acetate.

In one embodiment, the invention provides gastric residence systems for administration to the stomach of a patient, comprising an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween; wherein the proximal end of each elongate member is attached to the elastomer component and projects radially from the elastomer component, each elongate member having its distal end not attached to the elastomer component and located at a larger radial distance from the elastomer component than the proximal end; wherein at least one segment further comprises a reinforcing material, where the reinforcing material extends axially along the interior of the at least one segment; and wherein the carrier polymer-agent component comprises a hydrophobic therapeutic agent. In further embodiments, the elongate members are attached to the elastomer component via a linker region; or the elongate members comprise two or more segments, where the segments are connected by linker regions; or where the elongate members are attached to the elastomer component via a linker region and the elongate members comprise two or more segments where the segments are connect by linker regions. Each segment comprises a proximal end, a distal end, and an outer surface therebetween. In one embodiment, the hydrophobic therapeutic agent has a solubility below about 1 mg/ml in water. In one embodiment, the hydrophobic therapeutic agent has a solubility below about 500 microgram/ml in water. In one embodiment, the hydrophobic therapeutic agent has a solubility below about 250 microgram/ml in water. In one embodiment, the hydrophobic therapeutic agent has a solubility below about 100 microgram/ml in water. In one embodiment, the hydrophobic therapeutic agent has a solubility below about 50 microgram/ml in water. In one embodiment, the hydrophobic therapeutic agent has a solubility below about 25 microgram/ml in water. In one embodiment, the hydrophobic therapeutic agent has a solubility below about 10 microgram/ml in water. In one embodiment, the hydrophobic therapeutic agent has a solubility below about 5 microgram/ml in water. In one embodiment, the hydrophobic therapeutic agent has a solubility below about 1 microgram/ml in water. In one embodiment, the hydrophobic therapeutic agent has a solubility of about 1 microgram/ml to about 1 mg/ml, about 1 microgram/ml to about 500 microgram/ml, about 1 microgram/ml to about 250 microgram/ml, about 1 microgram/ml to about 100 microgram/ml, about 1 microgram/ml to about 50 microgram/ml, about 1 microgram/ml to about 25 microgram/ml, about 1 microgram/ml to about 10 microgram/ml, or about 1 microgram/ml to about 5 microgram/ml in water.

The segment with reinforcing material can be prepared by any suitable method, such as dip-coating (used in Example 4), co-extrusion, or three-dimensional printing.

Because the mechanical strength of the elongate member or segment comes mainly from the reinforcing material, not the carrier polymer, significantly more agent can be used in the carrier polymer-agent mixture while maintaining suitable mechanical strength of the elongate member than could be used in the absence of reinforcing material. Thus, the amount of agent in the carrier polymer-agent mixture can range up to about 60% by weight, up to about 50% by weight, or up to about 40% by weight, whereas without reinforcing material, such high percentages may not be attainable. Accordingly, in one embodiment, the amount of agent can range from about 1% to about 60%, about 10% to about 60%, about 20% to about 60%, about 30% to about 60%, about 40% to about 60%, about 50% to about 60%, about 1% to about 50%, about 1% to about 40%, about 1% to about 30%, about 1% to about 20%, or about 1% to about 10% by weight of the carrier polymer-agent mixture.

Again, because the reinforcing material provides the mechanical strength of the elongate member or segment, additional polymers can be used as carrier polymers which might be unsuitable for use in the absence of reinforcing material. Polyethylene vinyl acetate can be used as a carrier polymer when reinforcing material is used. Poloxamer 407, Pluronic P407, hypromellose, Kolliphor RH40, polyvinyl caprolactam, polyvinyl acetate (PVAc), polyvinylpyrrolidone (PVP), polyvinyl alcohol (PVA), polyethylene glycol (PEG), Soluplus (available from BASF; a copolymer of polyvinyl caprolactam, polyvinyl acetate, and polyethylene glycol), Copovidone, Eudragits (E, EPO, RS, RL), methyl methacrylates, Carnauba wax, poly(methyl vinyl ether-alt-maleic anhydride), polyoxyethylene alkyl ethers, polysorbates, polyoxyethylene stearates, polyvinyl acetate phthalate, alginates, polydextrose, polydioxanone, polybutylmethacrylate, poly(lactic acid), poly(glycolic acid), poly(lactic-co-glycolic acid) (PLGA), and mixtures thereof can also be used as carrier polymers in concert with reinforcement materials. Alternatively, the polymers listed as carrier polymers which can be used as carrier polymers without reinforcing material can also be used as carrier polymers with reinforcing material; those polymers, including polycaprolactone and polydioxanone, are enumerated herein in the section "Carrier polymers for carrier polymer-agent component."

Segment Composition: Fenestrated or Porous Coating as External Support

The strength of a segment can be improved by using a fenestrated (perforated) coating or layer, which functions as an external support, such as that illustrated in FIG. 9A. The coating, or external support, significantly relaxes the mechanical requirements of the carrier polymer-agent material, as it provides the principal mechanical support for the segment. Polymers that degrade rapidly enough to achieve linear drug release tend to be poor structural polymers (such as polyanhydrides). Using a structural polymer shell to reinforce such relatively poor structural carrier polymers thus obviates the problems in using such carrier polymers.

The fenestrations can be adjusted in size, number, and position to provide the desired ingress of gastric fluid, and the desired egress of agent or drug eluted out of the carrier polymer-agent blend by the gastric fluid.

FIG. 9B shows a transverse cross-section and a longitudinal view of an embodiment of an elongate member having a fenestrated coating or layer. The interior can be entirely or primarily carrier polymer-agent blend, while the external structural polymer provides support. Time-dependent linkers or enteric linkers can be used in the elongate member.

FIG. 9C shows another embodiment of an elongate member having a fenestrated coating or layer. This embodiment has less carrier polymer-drug agent in its interior than the embodiment shown in FIG. 9B. The cross-sectional area of the pores increases toward the center of the structure. The surface area for drug dissolution increases over time as material is dissolved out of the pore.

The porous shell can be created through three-dimensional printing. An islands-in-the-sea approach can be used to print a highly degradable polymer (e.g., Eudragit E, Pluronic P407) within a slowly-degradable structural polymer shell (e.g., PCL, PLA). Gastric fluid will quickly degrade and/or dissolve the islands, leaving a porous structure into which the carrier polymer-agent blend can be placed. The size of these islands (and the resulting pores after the islands dissolve) can be about 10 um to about 100 um.

The fenestrated layer can comprise any material strong enough to provide structural support, such as a thick layer of carrier polymer which lacks therapeutic agent. The fenestrated layer can comprise the pure carrier polymer, such as polycaprolactone or polydioxanone. The fenestrated layer can consist essentially of, or consist of, the pure carrier polymer, such as polycaprolactone or polydioxanone. The fenestrated layer can comprise the carrier polymer with other components added. The fenestrated layer can comprise the carrier polymer with a low agent or drug concentration (that is, the internal carrier polymer fenestrated layer is carrier polymer-agent blend with an agent concentration lower than the surrounding carrier polymer-agent material). The fenestrated layer can comprise the carrier polymer with no agent or drug. The fenestrated layer can comprise another polymer (that is, a polymer different than the carrier polymer), such as poly lactic acid, polycarbonate, polyether ether ketone, polyethylene, or polypropylene. The fenestrated layer can be a non-polymeric material.

In some embodiments, the fenestrated layer can have a thickness of about 100 micrometers to about 1,000 micrometers, such as a thickness of about 200 micrometers to 900 micrometers, about 300 micrometers to about 800 micrometers, about 400 micrometers to about 700 micrometers, about 400 micrometers to about 600 micrometers, or about 500 micrometers. In some embodiments, the fenestrated layer can have a thickness of about 100 micrometers to about 900 micrometers, about 100 micrometers to about 800 micrometers, about 100 micrometers to about 700 micrometers, about 100 micrometers to about 600 micrometers, about 100 micrometers to about 500 micrometers, about 100 micrometers to about 400 micrometers, about 100 micrometers to about 300 micrometers, about 100 micrometers to about 250 micrometers, about 100 micrometers to about 200 micrometers, about 100 micrometers to about 150 micrometers; or about 200 micrometers to about 1,000 micrometers, about 300 micrometers to about 1,000 micrometers, about 400 micrometers to about 1,000 micrometers, about 500 micrometers to about 1,000 micrometers, about 600 micrometers to about 1,000 micrometers, about 700 micrometers to about 1,000 micrometers, about 800 micrometers to about 1,000 micrometers, or about 900 micrometers to about 1,000 micrometers. In some embodiments, the fenestrated layer can have a thickness of about 200, about 300, about 400, about 500, about 600, about 700, about 800, or about 900 micrometers.

Segment Composition: External Reinforcing Layer or Exoskeleton as External Support The strength of a segment can also be improved by using an "exoskeleton" or external reinforcing layer, which functions as an external support. This external reinforcing layer is similar to the fenestrated coating, but does not surround the outer surface of the segment completely. Because the external reinforcing layer does not surround outer surface of the segment completely, it need not have fenestrations, although the external reinforcing layer can optionally have fenestrations if desired. Thus, in one embodiment, the external reinforcing layer does not have fenestrations; and in another embodiment, the external reinforcing layer has fenestrations. As with the fenestrated coating, the external reinforcing layer significantly relaxes the mechanical requirements of the carrier polymer-agent material, by providing the principal mechanical support for the segment. Segments with external reinforcing layers are described in Example 1, FIG. 11A, FIG. 11B, FIG. 11C, and FIG. 11D.

The external reinforcing layer can be applied to a portion of the surface of the segment, such that it covers about 10%, about 20%, about 25%, about 30%, about 33%, about 40%, about 50%, about 60%, about 67%, about 70%, about 75%, about 80%, or about 90% of the segment. Note that if an external reinforcing layer covers 100% of the segment, it will need to have fenestrations to permit elution of therapeutic agent, and thus becomes the fenestrated shells described previously. The external reinforcing layer should extend along a significant amount of the length of the segment in order to provide sufficient reinforcement; for example, it should extend at least about 75%, at least about 800, at least about 90%, or preferably at least about 95% of the length of the segment.

The external reinforcing layer can be tailored to the shape of the segment or elongate member which it reinforces. For example, for an elongate member or "arm" with a triangular cross section (i.e., the elongate member is a triangular prism), such as the cross-section shown at left in FIG. 2A, an external reinforcing layer can be applied to one side of the elongate member, which would then cover about one-third or about 33% of the surface of the elongate member. An external reinforcing layer covering one side of a triangular prism would have a width equal to the length of the elongate member, and a height equal to the width of the side of the triangle to which it is applied; such an external reinforcing layer would be in the shape of a rectangle, where the rectangle is the parallelogram making up one side of the elongate member. For example, a reinforcing layer applied to the leftmost side of the arm cross-section illustrated in FIG. 2A for the arm illustrated in 2B would have a length equal to $(L_1+L_2+L_3+L_4+L_5)$, and a height equal to $W_2$. Reinforcing layers can be applied to cover two sides of the elongate member, covering about two-thirds or 67% of the surface of the elongate member. For an elongate member with a square or rectangular cross-section, a rectangular reinforcing layer can be added to one, two, or three sides of the elongate member. In general, for elongate members in the shape of prisms, reinforcing layers in the shape of the parallelograms comprising the sides of the elongate members can be applied to the elongate members. Different shapes can be used for elongate members with different surface configurations; for example, a curved reinforcing layer can be used to cover the curve-shaped portion of the surface of the cross-section shown at left in FIG. 10B.

The reinforcing material can comprise any material strong enough to provide structural support, such as a thick layer of carrier polymer which lacks therapeutic agent. The reinforcing material can comprise the pure carrier polymer, such as polycaprolactone or polydioxanone. The reinforcing material can consist essentially of, or consist of, the pure carrier polymer, such as polycaprolactone or polydioxanone. The reinforcing material can comprise the carrier polymer with other components added. The reinforcing material can comprise the carrier polymer with a low agent or drug concentration (that is, the internal carrier polymer reinforcing material is carrier polymer-agent blend with an agent concentration lower than the surrounding carrier polymer-agent material). The reinforcing material can comprise the carrier polymer with no agent or drug. The reinforcing material can comprise another polymer (that is, a polymer different than the carrier polymer), such as poly lactic acid, polycarbonate, polyether ether ketone, polyethylene, or polypropylene. The reinforcing material can be a non-polymeric material.

In some embodiments, the reinforcing material can have a thickness of about 100 micrometers to about 1,000 micrometers, such as a thickness of about 200 micrometers to 900 micrometers, about 300 micrometers to about 800 micrometers, about 400 micrometers to about 700 micrometers, about 400 micrometers to about 600 micrometers, or about 500 micrometers. In some embodiments, the reinforcing material can have a thickness of about 100 micrometers to about 900 micrometers, about 100 micrometers to about 800 micrometers, about 100 micrometers to about 700 micrometers, about 100 micrometers to about 600 micrometers, about 100 micrometers to about 500 micrometers, about 100 micrometers to about 400 micrometers, about 100 micrometers to about 300 micrometers, about 100 micrometers to about 250 micrometers, about 100 micrometers to about 200 micrometers, about 100 micrometers to about 150 micrometers; or about 200 micrometers to about 1,000 micrometers, about 300 micrometers to about 1,000 micrometers, about 400 micrometers to about 1,000 micrometers, about 500 micrometers to about 1,000 micrometers, about 600 micrometers to about 1,000 micrometers, about 700 micrometers to about 1,000 micrometers, about 800 micrometers to about 1,000 micrometers, or about 900 micrometers to about 1,000 micrometers. In some embodiments, the reinforcing material can have a thickness of about 200, about 300, about 400, about 500, about 600, about 700, about 800, or about 900 micrometers.

System Dimensions

The system must be able to adopt a compacted state with dimensions that enable the patient to swallow the system (or for the system to be introduced into the stomach by alternate methods, such as a feeding tube or gastrostomy tube). Typically, the system is held in the compacted state by a container such as a capsule. Upon entry into the stomach, the system is then released from the container and adopts an uncompacted state, that is, an expanded conformation, with dimensions that prevent passage of the system through the pyloric sphincter, thus permitting retention of the system in the stomach.

Accordingly, the system should be capable of being placed inside a standard-sized capsule of the type commonly used in pharmacy. Standard capsule sizes in use in the United States are provided below in Table 1 (see "Draft Guidance for Industry on Size, Shape, and Other Physical Attributes of Generic Tablets and Capsules" at URL www.regulations.gov/#!documentDetail; D=FDA-2013-N-1434-0002). As these are the outer dimensions of the capsule, and as dimensions will vary slightly between capsule manufacturers, the system should be capable of adopting a configuration which is about 0.5 to 1 mm smaller than the outer diameter shown, and about 1 to 2 mm shorter than the length shown in Table 1.

TABLE 1

| Capsule Size | Outer Diameter (mm) | Length (mm) |
| --- | --- | --- |
| 000 | 9.9 | 26.1 |
| 00 | 8.5 | 23.3 |
| 0 | 7.6 | 21.7 |
| 1 | 6.9 | 19.4 |
| 2 | 6.3 | 18.0 |
| 3 | 5.8 | 15.9 |
| 4 | 5.3 | 14.3 |
| 5 | 4.9 | 11.1 |

Capsules can be made of materials well-known in the art, such as gelatin or hydroxypropyl methylcellulose. In one embodiment, the capsule is made of a material that dissolves in the gastric environment, but not in the oral or esophageal environment, which prevents premature release of the system prior to reaching the stomach.

In one embodiment, the system will be folded or compressed into a compacted state in order to fit into the capsule. Once the capsule dissolves in the stomach, the system will adopt a configuration suitable for gastric retention. Preferred capsule sizes are 00 and 00el (a 00e1-size capsule has the approximate length of a 000 capsule and the approximate width of a 00 capsule), which then places constraints on the length and diameter of the folded system.

Once released from the container, the system adopts an uncompacted state with dimensions suitable to prevent passage of the gastric residence system through the pyloric sphincter. In one embodiment, the system has at least two perpendicular dimensions, each of at least 2 cm in length; that is, the gastric residence system measures at least about 2 cm in length over at least two perpendicular directions. In one embodiment, the perimeter of the system in its uncompacted state, when projected onto a plane, has two perpendicular dimensions, each of at least 2 cm in length. The two perpendicular dimensions can independently have lengths of from about 2 cm to about 7 cm, about 2 cm to about 6 cm, about 2 cm to about 5 cm, about 2 cm to about 4 cm, about 2 cm to about 3 cm, about 3 cm to about 7 cm, about 3 cm to about 6 cm, about 3 cm to about 5 cm, about 3 cm to about 4 cm, about 4 cm to about 7 cm, about 4 cm to about 6 cm, about 4 cm to about 5 cm, or about 4 cm to about 4 cm. These dimensions prevent passage of the gastric residence system through the pyloric sphincter.

For star-shaped polymer system with N arms (where N is greater than or equal to three), the arms can have dimensions such that the system has at least two perpendicular dimensions, each of length as noted above. These two perpendicular dimensions are chosen as noted above in order to promote retention of the gastric residence system. The number of arms in a star-shaped (stellate) gastric residence system should be at least three. The number of arms can be three, four, five, six, seven, eight, nine, or ten. The number of arms can be four, five, six, seven, or eight. A preferred number of arms (elongate members) for a stellate gastric residence system is six.

The system is designed to eventually break apart in the stomach at the end of the desired residence time. Once the coupling polymers break, the remaining components of the system are of dimensions that permit passage of the system through the pyloric sphincter, small intestine, and large intestine. Finally, the system is eliminated from the body by defecation, or by eventual complete dissolution of the system in the small and large intestines.

System Polymeric Composition

The choice of the individual polymers for the carrier polymer, coupling polymer, and elastomer influence many properties of the system, such as therapeutic agent elution rate (dependent on the carrier polymer, as well as other factors), the residence time of the system (dependent on the degradation of any of the polymers, principally the coupling polymers), the uncoupling time of the system if it passes into the intestine (dependent primarily on the enteric degradation rate of the coupling polymer, as discussed herein), and the shelf life of the system in its compressed form (dependent primarily on properties of the elastomer). As the systems will be administered to the gastrointestinal tract, all of the system components should be biocompatible with the gastrointestinal environment.

The rate of elution of therapeutic agent from the carrier polymer-agent component is affected by numerous factors, including the composition and properties of the carrier polymer, which may itself be a mixture of several polymeric and non-polymeric components; the properties of the therapeutic agent such as hydrophilicity/hydrophobicity, charge state, pKa, and hydrogen bonding capacity; and the properties of the gastric environment. In the aqueous environment of the stomach, avoiding burst release of a therapeutic agent (where burst release refers to a high initial delivery of active pharmaceutical ingredient upon initial deployment of the system in the stomach), particularly a hydrophilic agent, and maintaining sustained release of the agent over a period of time of days to weeks is challenging.

The residence time of the systems in the stomach is adjusted by the choice of coupling polymers used in the linker regions. The systems will eventually break down in the stomach, despite the use of enteric coupling polymers, as the mechanical action of the stomach and fluctuating pH will eventually weaken the enteric coupling polymers. Coupling polymers which degrade in a time-dependent manner in the stomach can also be used to adjust the time until the system breaks apart, and hence adjust the residence time. Once the system breaks apart, it passes into the intestines and is then eliminated.

The elastomer used in the systems is central to the shelf life of the systems. When the systems are compressed, the elastomer is subjected to mechanical stress. The stress in turn can cause polymer creep, which, if extensive enough, can prevent the systems from returning to their uncompacted configurations when released from the capsules or other container; this in turn would lead to premature passage of the system from the stomach. Polymer creep can also be temperature dependent, and therefore the expected storage conditions of the systems also need to be considered when choosing the elastomer and other polymer components.

The system components and polymers should not swell, or should have minimal swelling, in the gastric environment. The components should swell no more than about 20%, no more than about 10%, or preferably no more than about 5% when in the gastric environment over the period of residence.

Carrier Polymers for Carrier Polymer-Agent Component

The carrier polymer-agent component contains the therapeutic agent (or a salt of a therapeutic agent) to be eluted from the gastric residence system in the gastric environment. Therapeutic agent is blended into the carrier polymer to form a carrier polymer-agent mixture. This mixture can be formed into the desired shape or shapes for use as carrier polymer-agent components in the systems.

Preferably, carrier polymers have the following characteristics. They should be thermoplastic, to allow extrusion using hot melt extrusion or 3D printing techniques. They should also have a high enough melt strength and viscosity to enable extrusion into the required geometry. They should have low melting temperatures (for example, less than about 120° C.), to avoid exposing agents or drugs to high temperatures during manufacture. They should have sufficient mechanical strength (Young's modulus, compression strength, tensile strength) to avoid breaking in the stomach during the desired residence period. They should be capable of forming stable blends with agents, therapeutic agents, drugs, excipients, dispersants, and other additives.

Exemplary carrier polymers suitable for use in this invention include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly(vinyl pyrrolidone), ethylene/vinyl alcohol copolymer, poly(vinyl alcohol), carboxyvinyl polymer (Carbomer), Carbopol® acidic carboxy polymer, polycarbophil, poly(ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly(ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a preferred carrier polymer. In another embodiment, polydioxanone is used as the carrier polymer.

Other excipients can be added to the carrier polymers to modulate the release of therapeutic agent. Such excipients can be added in amounts from about 1% to 15%, preferably from about 5% to 10%, more preferably about 5% or about 10%. Examples of such excipients include Poloxamer 407 (available as Kolliphor P407, Sigma Cat #62035); Pluronic P407; Eudragit E, Eudragit EPO (available from Evonik); hypromellose (available from Sigma, Cat #H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), and Soluplus (available from BASF; a copolymer of polyvinyl caprolactam, polyvinyl acetate, and polyethylene glycol). Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. Preferred insoluble, swellable excipients include crospovidone, croscarmellose, hypromellose acetate succinate (HPMCAS), and carbopol.

Methods of Manufacture of Carrier Polymer-Agent Components

Blending temperatures for incorporation of the therapeutic agent into polymeric matrices typically range from about 80° C. to about 120° C., although higher or lower temperatures can be used for polymers which are best blended at temperatures outside that range. When agent particles of a particular size are used, and it is desired that the size of the particles be maintained during and after blending, blending can be done at temperatures below the melting point of the agent, so as to maintain the desired size of the agent. Otherwise, temperatures can be used which melt both the polymer and the agent. Blending temperatures should be below the degradation temperature of the agent. In one embodiment, less than about 0.05% of the agent is degraded during manufacture. In one embodiment, less than about 0.04% of the agent is degraded during manufacture. In one embodiment, less than about 0.03% of the agent is degraded during manufacture. In one embodiment, less than about 0.02% of the agent is degraded during manufacture. In one embodiment, less than about 0.01% of the agent is degraded during manufacture.

Hot melt extrusion can be used to prepare the carrier polymer-agent components. Single-screw or, preferably, twin-screw systems can be used. As noted, if it is desired that the size of the particles be maintained during and after blending, carrier polymers should be used which can be melted at temperatures which do not degrade the agent. Otherwise, temperatures can be used which melt both the polymer and the agent.

Melting and casting can also be used to prepare the carrier polymer-agent components. The carrier polymer and therapeutic agent, and any other desired components, are mixed together. The carrier polymer is melted and the melt is mixed so that the agent particles are evenly distributed in the melt, poured into a mold, and allowed to cool.

Solvent casting can also be used to prepare the carrier polymer-agent components. The polymer is dissolved in a solvent, and particles of therapeutic agent are added. If the size of the agent particles are to be maintained, a solvent should be used which does not dissolve the agent particles, so as to avoid altering the size characteristics of the particles; otherwise, a solvent which dissolves both the polymer and agent particles can be used. The solvent-carrier polymer-agent particle mixture (or solvent-carrier particle-agent solution), is then mixed to evenly distribute the particles (or thoroughly mix the solution), poured into a mold, and the solvent is evaporated.

Manufacture of Feed Polymers for Three-Dimensional Printing

Three-dimensional printing is often accomplished by feeding a rod or fiber of a solid material to a print head, where it is melted and deposited with subsequent solidification, in a technique known as fused deposition modeling (sometimes also called extrusion deposition); see U.S. Pat. Nos. 5,121,329 and 5,340,433. The methods described herein for the manufacture of carrier polymer-agent components can also be used to manufacture feed material, which can be used in the manufacture via three-dimensional printing of components of the gastric residence systems.

Therapeutic Agent Particle Size and Milling

Control of particle size used in the gastric residence systems is important for both optimal therapeutic agent release and mechanical stability of the systems. The particle size of the therapeutic agents affects the surface area of the agents available for dissolution when gastric fluid permeates the carrier polymer-agent components of the system. Also, as the "arms" (elongate members) of the systems are relatively thin in diameter (for example, 1 millimeter to 5 millimeters), the presence of an agent particle of a size in excess of a few percent of the diameter of the arms will result in a weaker arm, both before the agent elutes from the device, and after elution when a void is left in the space formerly occupied by the agent particle. Such weakening of the arms is disadvantageous, as it may lead to premature breakage and passage of the system before the end of the desired residence period.

In one embodiment, the therapeutic agent particles used for blending into the carrier polymer-agent components are smaller than about 100 microns in diameter. In some embodiments, the therapeutic agent particles are smaller than about 75 microns in diameter. In some embodiments, the therapeutic agent particles are smaller than about 50 microns in diameter. In some embodiments, the therapeutic agent particles are smaller than about 40 microns in diameter. In some embodiments, the therapeutic agent particles are smaller than about 30 microns in diameter. In some embodiments, the therapeutic agent particles are smaller than about 25 microns in diameter. In some embodiments, the therapeutic agent particles are smaller than about 20 microns in diameter. In some embodiments, the therapeutic agent particles are smaller than about 10 microns in diameter. In some embodiments, the therapeutic agent particles are smaller than about 5 microns in diameter.

In one embodiment, at least about 80% of the therapeutic agent particles used for blending into the carrier polymer-agent components are smaller than about 100 microns in diameter. In some embodiments, at least about 80% of the therapeutic agent particles are smaller than about 75 microns in diameter. In some embodiments, at least about 80% of the therapeutic agent particles are smaller than about 50 microns in diameter. In some embodiments, at least about 80% of the therapeutic agent particles are smaller than about 40 microns in diameter. In some embodiments, at least about 80% of the therapeutic agent particles are smaller than about 30 microns in diameter. In some embodiments, at least about 80% of the therapeutic agent particles are smaller than about 25 microns in diameter. In some embodiments, at least about 80% of the therapeutic agent particles are smaller than about 20 microns in diameter. In some embodiments, at least about 80% of the therapeutic agent particles are smaller than about 10 microns in diameter. In some embodiments, at least about 80% of the therapeutic agent particles are smaller than about 5 microns in diameter.

In one embodiment, at least about 80% of the mass of therapeutic agent particles used for blending into the carrier polymer-agent components have sizes between about 1 micron and about 100 microns in diameter. In some embodiments, at least about 80% of the mass of therapeutic agent particles have sizes between about 1 micron and about 75 microns in diameter. In some embodiments, at least about 80% of the mass of therapeutic agent particles have sizes between about 1 micron and about 50 microns in diameter. In some embodiments, at least about 80% of the mass of therapeutic agent particles have sizes between about 1 micron and about 40 microns in diameter. In some embodiments, at least about 800, of the mass of therapeutic agent particles have sizes between about 1 micron and about 30 microns in diameter. In some embodiments, at least about 80% of the mass of therapeutic agent particles have sizes between about 1 micron and about 25 microns in diameter. In some embodiments, at least about 80% of the mass of therapeutic agent particles have sizes between about 1 micron and about 20 microns in diameter. In some embodiments, at least about 80% of the mass of therapeutic agent particles have sizes between about 1 micron and about 10 microns in diameter. In some embodiments, at least about 80% of the mass of therapeutic agent particles have sizes between about 1 micron and about 5 microns in diameter.

In one embodiment, at least about 80% of the mass of therapeutic agent particles used for blending into the carrier polymer-agent components have sizes between about 2 microns and about 100 microns in diameter. In some embodiments, at least about 80% of the mass of therapeutic agent particles have sizes between about 2 microns and about 75 microns in diameter. In some embodiments, at least about 80% of the mass of therapeutic agent particles have sizes between about 2 microns and about 50 microns in diameter. In some embodiments, at least about 80% of the mass of therapeutic agent particles have sizes between about 2 microns and about 40 microns in diameter. In some embodiments, at least about 80% of the mass of therapeutic agent particles have sizes between about 2 microns and about 30 microns in diameter. In some embodiments, at least about 80% of the mass of therapeutic agent particles have sizes between about 2 microns and about 25 microns in diameter. In some embodiments, at least about 80% of the mass of therapeutic agent particles have sizes between about 2 microns and about 20 microns in diameter. In some embodiments, at least about 80% of the mass of therapeutic agent particles have sizes between about 2 microns and about 10 microns in diameter. In some embodiments, at least about 80% of the mass of therapeutic agent particles have sizes between about 2 microns and about 5 microns in diameter.

In one embodiment, at least about 80% of the mass of therapeutic agent particles used for blending into the carrier polymer-agent components have sizes between about 5 microns and about 100 microns in diameter. In some embodiments, at least about 80% of the mass of therapeutic agent particles have sizes between about 5 microns and about 75 microns in diameter. In some embodiments, at least about 80% of the mass of therapeutic agent particles have sizes between about 5 microns and about 50 microns in diameter. In some embodiments, at least about 80% of the mass of therapeutic agent particles have sizes between about 5 microns and about 40 microns in diameter. In some embodiments, at least about 80% of the mass of therapeutic agent particles have sizes between about 5 microns and about 30 microns in diameter. In some embodiments, at least about 80% of the mass of therapeutic agent particles have sizes between about 5 microns and about 25 microns in diameter. In some embodiments, at least about 80% of the mass of therapeutic agent particles have sizes between about 5 microns and about 20 microns in diameter. In some embodiments, at least about 800 of the mass of therapeutic agent particles have sizes between about 5 microns and about 10 microns in diameter.

The particle size of the therapeutic agents can be readily adjusted by milling. Several milling techniques are available to reduce larger particles to smaller particles of desired size. Fluid energy milling is a dry milling technique which uses inter-particle collisions to reduce the size of particles. A type of fluid energy mill called an air jet mill shoots air into a cylindrical chamber in a manner so as to maximize collision between therapeutic agent particles. Ball milling utilizes a rolling cylindrical chamber which rotates around its principal axis. The therapeutic agent and grinding material (such as steel balls, made from chrome steel or CR—NI steel; ceramic balls, such as zirconia; or plastic polyamides) collide, causing reduction in particle size of the agent. Ball milling can be performed in either the dry state, or with liquid added to the cylinder where the therapeutic agent and the grinding material are insoluble in the liquid. Further information regarding milling is described in the chapter by R. W. Lee et al. entitled "Particle Size Reduction" in *Water-Insoluble Drug Formulation, Second Edition* (Ron Liu, editor), Boca Raton, Florida: CRC Press, 2008; and in the chapter by A. W. Brzeczko et al. entitled "Granulation of Poorly Water-Soluble Drugs" in *Handbook of Pharmaceutical Granulation Technology, Third Edition* (Dilip M. Parikh, editor), Boca Raton, Florida: CRC Press/Taylor & Francis Group, 2010 (and other sections of that handbook). Fluid energy milling (i.e., air jet milling) is a preferred method of milling, as it is more amenable to scale-up compared to other dry milling techniques such as ball milling.

Milling Additives

Substances can be added to the therapeutic agent material during milling to assist in obtaining particles of the desired size, and minimize aggregation during handling. Silica (silicon dioxide, $SiO_2$) is a preferred milling additive, as it is inexpensive, widely available, and non-toxic. Other additives which can be used include silica, calcium phosphate, powdered cellulose, colloidal silicon dioxide, hydrophobic colloidal silica, magnesium oxide, magnesium silicate, magnesium trisilicate, talc, polyvinylpyrrolidone, cellulose ethers, polyethylene glycol, polyvinyl alcohol, and surfactants. In particular, hydrophobic particles less than 5 microns in diameter are particularly prone to agglomeration, and hydrophilic additives are used when milling such particles. A weight/weight ratio of about 0.1% to about 5% of milling additive, such as silica, can be used for fluid milling or ball milling, or about 0.1% to about 4%, about 0.1% to about 3%, about 0.1% to about 2%, about 0.1% to about 1%, about 1% to about 5%, about 1% to about 4%, about 1% to about 3° %, about 1% to about 2%, or about 0.1%, about 0.5%, about 1%, about 2%, about 3%, about 4% or about 5%.

Particle Sizing

After milling, particles can be passed through meshes of appropriate size to obtain particles of the desired size. To obtain particles of a desired maximum size, particles are passed through a mesh with holes of the maximum size desired; particles which are too large will be retained on the mesh, and particles which pass through the mesh will have the desired maximum size. To obtain particles of a desired minimum size, particles are passed through a mesh with holes of the minimum size desired; particles which pass through the mesh are too small, and the desired particles will be retained on the mesh.

Dispersants for Modulation of Therapeutic Agent Release and Stability of Polymer Blend The use of a dispersant in the carrier polymer-agent component provides numerous advantages. The rate of elution of therapeutic agent from the carrier polymer-agent component is affected by numerous factors as previously noted, including the composition and properties of the carrier polymer (which may itself comprise multiple polymeric and non-polymeric components); the physical and chemical properties of the therapeutic agent; and the gastric environment. Avoiding burst release of therapeutic agent, especially hydrophilic agents, and maintaining sustained release of the therapeutic agent over the residence period is an important characteristic of the systems. The use of a dispersant according to the invention enables better control of release rate and suppression of burst release. Burst release and release rate can be tuned by using varied concentrations of dispersant.

Dispersants which can be used in the invention include: silicon dioxide (silica, $SiO_2$) (hydrophilic fumed); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant.

In addition to anti-aggregation/anti-flocculation activity, the dispersant can help prevent phase separation during fabrication and/or storage of the systems. This is particularly useful for manufacture of the systems by hot melt extrusion.

The weight/weight ratio of dispersant to therapeutic agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can also be used to modulate the amount of burst release during the initial period when the gastric residence system is administered. In embodiments of a gastric residence system that is to be administered once weekly, the burst release over the approximately first six hours after initial administration is less than about 8%, preferably less than about 6%, of the total amount of drug in the system. In embodiments of a gastric residence system that is to be administered once every three days, the burst release over the approximately first six hours after initial administration is less than about 12%, preferably less than about 10%, of the total amount of drug in the system. In embodiments of a gastric residence system that is to be administered once daily, the burst release over the approximately first six hours after initial administration is less than about 40%, preferably less than about 30%, of the total amount of drug in the system. In general, if a new gastric residence system is administered every D days, and the total mass of drug is M, then the gastric residence system releases less than about [(M divided by D) times 0.5], preferably less than about [(M divided by D) multiplied by 0.4], or less than about [(M divided by D) multiplied by ⅜], more preferably less than about [(M divided by D) multiplied by 0.3], over the approximately first six hours after initial administration. In further embodiments, the gastric residence system releases at least about [(M divided by D) multiplied by 0.25] over the approximately first six hours after initial administration, that is, the system releases at least about one-quarter of the daily dosage over the first one-quarter of the first day of administration.

Coupling Polymers

The coupling polymer is used to link one or more carrier polymer-agent components to one or more carrier polymer-agent components, to link one or more carrier polymer-agent components to one or more elastomer components, or to link one or more elastomer components to one or more elastomer components. Thus, the coupling polymers form linker regions between other components of the system. Enteric polymers and time-dependent polymers are preferred for use as coupling polymers.

Enteric polymers are relatively insoluble under acidic conditions, such as the conditions encountered in the stomach, but are soluble under the less acidic to basic conditions encountered in the small intestine. Enteric polymers which dissolve at about pH 5 or above can be used as coupling polymers, as the pH of the initial portion of the small intestine, the duodenum, ranges from about 5.4 to 6.1. If the gastric residence system passes intact through the pyloric valve, the enteric coupling polymer will dissolve and the components linked by the coupling polymer will break apart, allowing passage of the residence system through the small and large intestines. Thus, the gastric residence systems are designed to uncouple rapidly in the intestinal environment by dissolution of the coupling polymer, within 48 hours, preferably within 24 hours, more preferably within 12 hours, yet more preferably within 1-2 hours, so as to avoid potential intestinal blockage. If, during treatment, the gastric residence system must be removed quickly for any reason, the patient can drink a mildly basic aqueous solution (such as a bicarbonate solution) in order to induce immediate de-coupling of the gastric residence system.

Exemplary coupling polymers include, but are not limited to, cellulose acetate phthalate, cellulose acetate succinate, methylcellulose phthalate, ethyl hydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and copolymers, mixtures, blends and combinations thereof. Some of the enteric polymers that can be used in the invention are listed in Table 2, along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Röhm GmbH, Darmstadt, Germany) is a preferred enteric polymer. Cellulose acetate phthalate, cellulose acetate succinate, and hydroxypropyl methylcellulose phthalate are also suitable enteric polymers.

In one embodiment, the enteric polymers used in the gastric residence system dissolve at a pH above about 4. In some embodiments, the enteric polymers used in the gastric residence system dissolve at a pH above about 5. In some embodiments, the enteric polymers used in the gastric residence system dissolve at a pH above about 6. In some embodiments, the enteric polymers used in the gastric residence system dissolve at a pH above about 7. In some embodiments, the enteric polymers used in the gastric residence system dissolve at a pH above about 7.5. In some embodiments, the enteric polymers used in the gastric residence system dissolve at a pH between about 4 and about 5. In some embodiments, the enteric polymers used in the gastric residence system dissolve at a pH between about 4 and about 6. In some embodiments, the enteric polymers used in the gastric residence system dissolve at a pH between about 4 and about 7. In some embodiments, the enteric polymers used in the gastric residence system dissolve at a pH between about 4 and about 7.5. In some embodiments, the enteric polymers used in the gastric residence system dissolve at a pH between about 5 and about 6. In some embodiments, the enteric polymers used in the gastric residence system dissolve at a pH between about 5 and about 7. In some embodiments, the enteric polymers used in the gastric residence system dissolve at a pH between about 5 and about 7.5. In some embodiments, the enteric polymers used in the gastric residence system dissolve at a pH between about 6 and about 7. In some embodiments, the enteric polymers used in the gastric residence system dissolve at a pH between about 6 and about 7.5.

TABLE 2

| Polymer | Dissolution pH |
| --- | --- |
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer | 6.0 |

TABLE 2-continued

| Polymer | Dissolution pH |
|---|---|
| (1:1) Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

Additional preferred polymers for use as coupling polymers are time-dependent polymers, that is, polymers that degrade in a time-dependent manner in the gastric environment. For example, triacetin degrades in a time-dependent manner over seven days in simulated gastric fluid, while Plastoid B retains its strength over a seven-day period in simulated gastric fluid. Thus, a polymer that degrades in a time-dependent manner can be readily prepared by mixing Plastoid B and triacetin; the degradation time of the Plastoid B-triacetin mixture can be extended by increasing the amount of Plastoid B used in the mixture, while the degradation time can be decreased by increasing the amount of Plastoid B used in the mixture.

A variety of time-dependent mechanisms are available. Water-soluble time-dependent polymers break down as water penetrates through the polymer. Examples of such polymers are hydroxypropyl methylcellulose and poly vinyl acetate. Acid soluble time-dependent polymers break down over time in an acidic environment. Examples include Eudragit EPO. Time-dependent polymers can use water soluble plasticizers; as plasticizer is released, the remaining polymer becomes brittle and breaks under gastric forces. Examples of such polymers include triacetin and triethyl citrate.

In some embodiments, the carrier polymer-agent components are elongate members comprised of segments attached by enteric polymers. In some embodiments, the carrier polymer-agent components are attached to the elastomer component of the system by enteric polymers. In any of these embodiments, when enteric polymers are used for both segment-to-segment attachments and for attachment of the elongate members to the elastomeric component, the enteric polymer used for segment-segment attachments can be the same enteric polymer as the enteric polymer used for attachment of the elongate members to the elastomeric component, or the enteric polymer used for segment-segment attachments can be a different enteric polymer than the enteric polymer used for attachment of the elongate members to the elastomeric component. The enteric polymers used for the segment-segment attachments can all be the same enteric polymer, or can all be different enteric polymers, or some enteric polymers in the segment-segment attachments can be the same and some enteric polymers in the segment-segment attachments can be different. That is, the enteric polymer(s) used for each segment-segment attachment and the enteric polymer used for attachment of the elongate members to the elastomeric component can be independently chosen.

In any of the embodiments of the gastric residence systems described herein, the coupling polymers or linkers can comprise hydroxypropyl methyl cellulose acetate succinate (HPMCAS) and polycaprolactone (PCL). These blends can be used to form disintegrating linkers or disintegrating matrices. The ratio of HPMCAS to polycaprolactone in the disintegrating linker or disintegrating matrix can be between about 80% HPMCAS:20% PCL to about 20% HPMCAS:80% PCL. the ratio of HPMCAS to polycaprolactone can be between about 80% HPMCAS:20% PCL to about 20% HPMCAS:80% PCL; between about 70% HPMCAS:30% PCL to about 30% HPMCAS:70% PCL; between about 60% HPMCAS:40% PCL to about 40% HPMCAS:60% PCL; between about 80 HPMCAS:20% PCL to about 50% HPMCAS:50% PCL; between about 80% HPMCAS:20% PCL to about 60% HPMCAS:40% PCL; between about 70% HPMCAS:30% PCL to about 50% HPMCAS:50% PCL; between about 70% HPMCAS:30% PCL to about 60% HPMCAS:40% PCL; between about 20% HPMCAS:80% PCL to about 40% HPMCAS:60% PCL; between about 20% HPMCAS:80% PCL to about 50% HPMCAS:50% PCL; between about 30% HPMCAS:70% PCL to about 40% HPMCAS:60% PCL; between about 30% HPMCAS:70% PCL to about 50% HPMCAS:50% PCL; or about 80% HPMCAS:20% PCL, about 70% HPMCAS:30% PCL, about 60% HPMCAS:40% PCL, about 50% HPMCAS:50% PCL, about 40% HPMCAS:60% PCL, about 30% HPMCAS:70% PCL, or about 20% HPMCAS:80% PCL. The linker can further comprise a plasticizer selected from the group consisting of triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, and diacetylated monoglycerides.

The linkers are chosen to weaken sufficiently after a specified period of time in order to allow the gastric residence systems to reach a point where they de-couple and pass through the pylorus and out of the stomach after the desired residence period, that is, they linkers weaken to the point of uncoupling or to the point where the gastric residence system can pass through the pylorus, referred to as the uncoupling or pyloric passage point. Thus, in one embodiment, linkers are used that uncouple after about two days in a human stomach; after about three days in a human stomach; after about four days in a human stomach; after about five days in a human stomach; after about six days in a human stomach; after about seven days in a human stomach; after about eight days in a human stomach; after about nine days in a human stomach; after about ten days in a human stomach; or after about two weeks in a human stomach. In one embodiment, linkers are used that uncouple after about two days in a dog stomach; after about three days in a dog stomach; after about four days in a dog stomach; after about five days in a dog stomach; after about six days in a dog stomach; after about seven days in a dog stomach; after about eight days in a dog stomach; after about nine days in a dog stomach; after about ten days in a dog stomach; or after about two weeks in a dog stomach. In one embodiment, linkers are used that uncouple after about two days in a pig stomach; after about three days in a pig stomach; after about four days in a pig stomach; after about five days in a pig stomach; after about six days in a pig stomach; after about seven days in a pig stomach; after about eight days in a pig stomach; after about nine days in a pig stomach; after about ten days in a pig stomach; or after about two weeks in a pig stomach. In one embodiment, linkers are used that uncouple after about two days in fasted-state simulated gastric fluid; after about three days in fasted-state simulated gastric fluid; after about four days in fasted-state simulated gastric fluid; after about five days in fasted-state simulated gastric fluid; after about six days in fasted-state simulated gastric fluid; after about seven days in fasted-state simulated gastric fluid; after about eight days in fasted-state simulated gastric fluid; after about nine days in fasted-state simulated gastric fluid; after about ten days in fasted-state simulated gastric fluid; or after about two weeks in fasted-state simulated gastric fluid. In one embodiment, linkers are used that uncouple after about two days in fed-state simulated gastric fluid; after about three days in fed-state simulated gastric fluid; after about four days in fed-state simulated gastric fluid; after about five days in fed-state simulated gastric fluid; after about six days in fed-state simulated gastric fluid; after about seven days in fed-state simulated gastric fluid; after about eight days in fed-state simulated gastric fluid; after about nine days in fed-state simulated gastric fluid; after about ten days in fed-state simulated gastric fluid; or after about two weeks in fed-state simulated gastric fluid. In one embodiment, linkers are used that uncouple after about two days in water at pH 2; after about three days in water at pH 2; after about four days in water at pH 2; after about five days in water at pH 2; after about six days in water at pH 2; after about seven days in water at pH 2; after about eight days in water at pH 2; after about nine days in water at pH 2; after about ten days in water at pH 2; or after about two weeks in water at pH 2. In one embodiment, linkers are used that uncouple after about two days in water at pH 1; after about three days in water at pH 1; after about four days in water at pH 1; after about five days in water at pH 1; after about six days in water at pH 1; after about seven days in water at pH 1; after about eight days in water at pH 1; after about nine days in water at pH 1; after about ten days in water at pH 1; or after about two weeks in water at pH 1.

The de-coupling or pyloric passage point in human, dog, or pig occurs when the system passes out of the stomach, that is, when it passes through the pylorus. For the in vitro measurements in simulated gastric fluid or acidic water, the de-coupling or pyloric passage point occurs when the linker weakens to the point where it will break under the normal compressive forces of the stomach, typically about 0.1 Newton to 0.2 Newton. Linkage strength (breaking point) can be measured by any relevant test that serves to test coupling ability, that is, the force required to break the linker, such as the four-point bending flexural test (ASTM D790) described in Example 18 of WO 2017/070612, or Examples 12, 13, 15, 17, or 18 of PCT/US2016/065453. In one embodiment, the de-coupling or pyloric passage point is reached when the linkers uncouple at about 0.2 N of force. In another embodiment, the de-coupling or pyloric passage point is reached when the linkers uncouple at about 0.1 N of force.

Elastomers

Elastomers (also referred to as elastic polymers or tensile polymers) enable the gastric residence system to be compacted, such as by being folded or compressed, into a form suitable for administration to the stomach by swallowing a container or capsule containing the compacted system. Upon dissolution of the capsule in the stomach, the gastric residence system expands into a shape which prevents passage of the system through the pyloric sphincter of the patient for the desired residence time of the system. Thus, the elastomer must be capable of being stored in a compacted configuration in a capsule for a reasonable shelf life, and of expanding to its original shape, or approximately its original shape, upon release from the capsule. In one embodiment, the elastomer is a silicone elastomer. In one embodiment, the elastomer is formed from a liquid silicone rubber, such as sold in the Dow Corning QP-1 liquid silicone rubber kit. In one embodiment, the elastomer is crosslinked polycaprolactone. In one embodiment, the elastomer is an enteric polymer, such as those listed in Table 2. In some embodiments, the coupling polymer(s) used in the system are also elastomers. Elastomers are preferred for use as the central polymer in the star-shaped or stellate design of the gastric residence systems.

In one embodiment, both the coupling polymer and elastomer are enteric polymers, which provides for more complete breakage of the system into the carrier polymer-agent pieces if the system enters the intestine, or if the patient drinks a mildly basic solution in order to induce passage of the system.

Examples of elastomers which can be used include silicones, such as those formed using Dow Corning QP-1 kits; urethane-cross-linked polycaprolactones, poly(acryloyl 6-aminocaproic acid) (PA6ACA); poly(methacrylic acid-co-ethyl acrylate) (EUDRAGIT L 100-55); and mixtures of poly(acryloyl 6-aminocaproic acid) (PA6ACA) and poly (methacrylic acid-co-ethyl acrylate) (EUDRAGIT L 100-55).

Other System Characteristics
Stabilization of Therapeutic Agents

Many therapeutic agents are prone to oxidative degradation when exposed to reactive oxygen species, which can be present in the stomach. A therapeutic agent contained in the system may thus oxidize due to the prolonged residence in the stomach of the system, and the extended release period of agent from the system. Accordingly, it is desirable to stabilize the agent to prevent oxidative and other degradation.

Anti-oxidant stabilizers that can be included in the systems to reduce or prevent oxidation of the therapeutic agent include alpha-tocopherol (about 0.01 to about 0.05% v/v), ascorbic acid (about 0.01 to about 0.1% w/v), ascorbyl palmitate (about 0.01 to about 0.1% w/v), butylated hydroxytoluene (about 0.01 to about 0.1% w/w), butylated hydroxyanisole (about 0.01 to about 0.1% w/w), and fumaric acid (up to 3600 ppm).

Certain therapeutic agents can be pH-sensitive, especially at the low pH present in the gastric environment. Stabilizer compounds that can be included in the systems to reduce or prevent degradation of therapeutic agent at low pH include calcium carbonate, calcium lactate, calcium phosphate, sodium phosphate, and sodium bicarbonate. They are typically used in an amount of up to about 2% w/w.

The anti-oxidant stabilizers, pH stabilizers, and other stabilizer compounds are blended into the polymers containing the therapeutic agent by blending the stabilizer(s) into the molten carrier polymer-agent mixture. The stabilizer(s) can be blended into molten carrier polymer prior to blending the therapeutic agent into the polymer-stabilizer mixture; or the stabilizer(s) can be blended with therapeutic agent prior to formulation of the blended therapeutic agent-stabilizer mixture in the carrier polymer; or stabilizer(s), therapeutic agent, and molten carrier polymer can be blended simultaneously. Therapeutic agent can also be blended with molten carrier polymer prior to blending the stabilizer(s) into the polymer-agent mixture.

In one embodiment, less than about 10% of the therapeutic agent remaining in the system is degraded or oxidized after a gastric residence period of about 24 hours. In one embodiment, less than about 10% of the therapeutic agent remaining in the system is degraded or oxidized after a gastric residence period of about 48 hours. In one embodiment, less than about 10% of the therapeutic agent remaining in the system is degraded or oxidized after a gastric residence period of about 72 hours. In one embodiment, less than about 10% of the therapeutic agent remaining in the system is degraded or oxidized after a gastric residence period of about 96 hours. In one embodiment, less than about 10% of the therapeutic agent remaining in the system is degraded or oxidized after a gastric residence period of about five days. In some embodiments, less than about 10% of the therapeutic agent remaining in the system is degraded or oxidized after a gastric residence period of about a week. In some embodiments, less than about 10% of the therapeutic agent remaining in the system is degraded or oxidized after a gastric residence period of about two weeks. In some embodiments, less than about 10% of the therapeutic agent remaining in the system is degraded or oxidized after a gastric residence period of about three weeks. In some embodiments, less than about 10% of the therapeutic agent remaining in the system is degraded or oxidized after a gastric residence period of about four weeks. In some embodiments, less than about 10% of the therapeutic agent remaining in the system is degraded or oxidized after a gastric residence period of about a month.

In one embodiment, less than about 5% of the therapeutic agent remaining in the system is degraded or oxidized after a gastric residence period of about 24 hours. In one embodiment, less than about 5% of the therapeutic agent remaining in the system is degraded or oxidized after a gastric residence period of about 48 hours. In one embodiment, less than about 5% of the therapeutic agent remaining in the system is degraded or oxidized after a gastric residence period of about 72 hours. In one embodiment, less than about 5% of the therapeutic agent remaining in the system is degraded or oxidized after a gastric residence period of about 96 hours. In one embodiment, less than about 5% of the therapeutic agent remaining in the system is degraded or oxidized after a gastric residence period of about five days. In some embodiments, less than about 5% of the therapeutic agent remaining in the system is degraded or oxidized after a gastric residence period of about a week. In some embodiments, less than about 5% of the therapeutic agent remaining in the system is degraded or oxidized after a gastric residence period of about two weeks. In some embodiments, less than about 5% of the therapeutic agent remaining in the system is degraded or oxidized after a gastric residence period of about three weeks. In some embodiments, less than about 5% of the therapeutic agent remaining in the system is degraded or oxidized after a gastric residence period of about four weeks. In some embodiments, less than about 5% of the therapeutic agent remaining in the system is degraded or oxidized after a gastric residence period of about a month.

Therapeutic Agents for Use in Gastric Residence Systems

Therapeutic agents which can be administered to or via the gastrointestinal tract can be used in the gastric residence systems of the invention. Therapeutic agents include, but are not limited to, drugs, pro-drugs, biologics, and any other substance which can be administered to produce a beneficial effect on an illness or injury. Therapeutic agents that can be used in the gastric residence systems of the invention include statins, such as rosuvastatin, nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; anti-dementia drugs, such as memantine; cardiac glycosides such as digoxin; alpha blockers such as tamsulosin; cholesterol absorption inhibitors such as ezetimibe; anti-gout treatments, such as colchicine; antihistamines, such as loratadine and cetirizine, opioids, such as loperamide; proton-pump inhibitors, such as omeprazole; antiviral agents, such as entecavir; antibiotics, such as doxycycline, ciprofloxacin, and azithromycin; anti-malarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as therapeutic agents in the gastric residence systems of the invention include proteins, polypeptides, polynucleotides, and hormones. Exemplary classes of therapeutic agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "therapeutic agent" includes salts, solvates, polymorphs, and co-crystals of the aforementioned substances. In certain embodiments, the therapeutic agent is selected from the group consisting of cetirizine, rosuvastatin, escitalopram, citalopram, risperidone, olanzapine, donezepil, and ivermectin. In some embodiments, the therapeutic agent is one that is used to treat a neuropsychiatric disorder, such as an anti-psychotic agent or an anti-dementia drug such as memantine.

Therapeutic Agent Classes of Interest

Gastric residence systems are well-suited for use in treatment of diseases and disorders which present difficulties with patient compliance, and thus in some embodiments, the gastric residence systems are used to treat a disease or disorder where patient compliance with a medication regimen is problematic. Such diseases and disorders include neuropsychiatric diseases and disorders, dementia and other diseases and disorders which affect memory, Alzheimer's disease, psychoses, schizophrenia, and paranoia. Accordingly, therapeutic agents which can be used in the gastric residence systems include, but are not limited to, anti-dementia agents, anti-Alzheimer's disease agents, and anti-psychotics.

Hydrophilic Therapeutic Agents

Exemplary hydrophilic therapeutic agents which can be used in the systems include risperidone, cetirizine, memantine, and olanzapine.

Hydrophobic Therapeutic Agents

Exemplary hydrophobic therapeutic agents which can be used in the systems include tacrolimus, ivermectin, rosuvastatin, citalopram, and escitalopram.

Low Dosage Agents

Drugs and other therapeutic agents which are administered at relatively low dosages, such as equal to or less than about 1 mg/day, about 0.5 mg/day, or about 0.1 mg/day, are also well-suited for use in the gastric residence systems of the invention. Examples of such agents which can be used in the gastric residence systems include, but are not limited to, levothyroxine, low dose contraceptives, and vitamins and other nutrients such as Vitamin A, Vitamin D, Vitamin K, folate, Vitamin B12, and biotin.

Residence Time

The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days, or up to about 7 days. In one embodiment, the gastric residence system has a residence time of about 10 days, or up to about 10 days. In one embodiment, the gastric residence system has a residence time of about 14 days, or up to about 14 days. In one embodiment, the gastric residence system has a residence time of about 3 weeks, or up to about 3 weeks. In one embodiment, the gastric residence system has a residence time of about 4 weeks, or up to about 4 weeks. In one embodiment, the gastric residence system has a residence time of about one month, or up to about one month.

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

In one embodiment, the gastric residence system has a residence time between about 24 hours and about three weeks. In one embodiment, the gastric residence system has a residence time between about 48 hours and about three weeks. In one embodiment, the gastric residence system has a residence time between about 72 hours and about three weeks. In one embodiment, the gastric residence system has a residence time between about 96 hours and about three weeks. In one embodiment, the gastric residence system has a residence time between about 5 days and about three weeks. In one embodiment, the gastric residence system has a residence time between about 6 days and about three weeks. In one embodiment, the gastric residence system has a residence time between about 7 days and about three weeks. In one embodiment, the gastric residence system has a residence time between about 10 days and about three weeks. In one embodiment, the gastric residence system has a residence time between about 14 days and about three weeks.

In one embodiment, the gastric residence system has a residence time between about 24 hours and about four weeks. In one embodiment, the gastric residence system has a residence time between about 48 hours and about four weeks. In one embodiment, the gastric residence system has a residence time between about 72 hours and about four weeks. In one embodiment, the gastric residence system has a residence time between about 96 hours and about four weeks. In one embodiment, the gastric residence system has a residence time between about 5 days and about four weeks. In one embodiment, the gastric residence system has a residence time between about 6 days and about four weeks. In one embodiment, the gastric residence system has a residence time between about 7 days and about four weeks. In one embodiment, the gastric residence system has a residence time between about 10 days and about four weeks. In one embodiment, the gastric residence system has a residence time between about 14 days and about four weeks. In one embodiment, the gastric residence system has a residence time between about three weeks and about four weeks.

In one embodiment, the gastric residence system has a residence time between about 24 hours and about one month. In one embodiment, the gastric residence system has a residence time between about 48 hours and about one month. In one embodiment, the gastric residence system has a residence time between about 72 hours and about one month. In one embodiment, the gastric residence system has a residence time between about 96 hours and about one month. In one embodiment, the gastric residence system has a residence time between about 5 days and about one month. In one embodiment, the gastric residence system has a residence time between about 6 days and about one month. In one embodiment, the gastric residence system has a residence time between about 7 days and about one month. In one embodiment, the gastric residence system has a residence time between about 10 days and about one month. In one embodiment, the gastric residence system has a residence time between about 14 days and about one month. In one embodiment, the gastric residence system has a residence time between about three weeks and about one month.

The gastric residence system releases a therapeutically effective amount of therapeutic agent during at least a portion of the residence time or residence period during which the system resides in the stomach. In one embodiment, the system releases a therapeutically effective amount of therapeutic agent during at least about 25% of the residence time. In one embodiment, the system releases a therapeutically effective amount of therapeutic agent during at least about 50% of the residence time. In one embodiment, the system releases a therapeutically effective amount of therapeutic agent during at least about 60% of the residence time. In one embodiment, the system releases a therapeutically effective amount of therapeutic agent during at least about 70% of the residence time. In one embodiment, the system releases a therapeutically effective amount of therapeutic agent during at least about 75% of the residence time. In one embodiment, the system releases a therapeutically effective amount of therapeutic agent during at least about 80% of the residence time. In one embodiment, the system releases a therapeutically effective amount of therapeutic agent during at least about 85% of the residence time. In one embodiment, the system releases a therapeutically effective amount of therapeutic agent during at least about 90% of the residence time. In one embodiment, the system releases a therapeutically effective amount of therapeutic agent during at least about 95% of the residence time. In one embodiment, the system releases a therapeutically effective amount of therapeutic agent during at least about 98% of the residence time. In one embodiment, the system releases a therapeutically effective amount of therapeutic agent during at least about 99% of the residence time.

Radiopacity

The systems are optionally radiopaque, so that they can be located via abdominal X-ray if necessary. In some embodiments, one or more of the materials used for construction of the system is sufficiently radiopaque for X-ray visualization. In other embodiments, a radiopaque substance is added to one or more materials of the system, or coated onto one or more materials of the system, or are added to a small portion of the system. Examples of suitable radiopaque substances are barium sulfate, bismuth subcarbonate, bismuth oxychloride, and bismuth trioxide. It is preferable that these materials should not be blended into the polymers used to construct the gastric residence system, so as not to alter therapeutic agent release from the carrier polymer, or desired properties of other system polymers. Metal striping or tips on a small portion of the system components can also be used, such as tungsten.

Manufacture/Assembly of System: Three-Dimensional Printing

Three-dimensional printing of components of the gastric residence system, such as arm or arm segments, is performed using commercially-available equipment. Three-dimensional printing has been used for pharmaceutical preparation; see Khaled et al., "Desktop 3D printing of controlled release pharmaceutical bilayer tablets," International Journal of Pharmaceutics 461:105-111 (2014); U.S. Pat. No. 7,276,252; Alhnan et al., "Emergence of 3D Printed Dosage Forms: Opportunities and Challenges," Pharm. Res., May 18, 2016, PubMed PMID: 27194002); Yu et al., "Three-dimensional printing in pharmaceutics: promises and problems," J. Pharm. Sci. 97(9):3666-3690 (2008); and Ursan et al., "Three-dimensional drug printing: A structured review," J. Am. Pharm. Assoc. 53(2):136-44 (2013).

The initial feedstocks for three-dimensional printing are polymers or polymer blends (e.g. enteric polymers, time-dependent polymers, or blends of one or more of an agent, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer or blended polymer material is extruded through a circular die, creating a cylindrical fiber which is wound around a spool.

Multiple spools are fed into the 3D printer (such as a Hyrel Printer, available from Hyrel 3D, Norcross, Georgia, United States), to be fed into their representative print heads. The print heads heat up and melt the material at the nozzle, and lay down a thin layer of material (polymer or polymer blend) in a specific position on the piece being manufactured. The material cools and hardens within seconds, and the next layer is added until the complete structure is formed. The quality of the dosage form is dependent on the feed rate, nozzle temperature, and printer resolution; feed rate and nozzle temperature can be adjusted to obtain the desired quality.

Three-dimensional printing can be used to manufacture individual elongate members, or segments of elongate members. Three-dimensional printing can also be used to prepare a bulk configuration, such as a consolidated "slab," similar to that prepared by co-extrusion methods described herein. The bulk configuration can be cut into individual pieces (that is, individual elongate members or individual segments) as needed.

In some embodiments of the invention, producing an entire elongate member, or "arm," of the gastric residence system by three-dimensional printing of the elongate member is contemplated. In some embodiments of the invention, producing a segment of an elongate member, or "arm," of the gastric residence system by three-dimensional printing of the segment of an elongate member is contemplated. In some embodiments, an elongate member or a segment thereof is produced by three-dimensional printing of adjacent portions of carrier polymer-agent blend and linker material in a bulk configuration, such as a slab configuration. The three-dimensional printing can be followed by cutting the bulk configuration into pieces which have the desired shape of the elongate member or segment thereof. The three-dimensional printing can be followed by compression molding of portions of the bulk configuration into pieces which have the desired shape of the elongate member or segment thereof.

Manufacture/Assembly of System: Co-Extrusion

Components of the gastric residence systems can be manufactured by co-extrusion. Most of the various configurations for the segments discussed herein, such as the "islands-in-the-sea" configurations, can be made by either three-dimensional printing or co-extrusion. However, co-extrusion is less expensive, and can be run as a continuous process, as opposed to three-dimensional printing, which is generally run as a batch process.

Co-extrusion of the "islands-in-the-sea" configuration is used in the textile industry and for production of fiber optics, but has rarely been applied in biomedical systems. See U.S. Pat. Nos. 3,531,368; 3,716,614; 4,812,012; and Haslauer et al., J. Biomed. Mater. Res. B Appl. Biomater. 103(5): 1050-8 (2015)).

Co-extrusion of components of the gastric residence system, such as an elongate member (arm), or a segment of an elongate member (arm), can be performed using commercially-available equipment, combined with customized co-extruder plumbing and customized dies for the desired configuration. The initial feedstocks for co-extrusion are polymers or polymer blends (e.g. enteric polymers, time-dependent polymers, or blends of one or more of an agent, a drug, an excipient, etc., with a carrier polymer, enteric polymers, or time-dependent polymers). The polymer or ingredients which are to be used for one region of the segment or elongate member to be manufactured are mixed and pelletized using hot melt extrusion. The polymer pellets thus formed are placed into hoppers above single screw extruders and dried to remove surface moisture. Pellets are gravimetrically fed into individual single-screw extruders, where they are melted and pressurized for co-extrusion.

The appropriate molten polymers are then pumped through custom designed dies with multiple channels where they form the required geometry. The composite polymer block is cooled (water-cooled, air-cooled, or both) and cut or stamped into the desired shape, including, but not limited to, such shapes as triangular prisms, rectangular prisms, or cylinder sections (pie-shaped wedges).

In some embodiments of the invention, producing an entire elongate member, or "arm," of the gastric residence system by co-extruding the elongate member is contemplated. In some embodiments of the invention, producing a segment of an elongate member, or "arm," of the gastric residence system by co-extruding the segment of an elongate member is contemplated. In some embodiments, an elongate member or a segment thereof is produced by co-extruding adjacent portions of carrier polymer-agent blend and linker material in a bulk configuration, such as a slab configuration. The co-extruding can be followed by cutting the bulk configuration into pieces which have the desired shape of the elongate member or segment thereof. The bulk or slab configuration of, for example, segment-linker-segment is cut at an angle perpendicular to the direction of co-extrusion. The co-extruding can be followed by compression molding of portions of the bulk configuration into pieces which have the desired shape of the elongate member or segment thereof.

Figure 12A:
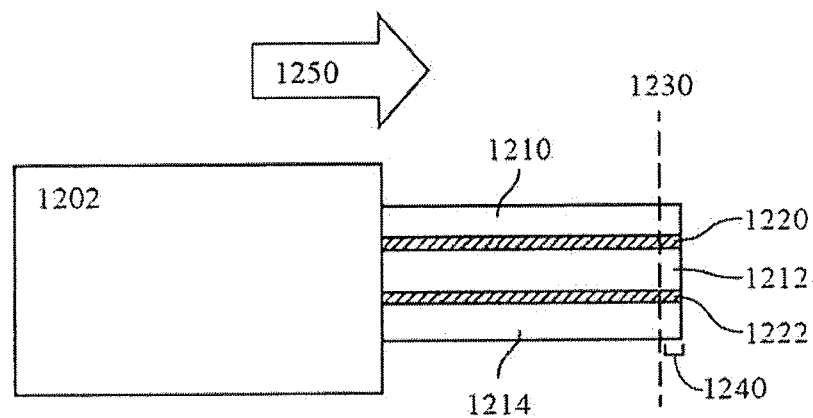
FIG. 12A shows a schematic drawing of a co-extrusion process of the invention.
Figure 12B:
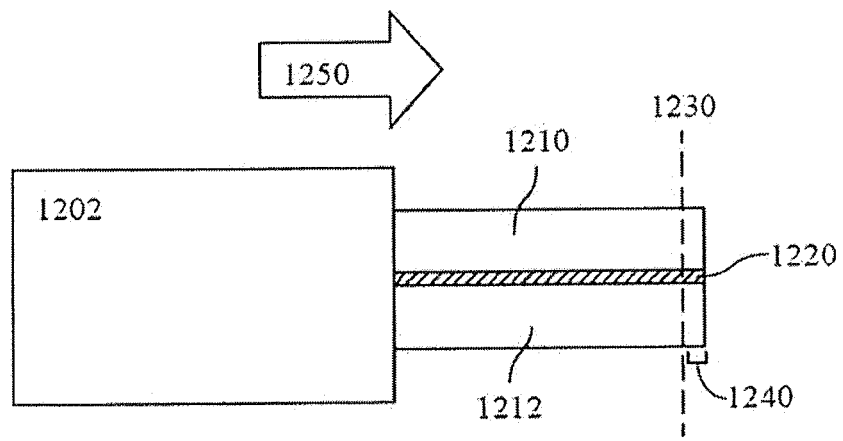
FIG. 12B shows a schematic drawing of another co-extrusion process of the invention.

FIG. 12A and FIG. 12B schematically illustrate such a co-extrusion process. FIG. 12A shows co-extrusion of an elongate member or "arm" which comprises three segments and two linkers. Extruder 1202 extrudes a single "ribbon" of material (extruded in the direction indicated by arrow 1250), which comprises three segment ribbon strip regions 1210, 1212, and 1214 which comprise carrier polymer-agent blend, that is, a blend of carrier polymer, therapeutic agent or salt thereof, and any desired excipients. The ribbon strip regions 1210, 1212, and 1214 comprising carrier polymer-agent blend are separated by ribbon strip regions 1220 and 1222 which comprise a linker blend, that is, a blend comprising linker polymer(s) or coupling polymer(s). The ribbon can be cut along dotted line 1230 to cut off a piece of ribbon 1240 to form the segment-linker-segment elongate member or "arm" 1260 shown in FIG. 12C. After the cut, the ribbon strip region 1210 of piece 1240 in FIG. 12A becomes the segment 1280 of the arm 1260 in FIG. 12C, the ribbon strip region 1212 becomes the segment 1282 of the arm 1260 in FIG. 12C, and the ribbon strip region 1214 becomes the segment 1284 of the arm 1260 in FIG. 12C, while the ribbon strip region 1220 in FIG. 12A becomes the linker 1290 of the arm 1260 in FIG. 12C and the ribbon strip region 1222 in FIG. 12A becomes the linker 1292 of the arm 1260 in FIG. 12C. The ribbon piece 1240 can be cut to form a square or rectangular section, or cut at an angle to form a triangular section, or cut and then stamped into the desired shape in a mold.

FIG. 12B illustrates co-extrusion of an arm with a single linker connecting two segments. Extruder 1202 extrudes a single "ribbon" of material (extruded in the direction indicated by arrow 1250), which comprises two segment ribbon strip regions 1210 and 1212 which comprise carrier polymer-agent blend, that is, a blend of carrier polymer, therapeutic agent or salt thereof, and any desired excipients. The two ribbon strip regions 1210 and 1212 comprising carrier polymer-agent blend are separated by a ribbon strip region 1220 which comprises a linker blend, that is, a blend comprising linker polymer(s) or coupling polymer(s). The ribbon can be cut along dotted line 1230 to cut off a piece of ribbon 1240 to form the segment-linker-segment elongate member or "arm" 1260 in FIG. 12D. After the cut, the ribbon strip region 1210 of piece 1240 in FIG. 12B becomes the segment 1280 of the arm 1260 in FIG. 12D, the ribbon strip region 1212 becomes the segment 1282 of the arm 1260 in FIG. 12D, and the ribbon strip region 1220 in FIG. 12B becomes the linker 1290 of the arm 1260 in FIG. 12D. The ribbon piece 1240 can be cut to form a square or rectangular section, or cut at an angle to form a triangular section, or cut and then stamped into the desired shape in a mold. Co-extrusion in this manner provides elongate members or "arms" with stronger bonding at the segment-linker junctions compared to heat-welding separate pieces of segments and linkers together, as shown in Example 2 and FIG. 13.

Elongate members or "arms" which comprise only a single segment and linker, that is, a segment-linker piece, can be prepared in the same manner. This would be equivalent to omitting segment ribbon 1212 from the extrusion illustrated in FIG. 12B, to produce an arm lacking segment 1282 in FIG. 12D. In a similar manner, elongate members or "arms" which comprise multiple linkers and segments, such as a segment-linker-segment-linker-segment configuration, can be prepared by co-extrusion of the appropriate regions. All of the segments can be identical in composition, or all of the segments can differ in composition, or some of the segments can be identical in composition while others of the segments can differ in composition. Similarly, all of the linkers can be identical in composition, or all of the linkers can differ in composition, or some of the linkers can be identical in composition while others of the linkers can differ in composition.

Elongate members or arms can be made with one, two, three, four, or five segments. When an elongate member is made with one segment, one linker can be attached to one end of the elongate member. When elongate members are made with multiple segments, a linker is located between and joins any two segments. Optionally, the elongate member can also have a linker at one end of the elongate member, that is, one end of the elongate member can be terminated or "capped" by a linker; this would be equivalent to omitting ribbon 1214 from FIG. 12A, to produce the arm in FIG. 12C lacking segment 1284.

The overall length of an elongate member is typically about 10 mm to about 20 mm, and the length of segments plus the length of the linkers in the elongate member (such as the elongate members shown in FIG. 12C and FIG. 12D), after cutting from the ribbon, should thus also range between about 10 mm and about 20 mm. Preferred ranges of elongate members are about 12 mm to about 20 mm, about 14 mm to about 20 mm, about 14 mm to about 18 mm, or about 14 mm to about 16 mm. Subject to the constraint that the length of all segments and linkers in an elongate member should fall within about 10 mm to about 20 mm, or the preferred subranges, the segments can range from between about 2 mm to about 20 mm in length, about 2 mm to about 18 mm in length, about 2 mm to about 16 mm in length, about 2 mm to about 14 mm in length, about 2 mm to about 12 mm in length, about 2 mm to about 10 mm in length, about 2 mm to about 8 mm in length, about 2 mm to about 6 mm in length, or about 2 mm to about 4 mm in length. Also subject to the constraint that the length of all segments and linkers in an elongate member should fall within about 10 mm to about 20 mm, or the preferred subranges, the linker regions in the elongate members can range from about 50 microns to about 2 mm in length, about 100 microns to about 2 mm in length, about 250 microns to about 2 mm in length, about 500 microns to about 2 mm in length, about 750 microns to about 2 mm in length, about 1 mm to about 2 mm in length, about 1.25 mm to about 2 mm in length, about 1.5 mm to about 2 mm in length; or about 1.75 mm to about 2 mm in length. In some embodiments, the linker regions can range from about 50 microns to about 1.75 mm in length, about 50 microns to about 1.5 mm in length, about 50 microns to about 1.25 mm in length, about 50 microns to about 1 mm in length, about 50 microns to about 750 microns in length, about 50 microns to about 500 microns in length, about 50 microns to about 250 microns in length, or about 50 microns to about 100 microns in length.

In some embodiments, an elongate member or a segment thereof is produced by co-extruding adjacent portions of carrier polymer-agent blend and linker material in a bulk configuration, such as a slab configuration, while also co-extruding an additional polymer or polymers within the carrier polymer-agent blend, the linker material, or both the carrier polymer-agent blend and the linker material. The co-extruding the additional polymer or polymers within the carrier polymer-agent blend, the linker material, or both the carrier polymer-agent blend and the linker material can be performed in an islands-in-the-sea configuration. The co-extruding can be followed by cutting the bulk configuration into pieces which have the desired shape of the elongate member or segment thereof. The co-extruding can be followed by compression molding of portions of the bulk configuration into pieces which have the desired shape of the elongate member or segment thereof.

Co-extrusion of elongate members by the methods described herein provides valuable advantages over other methods of preparing the elongate members. When segments are prepared in "linear" fashion, that is, by single-component extrusion of carrier polymer-agent blend through a die having the shape of the segment or elongate member cross-section, such that the elongate member or segment exits the extruder along its longitudinal axis, the segment must be cut to the proper length, and then additional post-extrusion steps are required to affix linkers and additional segments. In contrast, by using the co-extrusion methods described herein, the entire elongate member can be produced as one co-extruded unit in a ribbon, and cutting the ribbon into pieces at appropriate points (optionally followed by stamping the cut piece into another shape) immediately produces an elongate member without the need for further post-extrusion assembly steps. This elimination of extra steps reduces the cost of producing the elongate members. It also enables production of elongate members at a more rapid rate than linear extrusion. As noted in Example 2, the co-extrusion process enables high throughput scalable production of composite arms. Co-extrusion of a composite ribbon at about 12 inches per minute yields approximately 180 3.33-mm width elongate members or "arms" per minute, while linear (single-component) extrusion of elongate members or "arms" in an axial direction at the same linear rate yields less than six arms per minute, and also requires post-extrusion steps to assemble the segments into elongate members by incorporating linkers (such as disintegrating matrices) between the segments. In addition, as shown in Example 2, elongate members produced by co-extrusion have stronger linker-segment junctions than elongate members produced by linear extrusion and heat welding of linkers and segments.

Accordingly, in one embodiment, the co-extrusion methods of the invention provide a method of co-extruding an elongate member as an assembly of segments and linkers at a rate sufficient to prepare up to about or at least about 30 elongate members per minute, or up to about or at least about 50, up to about or at least about 100, up to about or at least about 150, up to about or at least about 180, up to about or at least about 200, up to about or at least about 300, up to about or at least about 400, or up to about or at least about 500 elongate members per minute, such as between about 30 and about 500 elongate members per minute, or between about 50 and about 500, about 100 and about 500, about 150 and about 500, about 180 and about 500, about 200 and about 500, about 300 and about 500, or about 400 and about 500 elongate members per minute; or about 50 to about 400, about 50 to about 300, about 50 to about 200, or about 50 to about 180 elongate members per minute. In any of the foregoing embodiments, the arms are about 1 to 5 mm in width, such as between about 2 and 4 mm in width. In any of the foregoing embodiments, the arms are produced from a single co-extrusion device.

In one embodiment, the co-extrusion methods of the invention is performed at a rate sufficient for the co-extruding to produce elongate members at a rate about or at least about 5 times faster, about 10 times faster, about 20 times faster, about 30 times faster, or about 50 times faster than single-component extrusion at the same linear extrusion rate, or between about 5 to about 10, about 5 to about 20, about 5 to about 30, or about 5 to about 50 times faster than single-component extrusion at the same linear extrusion rate.

As the ribbon is extruded, the ribbon will cool from the temperature required for extrusion to room temperature, or additional cooling can be applied to increase the cooling rate or cool the ribbon below room temperature. Once the ribbon has reached a temperature where it can be cut, the ribbon is cut to produce the elongate members. If the elongate members will be stamped into the desired shape after cutting, the ribbon may be cut while it is still somewhat malleable, that is, before it cools entirely. Alternatively, the ribbon may be produced in a substantial length (for example, 12 inches or 30 cm), and stored until later, when it can be cut into the desired elongate members and assembled into the gastric residence systems.

Figure 11A:
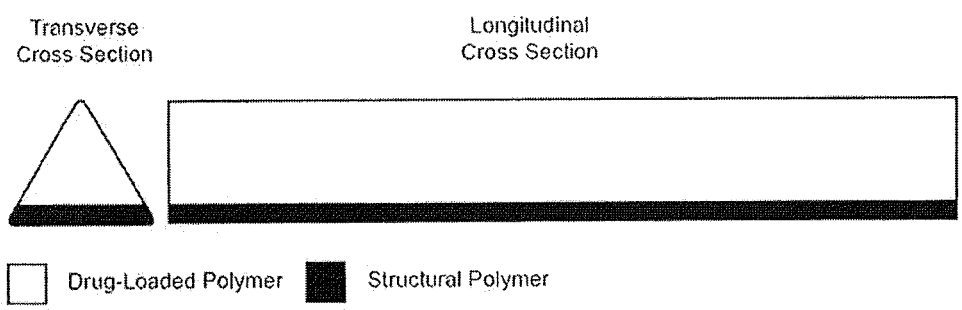
FIG. 11A shows a schematic drawing of an exemplary architecture (spine) for externally reinforced drug arms.

In addition to manufacturing elongate members comprising carrier polymer-agent segments and linkers, co-extrusion can be used to manufacture elongate members having reinforcing material. For example, the reinforced elongate member depicted in FIG. 11A can be manufactured by co-extrusion of the drug-loaded polymer (carrier polymer-agent component) and structural polymer (reinforcing material). The transverse cross-section at left of FIG. 11A represents the die pattern that can be used to manufacture a reinforced, co-extruded segment with reinforcing on one side of a triangular elongate member. Other patterns of co-extrusion that can be used include co-extrusion to produce elongate members with any cross-sectional shape with reinforcing material on the surface, such as a triangular elongate member with reinforcing material on two sides of the triangular elongate member.

Gastric Delivery Pharmacokinetics for Gastric Residence Systems

The gastric residence systems of the invention provide for high bioavailability of the therapeutic agent as measured by $AUC_{inf}$ after administration of the systems, relative to the bioavailability of a conventional oral formulation of the therapeutic agent. The systems also provide for maintenance of a substantially constant plasma level of the therapeutic agent.

Relative bioavailability, $F_{REL}$, of two different formulations, formulation A and formulation B, is defined as:

$$F_{REL} = 100 \times (AUC_A \times Dose_B)/(AUC_B \times Dose_A)$$

where $AUC_A$ is the area under the curve for formulation A, $AUC_B$ is the area under the curve for formulation B, $Dose_A$ is the dosage of formulation A used, and $Dose_B$ is the dosage of formulation B used. AUC, the area under the curve for the plot of therapeutic agent plasma concentration versus time, is usually measured at the same time (t) after administration of each formulation, in order to provide the relative bioavailability of the formulations at the same time point. $AUC_{inf}$ refers to the AUC measured or calculated over "infinite" time, that is, over a period of time starting with initial administration, and ending where the plasma level of the therapeutic agent has dropped to a negligible amount.

In one embodiment, the substantially constant plasma level of therapeutic agent provided by the gastric residence systems of the invention can range from at or above the trough level of the plasma level of therapeutic agent when administered daily in a conventional oral formulation (that is, $C_{min}$ of therapeutic agent administered daily in immediate-release formulation) to at or below the peak plasma level of therapeutic agent when administered daily in a conventional oral formulation (that is, $C_{max}$ of therapeutic agent administered daily in immediate-release formulation). In some embodiments, the substantially constant plasma level of therapeutic agent provided by the gastric residence systems of the invention can be about 50% to about 90% of the peak plasma level of therapeutic agent when administered daily in a conventional oral formulation (that is, $C_{max}$ of therapeutic agent administered daily in immediate-release formulation). The substantially constant plasma level of therapeutic agent provided by the gastric residence systems of the invention can be about 75% to about 125% of the average plasma level of therapeutic agent when administered daily in a conventional oral formulation (that is, $C_{ave}$ of therapeutic agent administered daily in immediate-release formulation). The substantially constant plasma level of therapeutic agent provided by the gastric residence systems of the invention can be at or above the trough level of plasma level of therapeutic agent when administered daily in a conventional oral formulation (that is, $C_{min}$ of therapeutic agent administered daily in immediate-release formulation), such as about 100% to about 150% of $C_{min}$.

The gastric residence systems of the invention can provide bioavailability of therapeutic agent released from the system of at least about 50%, at least about 60%, at least about 70%, or at least about 80% of that provided by an immediate release form comprising the same amount of therapeutic agent. As indicated above, the bioavailability is measured by the area under the plasma concentration-time curve (AUCinf).

Methods of Treatment Using the Gastric Residence Systems

The gastric residence systems can be used to treat conditions requiring administration of a therapeutic agent over an extended period of time. For long-term administration of therapeutic agents which are taken for months, years, or indefinitely, administration of a gastric residence system once weekly, once every two weeks, or once a month can provide substantial advantages in patient compliance and convenience.

Once a gastric residence system has been administered to a patient, the system provides sustained release of therapeutic agent over the period of gastric retention. After the period of gastric retention, the system degrades and passes out of the stomach. Thus, for a system with a gastric retention period of one week, the patient will swallow (or have administered to the stomach via other methods) a new system every week. Accordingly, in one embodiment, a method of treatment of a patient with a gastric retention system of the invention having a gastric residence period of a number of days D (where D-days is the gastric residence period in days), over a total desired treatment period T-total (where T-total is the desired length of treatment in days) with the therapeutic agent in the system, comprises introducing a new gastric residence system every D-days into the stomach of the patient, by oral administration or other methods, over the total desired treatment period. The number of gastric residence systems administered to the patient will be (T-total) divided by (D-days). For example, if treatment of a patient for a year (T-total=365 days) is desired, and the gastric residence period of the system is 7 days (D-days=7 days), approximately 52 gastric residence systems will be administered to the patient over the 365 days, as a new system will be administered once every seven days.

Kits and Articles of Manufacture

Also provided herein are kits for treatment of patients with the gastric residence systems of the invention. The kit may contain, for example, a sufficient number of gastric residence systems for periodic administration to a patient over a desired total treatment time period. If the total treatment time in days is (T-total), and the gastric residence systems have a residence time of (D-days), then the kit will contain a number of gastric residence systems equal to ((T-total) divided by (D-days)) (rounded to an integral number), for administration every D-days. The kit may contain, for example, several gastric residence systems in containers (where the containers may be capsules) and may optionally also contain printed or computer readable instructions for dosing regimens, duration of treatment, or other information pertinent to the use of the gastric residence systems and/or the therapeutic agent contained in the gastric residence systems. For example, if the total treatment period prescribed for the patient is one year, and the gastric residence system has a residence time of one week, the kit may contain 52 capsules, each capsule containing one gastric residence system, with instructions to swallow one capsule once a week on the same day (e.g., every Saturday).

Articles of manufacture, comprising a sufficient number of gastric residence systems for periodic administration to a patient over a desired total treatment time period, and optionally comprising instructions for dosing regimens, duration of treatment, or other information pertinent to the use of the gastric residence systems and/or the therapeutic agent contained in the gastric residence systems, are also included in the invention. The articles of manufacture may be supplied in appropriate packaging, such as dispensers, trays, or other packaging that assists the patient in administration of the gastric residence systems at the prescribed interval.

EXEMPLARY EMBODIMENTS

The invention is further described by the following embodiments. The features of each of the embodiments are combinable with any of the other embodiments where appropriate and practical.

Embodiment 1. A gastric residence system for administration to the stomach of a patient, comprising:
an elastomer component, and a plurality of at least three carrier polymer-agent components comprising a carrier polymer and a therapeutic agent or a salt thereof, attached to the elastomer component,
wherein each of the plurality of carrier polymer-agent components is an elongate member comprising a proximal end, a distal end, and an outer surface therebetween;
wherein the proximal end of each elongate member is attached to the elastomer component and projects radially from the elastomer component, each elongate member having its distal end not attached to the elastomer component and located at a larger radial distance from the elastomer component than the proximal end;
wherein each elongate member is comprised of at least two segments, each segment comprising a proximal end, a distal end, and an outer surface therebetween;
wherein the segments are attached together via linker regions having an outer surface;
wherein at least one of the linker regions comprises a first linker material and a second linker material, where:
i) the second linker material extends from the outer surface of the at least one linker region into the bulk of the at least one linker region; or
ii) the second linker material extends from the outer surface of the at least one linker region through the bulk of the at least one linker region and re-emerges on the outer surface; or
iii) portions of the second linker material extend from the outer surface of the at least one linker region into the bulk of the at least one linker region, and portions of the second linker material extend from the outer surface of the at least one linker region through the bulk of the at least one linker region and re-emerge on the outer surface.

Embodiment 2. A gastric residence system for administration to the stomach of a patient, comprising:
an elastomer component, and a plurality of at least three carrier polymer-agent components comprising a carrier polymer and a therapeutic agent or a salt thereof, attached to the elastomer component,
wherein each of the plurality of carrier polymer-agent components is an elongate member comprising a proximal end, a distal end, and an outer surface therebetween;
wherein the proximal end of each elongate member is attached to the elastomer component and projects radially from the elastomer component, each elongate member having its distal end not attached to the elastomer component and located at a larger radial distance from the elastomer component than the proximal end;
wherein each elongate member is comprised of at least two segments, each segment comprising a proximal end, a distal end, and an outer surface therebetween;
wherein the segments are attached together via a linker region; and wherein at least one segment further comprises a segment island material, where:
i) the segment island material extends from the outer surface of the at least one carrier polymer-agent segment into the bulk of the at least one carrier polymer-agent segment; or
ii) the segment island material extends from the outer surface of the at least one carrier polymer-agent segment through the bulk of the at least one carrier polymer-agent segment and re-emerges on the outer surface; or
iii) portions of the segment island material extend from the outer surface of the at least one carrier polymer-agent segment into the bulk of the at least one carrier polymer-agent segment, and portions of the segment island material extend from the outer surface of the at least one carrier polymer-agent segment through the bulk of the at least one carrier polymer-agent segment and re-emerges on the outer surface.

Embodiment 3. A gastric residence system for administration to the stomach of a patient, comprising:
an elastomer component, and a plurality of at least three carrier polymer-agent components comprising a carrier polymer and a therapeutic agent or a salt thereof, attached to the elastomer component,
wherein each of the plurality of carrier polymer-agent components is an elongate member comprising a proximal end, a distal end, and an outer surface therebetween;
wherein the proximal end of each elongate member is attached to the elastomer component and projects radially from the elastomer component, each elongate member having its distal end not attached to the elastomer component and located at a larger radial distance from the elastomer component than the proximal end;
wherein each elongate member is comprised of at least two segments, each segment comprising a proximal end, a distal end, and an outer surface therebetween;
wherein at least one segment further comprises a reinforcing material, where the reinforcing material extends axially along the interior of the at least one segment; and
wherein the segments are attached together via a linker region.

Embodiment 4. The gastric residence system of embodiment 3, wherein the reinforcing material extends axially along the interior of the at least one segment for at least about 90% of the length of the segment.

Embodiment 5. The gastric residence system of embodiment 3 or embodiment 4, wherein the reinforcing material has an I-beam configuration or an H-beam configuration.

Embodiment 6. The gastric residence system of embodiment 3 or embodiment 4, wherein the reinforcing material has a truss configuration.

Embodiment 7. A gastric residence system for administration to the stomach of a patient, comprising:
an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween;

wherein the proximal end of each elongate member is attached to the elastomer component and projects radially from the elastomer component, each elongate member having its distal end not attached to the elastomer component and located at a larger radial distance from the elastomer component than the proximal end;

wherein each elongate member is comprised of at least two segments, each segment comprising a proximal end, a distal end, and an outer surface therebetween;

wherein one or more of the elongate members further comprise a fenestrated coating on the outer surface; and wherein the segments are attached together via a linker region.

Embodiment 8. A gastric residence system for administration to the stomach of a patient, comprising:

an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween;

wherein the proximal end of each elongate member is attached to the elastomer component and projects radially from the elastomer component, each elongate member having its distal end not attached to the elastomer component and located at a larger radial distance from the elastomer component than the proximal end;

wherein each elongate member is comprised of at least two segments, each segment comprising a proximal end, a distal end, and an outer surface therebetween;

wherein the segments are attached together via a linker region having an outer surface; wherein the segments of the elongate members have a lamellar configuration comprising at least two layers.

Embodiment 9. A gastric residence system for administration to the stomach of a patient, comprising:

an elastomer component, and a plurality of at least three carrier polymer-agent components comprising a carrier polymer and a therapeutic agent or a salt thereof, attached to the elastomer component, wherein each of the plurality of carrier polymer-agent components is an elongate member comprising a proximal end, a distal end, and an outer surface therebetween;

wherein the proximal end of each elongate member is attached to the elastomer component and projects radially from the elastomer component, each elongate member having its distal end not attached to the elastomer component and located at a larger radial distance from the elastomer component than the proximal end;

wherein each elongate member is comprised of at least two segments, each segment comprising a proximal end, a distal end, and an outer surface therebetween;

wherein the segments are attached together via linker regions having an outer surface;

wherein a portion of the linker regions extends into the segments, or wherein a portion of the segments extends into the linker regions, or both a portion of the linker regions extends into the segments and a portion of the segments extends into the linker regions.

Embodiment 10. A method of manufacturing an elongate member for use in a gastric residence system, comprising:
co-extruding the elongate member.

Embodiment 11. The method of embodiment 10, wherein co-extruding the elongate member comprises:
co-extruding at least two regions comprising a carrier polymer-agent blend, wherein each region of carrier polymer-agent blend is separated from an adjacent region of carrier polymer-agent blend by a linker region.

Embodiment 12. The method of embodiment 11, wherein the carrier polymer of the carrier polymer-agent blend is selected from the group consisting of polycaprolactone and polydioxanone.

Embodiment 13. The method of embodiment 11 or embodiment 12, wherein the agent of the carrier polymer-agent blend is selected from the group consisting of analgesics; anti-analgesics; anti-inflammatory drugs; antipyretics; antidepressants; antiepileptics; antipsychotic agents; neuroprotective agents; anti-proliferatives; anti-cancer agents; antihistamines; antimigraine drugs; hormones; prostaglandins; antimicrobials; antibiotics; antifungals; antivirals; antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; antimalarial drug; quinine; lumefantrine; chloroquine; amodiaquine; pyrimethamine; proguanil; chlorproguanil-dapsone; sulfonamides; sulfadoxine; sulfamethoxypyridazine; mefloquine; atovaquone; primaquine; halofantrine; doxycycline; clindamycin; artemisinin; artemisinin derivatives; artemether; dihydroartemisinin; arteether; and artesunate.

Embodiment 14. The method of any one of embodiments 11 to 13, wherein the linker region comprises a material selected from the group consisting of an enteric linker and a time-dependent linker.

Embodiment 15. The method of any one of embodiments 11 to 14, wherein at least one junction between a carrier polymer-agent region and a linker region is co-extruded in an interlocking configuration.

Embodiment 16. The method of any one of embodiments 11 to 15, wherein at least one carrier polymer-agent region is co-extruded in an islands-in-the-sea configuration.

Embodiment 17. The method of any one of embodiments 11 to 16, wherein at least one linker region is co-extruded in an islands-in-the-sea configuration.

Embodiment 18. The method of embodiment 16 or embodiment 17, wherein the island components of the islands-in-the-sea configuration comprise at least one material selected from the group consisting of an enteric polymer and a time-dependent polymer.

Embodiment 19. A method of manufacturing an elongate member for use in a gastric residence system, comprising:
printing the elongate member by three-dimensional printing.

Embodiment 20. The method of embodiment 19, wherein printing the elongate member by three-dimensional printing comprises:
printing at least two regions comprising a carrier polymer-agent blend, wherein each region of carrier polymer-agent blend is separated from an adjacent region of carrier polymer-agent blend by a linker region.

Embodiment 21. The method of embodiment 20, wherein the carrier polymer of the carrier polymer-agent blend is selected from the group consisting of polycaprolactone and polydioxanone.

Embodiment 22. The method of embodiment 20 or 21, wherein the agent of the carrier polymer-agent blend is selected from the group consisting of analgesics; anti-analgesics; anti-inflammatory drugs; antipyretics; antidepressants; antiepileptics; antipsychotic agents; neuroprotective agents; anti-proliferatives; anti-cancer agents; antihistamines; antimigraine drugs; hormones; prostaglandins; antimicrobials; antibiotics; antifungals; antivirals; antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics: anti-coagulants; enzyme inhibitors; steroidal agents; steroidal or non-steroidal anti-inflammatory agents; corticosteroids; dopaminergics; electrolytes; gastrointestinal drugs; muscle relaxants; nutritional agents; vitamins; parasympathomimetics; stimulants; anorectics; anti-narcoleptics; antimalarial drug; quinine; lumefantrine; chloroquine; amodiaquine; pyrimethamine; proguanil; chlorproguanil-dapsone; sulfonamides; sulfadoxine; sulfamethoxypyridazine; mefloquine; atovaquone; primaquine; halofantrine; doxycycline; clindamycin; artemisinin; artemisinin derivatives; artemether; dihydroartemisinin; arteether; and artesunate.

Embodiment 23. The method of any one of embodiments 20-22, wherein the linker region comprises a material selected from the group consisting of an enteric linker and a time-dependent linker.

Embodiment 24. The method of any one of embodiments 20-23, wherein at least one junction between a carrier polymer-agent region and a linker region is printed in an interlocking configuration.

Embodiment 25. The method of any one of embodiments 20-24, wherein at least one carrier polymer-agent region is printed in an islands-in-the-sea configuration.

Embodiment 26. The method of any one of embodiments 20-25, wherein at least one linker region is printed in an islands-in-the-sea configuration.

Embodiment 27. The method of embodiment 25 or 26, wherein the island components of the islands-in-the-sea configuration comprise at least one material selected from the group consisting of an enteric polymer and a time-dependent polymer.

Embodiment 28. The method of any one of embodiments 20-27, wherein the linkers uncouple after about seven days in fasted-state simulated gastric fluid.

Embodiment 29. A method of manufacturing an elongate member for use in a gastric residence system, comprising:
manufacturing the elongate member by additive manufacturing.

Embodiment 30. The method of embodiment 29, wherein manufacturing the elongate member by additive manufacturing comprises:
manufacturing at least two regions comprising a carrier polymer-agent blend, wherein each region of carrier polymer-agent blend is separated from an adjacent region of carrier polymer-agent blend by a linker region.

Embodiment 31. The method of embodiment 30, wherein the carrier polymer of the carrier polymer-agent blend is selected from the group consisting of polycaprolactone and polydioxanone.

Embodiment 32 The method of embodiment 30 or 31, wherein the agent of the carrier polymer-agent blend is selected from the group consisting of analgesics; anti-analgesics; anti-inflammatory drugs; antipyretics; antidepressants; antiepileptics; antipsychotic agents; neuroprotective agents; anti-proliferatives; anti-cancer agents; antihistamines; antimigraine drugs; hormones; prostaglandins; antimicrobials; antibiotics; antifungals; antivirals; antiparasitics: anti-muscarinics; anxiolytics; bacteriostatics; immunosuppressant agents; sedatives; hypnotics; antipsychotics; bronchodilators; anti-asthma drugs; cardiovascular drugs; anesthetics: anti-coagulants; enzyme inhibitors; steroidal agents; steroidal or non-steroidal anti-inflammatory agents; corticosteroids; dopaminergics; electrolytes; gastrointestinal drugs; muscle relaxants; nutritional agents; vitamins; parasympathomimetics; stimulants; anorectics; anti-narcoleptics; antimalarial drug; quinine; lumefantrine; chloroquine; amodiaquine; pyrimethamine; proguanil; chlorproguanil-dapsone; sulfonamides; sulfadoxine; sulfamethoxypyridazine; mefloquine; atovaquone; primaquine; halofantrine; doxycycline; clindamycin; artemisinin; artemisinin derivatives; artemether; dihydroartemisinin; arteether; and artesunate.

Embodiment 33. The method of any one of embodiments 30-32, wherein the linker region comprises a material selected from the group consisting of an enteric linker and a time-dependent linker.

Embodiment 34. The method of any one of embodiments 30-33, wherein at least one junction between a carrier polymer-agent region and a linker region is manufactured in an interlocking configuration.

Embodiment 35. The method of any one of embodiments 30-34, wherein at least one carrier polymer-agent region is manufactured in an islands-in-the-sea configuration.

Embodiment 36. The method of any one of embodiments 30-35, wherein at least one linker region is manufactured in an islands-in-the-sea configuration.

Embodiment 37. The method of embodiment 35 or 36, wherein the island components of the islands-in-the-sea configuration comprise at least one material selected from the group consisting of an enteric polymer and a time-dependent polymer.

Embodiment 38. The method of any one of embodiments 30-37, wherein the linkers uncouple after about seven days in fasted-state simulated gastric fluid.

EXAMPLES

The invention is further illustrated by the following non-limiting examples.

Example 1: Reinforcing Drug Arms with Structural Polymer

Dosage forms with high drug loading are structurally brittle and further weaken upon hydration in the gastric environment. Thus, it is difficult to successfully achieve gastric retention for 7 days for high drug loaded formulations. Two-layered architectures with external reinforcement layer surrounding a high-drug loaded formulation were prepared to understand the effect on maintaining the mechanical strength of dosage forms and compare their performance under an external mechanical stress.

Figure 11B:
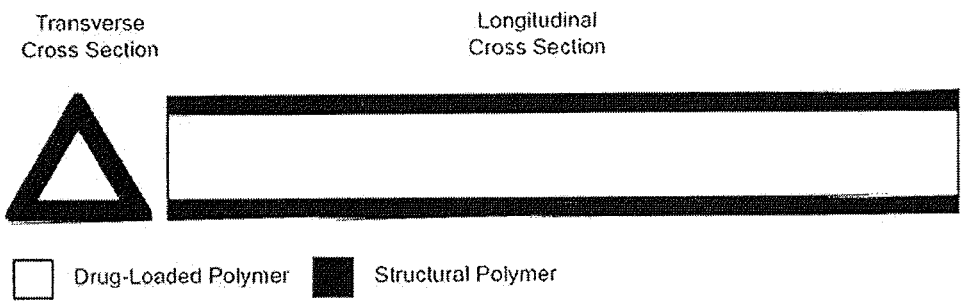
FIG. 11B shows a schematic drawing of an exemplary architecture (exoskeleton) for externally reinforced drug arms.

To create the reinforcement layer, PCL doped with black iron oxide pigment was extruded as a ribbon approximately 500 micrometers thick and cut into small pieces of 20 mm length. The thin 100% black PCL layer was placed compression molded on one-side of a 38% drug loaded arm by keeping the two layers in close contact with each other and incubating in an oven for 10 minutes at 75° C. and then compressing together. This process was used to create a spine reinforcement architecture wherein the carrier polymer-agent blend has a spine-type reinforcement layer on one side; a schematic drawing of this architecture is shown in FIG. 11A. This process was also used to create an exoskeleton reinforcement architecture wherein the carrier polymer-agent blend has an exoskeleton-type reinforcement layer on all three sides; a schematic drawing of this architecture is shown in FIG. 11B, and a photograph of the exoskeleton-reinforced arm is shown in FIG. 11C. The mechanical strength of the reinforced high drug loaded sample was compared with non-reinforced high drug loaded sample for both reinforcement architectures (spine and exoskeleton) using 4-pt bending test pre- and post-incubation in FaSSGF for 24 hr.

The results indicate that in the pre-incubated condition, reinforced architectures make the high drug loaded arms more ductile as they can withstand higher bending force for both reinforcement architectures, as shown in the tables in FIG. 1D. Upon incubation, the reinforcement layer helps strengthen and maintains the stiffness of the high drug loaded formulation which is critical for long gastric residence period.

As noted in the section "Manufacture/assembly of system: co-extrusion," this reinforced elongate member can also be produced by co-extrusion of the reinforcing material and the carrier polymer-agent blend, instead of producing the reinforcing material and the carrier-polymer agent components separately and compressing them together.

Figure 12C:
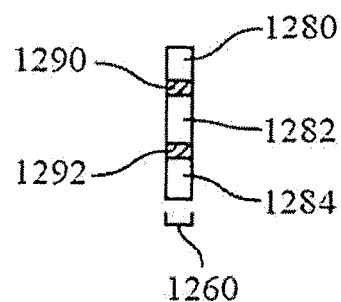
FIG. 12C shows an elongate member prepared by the co-extrusion process of the invention illustrated in FIG. 12A.
Figure 12D:
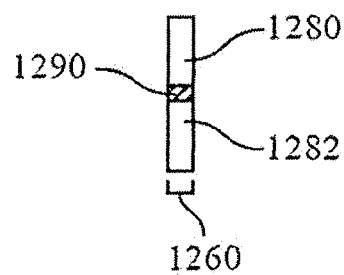
FIG. 12D shows an elongate member prepared by the co-extrusion process of the invention illustrated in FIG. 12B.

Example 2: Co-Extrusion Compared to Single Component Extrusion with Thermal Bonding-Effect on Weld Strength Composite arms consisting of two 1.5-mm segments disintegrating matrix (DM) (equivalent to elements 1290 and 1292 of FIG. 12C) flanked by three 4-mm to 6.5-mm segments of PCL (equivalent to elements 1280, 1282 and 1284 of FIG. 12C) were prepared in a two-step process in which a ribbon was produced by co-extrusion and then cut perpendicular to the flow (extrusion) direction, as shown in FIG. 12A, to yield arms with rectangular cross section. The ribbon was produced using a standard lab-scale two-component co-extrusion machine which consists of two ⅝" single screw extruders connected with a co-extrusion head that allows flowing polymer from both extruders to be arranged together in specific orientations. An example of the elongate members (arms) produced by co-extrusion and cutting is depicted in FIG. 12C.

Pure 80 k PCL was loaded into one extruder and a disintegrating matrix (DM) blend (60% 80 k PCL/40% HPMCAS-MG) was loaded into the other. The melt flowrate set-points were adjusted so that the DM flowrate was set to approximately 20% of the PCL flow rate. The molten ribbon exiting the co-extrusion head was guided onto a conveyor with a Teflon belt to both provide support to the ribbon and to allow it to harden before handling. The ribbon had cross sectional dimensions of 3.5 mm×20.5 mm. The ribbon was cut perpendicular to the direction of extrusion to produce composite arms of 20.5 mm in length, 4 mm in width and 3.5 mm in height.

For comparison, arms were produced using heat welding to join previously extruded segments of PCL and the same DM blend. Extruded 80 k PCL arms were cut into 1 cm pieces. One end of a 1 cm PCL segment was melted by contacting with a 100° C. heating element for 5 seconds and one end of a segment of DM was melted by contacting with a 170° C. heating element for 10 seconds. The two molten ends were pressed together gently for about two seconds and the resulting bead was flattened along the weld. Using clippers, the joined DM segment was cut to a length of 2 mm. The unwelded end of the DM segment was joined to a second 1 cm PCL segment by repeating the heat-welding process.

Weld strength of the co-extruded arms and heat welded arms was compared by observing the location where samples comprising a single linker region flanked by two PCL segments tore under tensile stress. Co-extruded as well as heat welded arms were incubated in FaSSGF for three different time periods, 1 day, 4 days and 7 days. For all three incubation periods, the arms were removed from FaSSGF solution at the respective time point, rinsed with DI water and dry wiped. Weld strength of five post-incubated arms was tested per condition by performing tensile test on linear stage tensile tester. The average stage velocity of the tensile tested was set at 0.0796 mm/s and the maximum stage displacement varied between samples according to yield location.

The data in FIG. 13 show that for all incubation periods, 80% or more of the heat welded arms tore at the weld and not within the linker, whereas none of the co-extruded arms tore at the weld and 80% or more tore within the linker. Tearing within the linker indicates that the co-extruded arms have a strong interface between the linker and the drug formulation, which was not observed in the heat welded arms which failed at the welded interface.

Example 3: Production Rate Co-Extrusion Compared to Single Component Extrusion with Thermal Bonding The co-extrusion process performed as described in Example 2 enables high throughput scalable production of composite arms. Co-extrusion of a composite ribbon at about 12 inches per minute yields approximately 180 3.33-mm width arms per minute. Extrusion of arms in an axial direction at the same linear rate yields less than six arms per minute and requires additional processing to incorporate disintegrating matrix segments.

Example 4: 2-Layer Structure with Internal Reinforcement and API Loaded Outer Layer to Achieve Complete Release of Hydrophobic API Formulating a hydrophobic drug in the bulk matrix limits the hydration of the matrix core and achieves only ~50% total release at day 7. A 2-layer structure with a hydrophobic active pharmaceutical ingredient (API) in the outer layer surrounding a structural PCL core was prepared. Empty PCL arms were dipped in a solution containing tacrolimus and polyethylene vinyl acetate (PEVA) (30% w/v in dichloromethane). Tacrolimus:PEVA ratios of 1:1, 1:2 and 2:1 were evaluated. Dip coating resulted in weight gains of approximately 10-20% and deposition of approximately 6 mg tacrolimus on the surface of the PCL structural element.

To test in vitro release under simulated physiological conditions, fasted state simulated gastric fluid (FaSSGF) was prepared per the manufacturer's instructions (www.biorelevant.com; see also WO 2017/070612, particularly Examples 3 and 7). Individual coated drug arms were incubated in 10 mL release media in a shaking incubator at 37° C. for 7 days. Drug content in the release media was typically analyzed after 6 hours, 24 hours, and then daily for up to 7 days by HPLC. At each time point, the entire volume of release media was replaced with fresh media. Nearly 100% of the tacrolimus was released after 7 days incubation in vitro from the formulations that contained tacrolimus: PEVA ratios of 1:1 and 2:1. Tacrolimus release profiles over time are presented for the various formulations in FIG. 14.

Example 5: Islands-in-the-Sea Co-Extrusion

Co-extrusion was used to produce a model rectangular ribbon capable of serving as a precursor for segment-linker-segment composite arms, each arm comprising a linker region consisting of an array of cylindrical "islands in the sea" flanked by segments of carrier polymer-agent blend. The islands in the sea extended from one outer surface to the opposite surface. Polypropylene was used as a model island material and PCL was used to model the sea material of the linker. PCL was also used to model the carrier polymer-agent blend. The ribbon was produced using a standard lab-scale two-component co-extrusion machine which consists of two ⅝" single screw extruders connected with a co-extrusion head that allows flowing polymer from both extruders to be arranged together in specific orientations. The co-extrusion head was designed to produce a ribbon with cross sectional dimensions of about 3.5×20 mm and consisting of a linker region about 2 mm wide comprising eight cylindrical polypropylene islands (each about 250 um in diameter) in a sea of PCL flanked on each side by PCL regions approximately 4.5 mm wide. Pure 80 k PCL was loaded into one extruder and polypropylene was loaded into the other. The melt flowrate set-points with the polypropylene flowrate were set to approximately 8% of the PCL flow rate. The molten ribbon exiting the co-extrusion head was guided onto a conveyor with a Teflon belt to both provide support to the ribbon and to allow it to harden before handling.

Example 6: Islands-in-the-Sea: Ribbon Cutting

The hardened precursor ribbon produced in Example 4 will then be cut as appropriate for the desired shape. To produce composite arms of the desired shape (e.g., triangular or pie-shaped cross section), the ribbon is cut perpendicular to the direction of extrusion.

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A co-extruded elongate member comprising;
   at least one carrier polymer-therapeutic agent (or salt thereof);
   at least one disintegrating linker, wherein the at least one disintegrating linker is a time-dependent linker and is configured to weaken to cause the elongate member to decouple or weaken; and
   a reinforcing material comprising one or more of polycaprolactone (PCL), polydioxanone, polylactic acid, polycarbonate, polyether ether ketone, polyethylene, or polypropylene,
   wherein the disintegrating linker comprises PCL, and
   wherein the reinforcing material extends axially along the co-extruded elongate member,
   wherein said elongate member is configured for use in a stellate gastric residence system having a gastric residence time between about 48 hours and one month.

2. A co-extruded elongate member comprising:
   at least two segments, each segment comprising a proximal end, a distal end, and an outer surface therebetween; and
   a reinforcing material comprising one or more of polycaprolactone (PCL), polydioxanone, polylactic acid, polycarbonate, polyether ether ketone, polyethylene, or polypropylene,
   wherein the at least two segments are attached together via a linker region comprising a disintegrating linker comprising PCL, wherein the at least one disintegrating linker is a time-dependent linker and is configured to weaken to cause the elongate member to decouple or weaken, and
   wherein the reinforcing material extends axially along one or more of the at least two segments,
   wherein said elongate member is configured for use in a stellate gastric residence system having a gastric residence time between about 48 hours and one month.

3. The elongate member of claim 2, wherein the disintegrating linker is an enteric linker.

4. The elongate member of claim 2, wherein the disintegrating linker comprises HPMCAS and PCL in a ratio of between about 80 HPMCAS:20 PCL to about 50 HPMCAS:50 PCL.

5. The elongate member of claim 2, wherein the disintegrating linker further comprises a plasticizer.

6. The elongate member of claim 5, wherein the plasticizer comprises triacetin, triethyl citrate, tributyl citrate, poloxamers, polyethylene glycol, polypropylene glycol, diethyl phthalate, dibutyl sebacate, glycerin, castor oil, acetyl triethyl citrate, acetyl tributyl citrate, polyethylene glycol monomethyl ether, sorbitol, sorbitan, a sorbitol-sorbitan mixture, or diacetylated monoglycerides, or mixtures thereof.

7. The elongate member of claim 2, wherein the segments comprise PCL.

8. The elongate member of claim 4, wherein the segments comprise PCL.

9. The elongate member of claim 2, wherein the elongate member has a triangular cross-section with rounded corners and edges.

10. The elongate member of claim 2, wherein the linker region is about 1 mm to about 2 mm in length.

11. The elongate member of claim 2, wherein the segments are about 2 mm to about 20 mm in length.

12. The co-extruded elongate member of claim 1, wherein the reinforcing material extends axially along a single side of the outer surface of the co-extruded elongate member.

13. The co-extruded elongate member of claim 1, wherein the reinforcing material comprises polycaprolactone without therapeutic agent or salt thereof.

14. The elongate member of claim 2, wherein the reinforcing material extends axially along a single side of the outer surface of one or more of the at least two segments.

15. The elongate member of claim 2, wherein the reinforcing material comprises polycaprolactone without therapeutic agent or salt thereof.

16. A gastric residence system comprising an elongate member of claim 2.

17. A method of manufacturing the elongate member of claim 2 for use in a gastric residence system, comprising: co-extruding the elongate member.

18. The method of claim 17, wherein co-extruding the elongate member comprises:
co-extruding a ribbon comprising at least two ribbon strip regions comprising a carrier polymer-therapeutic agent (or salt thereof) blend and at least one ribbon strip region comprising a linker region blend, wherein each ribbon strip region of carrier polymer-agent blend is separated from an adjacent ribbon strip region of carrier polymer-agent blend by a ribbon strip region comprising a linker blend.

19. The method of claim 17, where co-extruding the elongate member comprises:
co-extruding a ribbon comprising two ribbon strip regions comprising a carrier polymer-therapeutic agent (or salt thereof) blend and a ribbon strip region comprising a linker blend, wherein the two regions of carrier polymer-agent blend are separated by the linker region.

20. The method of claim 19, further comprising cutting the ribbon in a direction perpendicular to the direction of extrusion to form the elongate member.

21. The method of claim 17, where co-extruding the elongate member comprises:
co-extruding a ribbon comprising a region comprising a carrier polymer-therapeutic agent (or salt thereof) blend and a region comprising a linker.

22. The method of claim 21, further comprising cutting the ribbon in a direction perpendicular to the direction of extrusion to form the elongate member.

23. The method of claim 18, wherein the carrier polymer of the carrier polymer-therapeutic agent (or salt thereof) blend is selected from the group consisting of polycaprolactone and polydioxanone.

24. The method of claim 18, wherein the therapeutic agent (or salt thereof) of the carrier polymer-therapeutic agent (or salt thereof) blend is selected from the group consisting of analgesics; anti-analgesics; anti-inflammatory drugs; antipyretics; antidepressants; antiepileptics; antipsychotic agents; neuroprotective agents; anti-proliferatives; anti-cancer agents; antihistamines; antimigraine drugs; hormones; prostaglandins; antimicrobials; antibiotics; antifungals; antivirals; antiparasitics; anti-muscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; antimalarial drug; quinine; lumefantrine; chloroquine; amodiaquine; pyrimethamine; proguanil; chlorproguanil-dapsone; sulfonamides; sulfadoxine; sulfamethoxypyridazine; mefloquine; atovaquone; primaquine; halofantrine; doxycycline; clindamycin; artemisinin; artemisinin derivatives; artemether; dihydroartemisinin; arteether; and artesunate.

25. The method of claim 18, wherein the linker region comprises a material selected from the group consisting of an enteric linker and a time-dependent linker.

26. The method of claim 18, wherein the linker region comprises hydroxypropyl methyl cellulose acetate succinate (HPMC-AS) and polycaprolactone.

27. The method of claim 17, wherein the co-extruding is at a rate sufficient to prepare between about 30 and about 500 elongate members per minute.

28. The method of claim 17, wherein the co-extruding is performed at a rate sufficient to produce elongate members between about 5 to about 50 times faster than single-component extrusion at the same linear extrusion rate.

29. The method of claim 18, wherein at least one junction between a carrier polymer-agent region and a linker region is co-extruded in an interlocking configuration.

30. The method of claim 18, wherein at least one carrier polymer-agent region is co-extruded in an islands-in-the-sea configuration.

31. The method of claim 18, wherein at least one linker region is co-extruded in an islands-in-the-sea configuration.

32. The method of claim 30, wherein the island components of the islands-in-the-sea configuration comprise at least one material selected from the group consisting of an enteric polymer and a time-dependent polymer.

33. The method of claim 18, wherein the linker regions uncouple after about seven days in fasted-state simulated gastric fluid.

34. The method of claim 17, wherein co-extruding the elongate member comprises:
co-extruding a carrier polymer-therapeutic agent (or salt thereof) blend and a reinforcing material.

* * * * *